(12) United States Patent
Pegan et al.

(10) Patent No.: US 8,097,422 B2
(45) Date of Patent: Jan. 17, 2012

US008097422B2

(54) KIR CHANNEL MODULATORS

(75) Inventors: Scott D. Pegan, Oak Park, IL (US); Paul A. Slesinger, San Diego, CA (US); Senyon Choe, Solana, CA (US); Prafulla Aryal, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 59 days.

(21) Appl. No.: 12/141,026

(22) Filed: Jun. 17, 2008

(65) Prior Publication Data

US 2009/0148861 A1   Jun. 11, 2009

Related U.S. Application Data

(60) Provisional application No. 60/945,321, filed on Jun. 20, 2007.

(51) Int. Cl.
*G01N 33/566* (2006.01)

(52) U.S. Cl. .......... 435/7.1; 435/7.2; 435/7.21; 436/501

(58) Field of Classification Search .................. None
See application file for complete search history.

(56) References Cited

U.S. PATENT DOCUMENTS

| | | |
|---|---|---|
| 4,469,863 A | 9/1984 | Ts'o et al. |
| 4,868,103 A | 9/1989 | Stavrianopoulos et al. |
| 4,987,071 A | 1/1991 | Cech et al. |
| 5,093,246 A | 3/1992 | Chech et al. |
| 5,096,815 A | 3/1992 | Ladner et al. |
| 5,116,742 A | 5/1992 | Cech et al. |
| 5,198,346 A | 3/1993 | Ladner et al. |
| 5,223,409 A | 6/1993 | Ladner et al. |
| 5,232,841 A | 8/1993 | Hashimoto et al. |
| 5,268,273 A | 12/1993 | Buckholz |
| 5,389,529 A | 2/1995 | Panayotatos et al. |
| 5,403,484 A | 4/1995 | Ladner et al. |
| 5,470,719 A | 11/1995 | Meng et al. |
| 5,530,101 A | 6/1996 | Queen et al. |
| 5,536,821 A | 7/1996 | Agrawal et al. |
| 5,541,306 A | 7/1996 | Agrawal et al. |
| 5,571,698 A | 11/1996 | Ladner et al. |
| 5,614,622 A | 3/1997 | Iyer et al. |
| 5,631,169 A | 5/1997 | Lakowicz et al. |
| 5,637,683 A | 6/1997 | Usher et al. |
| 5,637,684 A | 6/1997 | Cook et al. |
| 5,641,640 A | 6/1997 | Hanning |
| 5,700,922 A | 12/1997 | Cook |
| 5,707,622 A | 1/1998 | Fung et al. |
| 5,712,114 A | 1/1998 | Mankovich et al. |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,766,905 A | 6/1998 | Studier et al. |
| 5,773,601 A | 6/1998 | Agrawal |
| 5,846,818 A | 12/1998 | Robinson et al. |
| 5,886,165 A | 3/1999 | Kandimalla et al. |
| 5,900,481 A | 5/1999 | Lough et al. |
| 5,929,226 A | 7/1999 | Padmapriya et al. |
| 5,932,474 A | 8/1999 | Tsien et al. |
| 5,955,599 A | 9/1999 | Iyer et al. |
| 5,955,729 A | 9/1999 | Nelson et al. |
| 5,962,674 A | 10/1999 | Iyer et al. |
| 5,977,296 A | 11/1999 | Nielsen et al. |
| 5,990,296 A | 11/1999 | Pastan et al. |
| 5,994,524 A | 11/1999 | Matsushima et al. |
| 6,008,378 A | 12/1999 | Tsien et al. |
| 6,022,688 A | 2/2000 | Jurinke et al. |
| 6,054,271 A | 4/2000 | Tsien et al. |
| 6,090,919 A | 7/2000 | Cormack et al. |
| 6,099,842 A | 8/2000 | Pastan et al. |
| 6,117,992 A | 9/2000 | Iyer |
| 6,127,183 A | 10/2000 | Ivarsson et al. |
| 6,133,436 A | 10/2000 | Koster et al. |
| 6,140,482 A | 10/2000 | Iyer et al. |
| 6,143,574 A | 11/2000 | Karlsson et al. |
| 6,207,381 B1 | 3/2001 | Larsson et al. |
| 6,214,560 B1 | 4/2001 | Yguerabide et al. |
| 6,245,894 B1 | 6/2001 | Matsushima et al. |
| 6,261,776 B1 | 7/2001 | Pirrung et al. |
| 6,288,302 B1 | 9/2001 | Yu et al. |
| 6,316,781 B1 | 11/2001 | Nagle et al. |
| 6,342,221 B1 | 1/2002 | Thorpe et al. |
| 6,379,974 B1 | 4/2002 | Parce et al. |
| 6,429,025 B1 | 8/2002 | Parce et al. |
| 6,440,722 B1 | 8/2002 | Knapp et al. |
| 6,451,569 B1 | 9/2002 | Tsien et al. |
| 6,455,263 B2 | 9/2002 | Payan |
| 6,461,813 B2 | 10/2002 | Lorens |
| 2003/0083373 A1 | 5/2003 | Tsien et al. |
| 2006/0194949 A1 | 8/2006 | Downes et al. |

FOREIGN PATENT DOCUMENTS

| | | |
|---|---|---|
| WO | WO 90/05295 | 5/1990 |
| WO | WO 99/32619 | 1/1999 |
| WO | WO 99/07409 | 2/1999 |
| WO | WO 99/21013 | 4/1999 |
| WO | WO 00/01846 | 1/2000 |

(Continued)

OTHER PUBLICATIONS

Kobayashi et al., Ethanol opens G-protein-activated inwardly rectifying K+ channels, Dec. 1999, Nature Neuroscience 2(12):1091-1097.*

Lewohl et al., G-protein-coupled inwardly rectifying potassium channels are targests of alcohol action, Dec. 999, Nqature Neuroscience 2(12):1084-1090.*

Zhou et al., Mechanism underlying bupivacaine inhibition of G protein-gated inwardly rectifying K+ channels, May 22, 2001, P.N.A.S. 98(11):6482-6487.*

Altschul et al., J. Mol. Biol. 215: 403-10 (1990).

Allshire, 2002, Science, 297, 1818-1819.

Altschul et al., Nucleic Acids Res. 25(17): 3389-3402 (1997).

Anantha, et al., Biochemistry (1998) 37:2709-2714.

U.S. Appl. No. 09/518,188, filed Mar. 2, 2000, Hartley.

(Continued)

*Primary Examiner* — John Ulm
(74) *Attorney, Agent, or Firm* — Grant Anderson LLP

(57) ABSTRACT

Provided is a three-dimensional structure of an alcohol bound to an alcohol-binding site of an inwardly rectifying potassium (Kir) channel, Kir channel alcohol modulators and methods for identifying Kir channel modulators.

26 Claims, 22 Drawing Sheets

FOREIGN PATENT DOCUMENTS

| | | |
|---|---|---|
| WO | WO 00/44895 | 8/2000 |
| WO | WO 00/44914 | 8/2000 |
| WO | WO 00/56746 | 9/2000 |
| WO | WO 00/75372 | 12/2000 |
| WO | WO 01/14398 | 3/2001 |
| WO | WO 01/18234 | 3/2001 |
| WO | WO 01/29058 | 4/2001 |
| WO | WO 01/36486 | 5/2001 |
| WO | WO 01/36646 | 5/2001 |

OTHER PUBLICATIONS

Arthanari & Bolton, Anti-Cancer Drug Design 14: 317-326 (1999).
Bartel & Szostak, Science 261: 1411-1418 (1993).
Bass, 2001, Nature, 411, 428-429.
Bendahhou, S., et al., Defective potassium channel Kir2.1 trafficking underlies Andersen-Tawil syndrome. J Biol Chem, 2003. 278(51): p. 51779-51785.
Bendahhou, S., et al., In vivo and in vitro functional characterization of Andersen's syndrome mutations. J Physiol, 2005. 565(Pt 3): p. 731-41.
Blednov, Y.A., Stoffel, M., Alva, H., and Harris, R.A. (2003). A pervasive mechanism for analgesia: activation of GIRK2 channels. Proc Natl Acad Sci U S A 100, 277-282.
Blednov, Y.A., Stoffel, M., Chang, S.R., and Harris, R.A. (2001). Potassium channels as targets for ethanol: studies of G-protein-coupled inwardly rectifying potassium channel 2 (GIRK2) null mutant mice. J Pharmacol Exp Ther 298, 521-530.
Calloe et al., Biochem Biophys Res Commun. Dec. 28, 2007;364(4):889-95.
Cardoso, R.A., Brozowski, S.J., Chavez-Noriega, L.E., Harpold, M., Valenzuela, C.F., and Harris, R.A. (1999). Effects of ethanol on recombinant human neuronal nicotinic acetylcholine receptors expressed in Xenopus oocytes. J Pharmacol Exp Ther 289, 774-780.
Carell et al., Angew. Chem. Int. Ed. Engl. 33: 2061 (1994).
Carrell et al., Angew. Chem. Int. Ed. Engl. 33: 2059 (1994).
Chen, L., et al., A glutamate residue at the C terminus regulates activity of inward rectifier K+ channels: implication for Andersen's syndrome. Proc Natl Acad Sci U S A, 2002. 99(12): p. 8430-5.
Cho et al., "An unnatural biopolymer," Science 3 ;261(5126) :1303-1305 (1993).
Cordero-Morales JF et al., "Molecular driving forces determining potassium channel slow inactivation," Nat Struct Mol Biol. Nov. 2007;14(11):1062-1069.
Cordero-Morales JF et al., "Molecular determinants of gating at the potassium-channel selectivity filter," Nature Structure & Molecular Biology, 13, 311-318 (2006).
Cordero-Morales JF et al., "Voltage-dependent gating at the KcsA selectivity filter," Nature Structural & Molecular Biology 13, 319-322 (2006).
Cull et al., Proc. Natl. Acad. Sci. USA 89: 1865-1869 (1992).
Current Protocols in Molecular Biology, John Wiley & Sons, N.Y. , 6.3.1-6.3.6 (1989).
Cwirla et al., Proc. Natl. Acad. Sci. 87: 6378-6382 (1990).
Deitrich, R.A., Dunwiddie, T.V., Harris, R.A., and Erwin, V.G. (1989). Mechanism of action of ethanol: initial central nervous system actions. Pharmacol Rev 41, 489-537.
Devlin, Science 249: 404-406 (1990).
DeWitt et al., Proc. Natl. Acad. Sci. U.S.A. 90: 6909 (1993).
Donaldson, M.R., et al., PIP2 binding residues of Kir2.1 are common targets of mutations causing Andersen syndrome. Neurology, 2003. 60(11): p. 1811-1816.
Elbashir et al., 2001, Nature, 411, 494-498.
Erb et al., Proc. Natl. Acad. Sci. USA 91: 11422 (1994).
Felici, J. Mol. Biol. 222: 301-310 (1991).
Fink, M., et al., Dominant negative chimeras provide evidence for homo and heteromultimeric assembly of inward rectifier K+ channel proteins via their N-terminal end. FEBS Lett, 1996. 378(1): p. 64-8.
Finley, M., et al., betaL-betaM loop in the C-terminal domain of G protein-activated inwardly rectifying K(+) channels is important for G(betagamma) subunit activation. J Physiol, 2004. 555(Pt 3): p. 643-57.
Fodor, Nature 364: 555-556 (1993).
Gallop et al., J. Med. Chem. 37: 1233 (1994).
Gaultier et al., Nucleic Acids. Res. 15: 6625-6641 (1987).
Gottschling et al., Bioorg. And Medicinal Chem. Lett. 11: 2997 (2001).
Hall et al., 2002, Science, 297, 2232-2237.
He, C., Zhang, H., Mirshahi, T., and Logothetis, D.E. (1999). Identification of a potassium channel site that interacts with G protein betagamma subunits to mediate agonist-induced signaling. J Biol Chem 274, 12517-12524.
Hosaka, Y., et al., Function, subcellular localization and assembly of a novel mutation of KCNJ2 in Andersen's syndrome. J Mol Cell Cardiol, 2003. 35(4): p. 409-15.
Houghten, Biotechniques 13: 412-421 (1992).
Huang, C.L., S. Feng, and D.W. Hilgemann, Direct activation of inward rectifier potassium channels by PIP2 and its stabilization by Gbetagamma Nature, 1998. 391(6669): p. 803-6.
Hutvagner and Zamore, 2002, Science, 297, 2056-60.
Inanobe, A., Matsuura, T., Nakagawa, A., Kurachi, Y. (2007). Structural Diversity in the Cytoplasmic Region of G Protein-Gated Inward Rectifier K+ Channels 139-45.
Inoue et al., FEBS Lett. 215: 327-330 (1987).
Jenuwein, 2002, Science, 297, 2215-2218.
Kessler et al., Agnew. Chem. Int. Ed. 40: 165 (2001).
Kobayashi, T., et al., Ethanol opens G-protein-activated inwardly rectifying K+ channels. Nature Neuroscience 1999. 2(12): pp. 1091-1097.
Kohler & Milstein, Nature 256:495 497 (1975).
Kruse, S.W., Zhao, R., Smith, D.P., and Jones, D.N. (2003). Structure of a specific alcohol-binding site defined by the odorant binding protein LUSH from *Drosophila melanogaster*. Nat Struct Biol 10, 694-700.
Kubo, Y. and Y. Murata, Control of rectification and permeation by two distinct sites after the second transmembrane region in Kir2.1 K+ channel. J Physiol, 2001. 531(Pt 3): p. 645-60.
Kubo, Y., et al., Primary structure and functional expression of a mouse inward rectifier potassium channel. Nature, 1993. 362(6416): p. 127-33.
Kuo, A., et al., Crystal structure of the potassium channel KirBac1.1 in the closed state. Science, 2003. 300(5627): p. 1922-6.
Lam, Anticancer Drug Des. 12: 145, (1997).
Lam, Nature 354: 82-84 (1991).
Leon et al., Bioorg. Med. Chem. Lett. 8: 2997 (1998).
Lewohol, J., et al., G-protein-coupled inwardly rectifying potassium channels are targets of alcohol action. Nature Neuroscience 1999. 2(12): p. 1084-1090.
Long, S.B., E.B. Campbell, and R. Mackinnon, Crystal structure of a mammalian voltage-dependent Shaker family K+ channel. Science, 2005. 309(5736): p. 897-903.
Lopatin, A.N., E.N. Makhina, and C.G. Nichols, Potassium channel block by cytoplasmic polyamines as the mechanism of intrinsic rectification. Nature, 1994. 372(6504): p. 366-9.
Lopes, C.M., et al., Alterations in conserved Kir channel-PIP2 interactions underlie channelopathies. Neuron, 2002. 34(6): p. 933-44.
Lovinger, D.M., White, G., and Weight, F.F. (1989). Ethanol inhibits NMDA-activated ion current in hippocampal neurons. Science 243, 1721-1724.
Lu, Z. and R. MacKinnon, Electrostatic tuning of Mg2+ affinity in an inward-rectifier K+ channel. Nature, 1994. 371(6494): p. 243-6.
Lu, Z., A.M. Klem, and Y. Ramu, Ion conduction pore is conserved among potassium channels. Nature, 2001. 413(6858): p. 809-13.
McManus et al., 2002, RNA, 8, 842-850.
McPherson, J. Biol. Chem. 251:6300-6303 (1976).
Meyers & Miller, CABIOS 4: 11-17 (1989).
Mihic, S.J., Ye, Q., Wick, M.J., Koltchine, V.V., Krasowski, M.D., Finn, S.E., Mascia, M.P., Valenzuela, C.F., Hanson, K.K., Greenblatt, E.P., et al. (1997). Sites of alcohol and volatile anaesthetic action on GABA(A) and glycine receptors. Nature 389, 385-389.
Needleman & Wunsch, J. Mol. Biol. 48: 444-453 (1970).
Nichols, C.G. and A.N. Lopatin, Inward rectifier potassium channels. Annu Rev Physiol, 1997. 59: p. 171-91.

Nishida, M. and R. MacKinnon, Structural basis of inward rectification: cytoplasmic pore of the G protein-gated inward rectifier GIRK1 at 1.8 A resolution. Cell, 2002. 111(7): p. 957-65.
Orain et al., Tetrahedron Lett. 42: 515 (2001).
Papanikos et al., J. Am. Chem. Soc. 123: 2176 (2001).
Pegan, S., Arrabit, C., Slesinger, P.A., and Choe, S. (2006). Andersen's syndrome mutation effects on the structure and assembly of the cytoplasmic domains of Kir2.1. Biochemistry 45, 8599-8606.
Pegan, S., et al., Cytoplasmic domain structures of Kir2.1 and Kir3.1 show sites for modulating gating and rectification. Nat Neurosci, 2005. 8(3): p. 279-87.
Periole, X., et al., Simple Two-body Cation-Water Interaction Potentials Derived from ab Initio Calculations. Comparision to Results Obtained with an Empirical Approach. J. Phys. Chem., 1997(101): p. 5018-5025.
Plaster, N.M., et al., Mutations in Kir2.1 cause the developmental and episodic electrical phenotypes of Andersen's syndrome. Cell, 2001. 105(4): p. 511-9.
Preisig-Muller, R., et al., Heteromerization of Kir2.x potassium channels contributes to the phenotype of Andersen's syndrome. Proc Natl Acad Sci U S A, 2002. 99(11): p. 7774-9.
Qu & Chaires, Methods Enzymol. (2000) 321:353 369).
Reinhart & Bartel, 2002, Science, 297, 1831.
Reinhart et al., 2002, Gene & Dev., 16, 1616-1626.
Rishal, I., Porozov, Y., Yakubovich, D., Varon, D., and Dascal, N. (2005). Gbetagamma-dependent and Gbetagamma-independent basal activity of G protein-activated K+ channels. J Biol Chem 280, 16685-16694.
Sarac, R., Hou, P., Hurley, K.M., Hriciste, D., Cohen, N.A., and Nelson, D.J. (2005). Mutation of critical GIRK subunit residues disrupts N- and C-termini association and channel function. J Neurosci 25, 1836-1846.
Scott and Smith, Science 249: 386-390 (1990).
Signorini, S., Liao, Y.J., Duncan, S.A., Jan, L.Y., and Stoffel, M. (1997). Normal cerebellar development but susceptibility to seizures in mice lacking G protein-coupled, inwardly rectifying K+ channel GIRK2. Proc Natl Acad Sci U S A 94, 923-927.
Silverman, S.K., H.A. Lester, and D.A. Dougherty, Subunit stoichiometry of a heteromultimeric G protein-coupled inward-rectifier K+ channel. J Biol Chem, 1996. 271(48): p. 30524-8.
Smith et al., J. Comb. Med. 1: 326 (1999).
StGroth & Scheidegger, J Immunol Methods 5:1 21 (1980).
Tjalsma et al., Microbiol.Molec. Biol. Rev. 64: 515-547 (2000).
Tristani-Firouzi, M., et al., Functional and clinical characterization of KCNJ2 mutations associated with LQT7 (Andersen syndrome). J Clin Invest, 2002. 110(3): p. 381-8.
Vivaudou, M., Chan, K.W., Sui, J.L., Jan, L.Y., Reuveny, E., and Logothetis, D.E. (1997). Probing the Gprotein regulation of GIRK1 and GIRK4, the two subunits of the KACh channel, using functional homomeric mutants. J Biol Chem 272, 31553-31560.
Volpe et al., 2002, Science, 297, 1833-1837.
Weber, Adv. Prot. Chem. 41:1-36 (1991).
Wick, M.J., Mihic, S.J., Ueno, S., Mascia, M.P., Trudell, J.R., Brozowski, S.J., Ye, Q., Harrison, N.L., and Harris, R.A. (1998). Mutations of gamma-aminobutyric acid and glycine receptors change alcohol cutoff: evidence for an alcohol receptor? Proc Natl Acad Sci U S A 95, 6504-6509.
Zamore et al., 2000, Cell, 101, 25-33.
Zaritsky, J.J., et al., The consequences of disrupting cardiac inwardly rectifying K(+) current (I(K1)) as revealed by the targeted deletion of the murine Kir2.1 and Kir2.2 genes. J Physiol, 2001. 533(Pt 3): p. 697-710.
Zhang, H., He, C., Yan, X., Mirshahi, T., and Logothetis, D.E. (1999). Activation of inwardly rectifying K+ channels by distinct PtdIns(4,5)P2 interactions. Nat Cell Biol 1, 183-188.
Zhou, Q., and Lovinger, D.M. (1996). Pharmacologic characteristics of potentiation of 5-HT3 receptors by alcohols and diethyl ether in NCB-20 neuroblastoma cells. J Pharmacol Exp Ther 278, 732-740.
Zhou, W., et al., Mechanism underlying bupivacaine inhibition of g protein-gated inwardly rectifying K+ channels. Proc. Natl. Acad. Sci. 2006. 98: p. 6482-6487.
Zhou, Y., et al., Chemistry of ion coordination and hydration revealed by a K+ channel-Fab complex at 2.0 A resolution. Nature, 2001. 414(6859): p. 43-8.
Zuckermann et al., J. Med. Chem.37: 2678-85 (1994).
Fujiwara, Y. And Y. Kubo, "Functional Roles of Charged Amino Acid Residues on the Wall of the Cytoplasmic Pore of Kir2.1," J Gen Physiol. Apr. 2006;127(4):401-419.
Hille, B., "Ion Channels of Excitable Membranes," Third ed. 2001, Sinauer Associates, Inc., Publishers, Sunderland, Massachusetts USA. pp. vii-xviii, 1-22, 61-93, 131-167, 217-234, 405-440, 503-537, and 566-572.

* cited by examiner

```
         N1
IRK1 :  41-QQCRSRFVKKDGHCNVQFINVG-62
GIRK2:  52-KRKIQRYVRKDGKCNVHHGNVR-73

C1 (βDβE)                        C2 (βLβM)
230-QLLKSRITSEGEYIPL-245          326-YEPVLFEEKHYYKVDY-341
242-KLIKSKQTSEGEFIPL-257          338-FTPVLTLEDGFYEVDY-353
```

N1 domain

```
Kir1.1_rat  RRWFITHIFGR--------SRQRARLVSKEGRCNIEFGNVDAQSRFIFFVDIW   69
Kir2.1_rat  GNGKSKVHT-R---------QQCRSRFVKKDGHCNVQFINVGEKG-QRYLADIF   73
Kir2.2_rat  GNG---KVHT-R---------RRCRNRFVKKNGQCNIEFANMDEKS-QRYLADMF  72
Kir2.3_rat  RNG---QAHVPR---------RKRRNRFVKKNGQCNVYFANLSNKS-QRYMADIF  47
Kir3.1_rat  GQGPQGQLVPK----------KKRQRFVDKNGRCNVQHGNLGSET-SRYLSDLF   72
Kir3.2_rat  DDLPRHISRDR------TKRKIQRYVRKDGKCNVHHGNVR-ET-YRYLTDIF    83
Kir3.3_rat  AFSPGSEEPPR------RRGRQRYVEKDGRCNVQQGNVR-ET-YRYLTDLF     49
Kir3.4_rat  DYIPIATDRTRLLPEGKKPRQRYMEKTGKCNVHHGNVQ-ET-YRYLSDLF      78
Kir4.1_rat  ----SRPLVAPG---------IRRRRVLTKDGRSNVRMEHIADKR-FLYLKDLW  56
Kir4.2_rat  ---HTNGVGLK----------AHRPRVMSKSGHSNVRIDKVDGIY-LLYLQDLW  55
Kir5.1_rat  GYPPEHAIAEK------RRARRRLLHKDGSCNVYFKHIFGEW-GSYMVDIF     62
Kir6.1_rat  ENLRKPRIRDR--------LPKARFIAKSGACNLAHKNIR-EQ-GRFLQDIF    61
Kir6.2_rat  D-PTEPRYRTR--------ERRARFVSKKGNCNVAHKNIR-EQ-GRFLQDVF    60
Kir7.1_rat  ----APLLSQR----------YRRMVTKDGHSTLQMDGAQRG--LVYLRDAW   45
```

Pore Helix

```
Kir1.1_rat  ---------CVENINGMTSAFLFSLETQVTIGYGFRFVTEQCATA  156
Kir2.1_rat  ---------CVSEVNSFTAAFLFSIETQTTIGYGFRCVTDECPIA  157
Kir2.2_rat  ---------CVLQVHGFMAAFLFSIETQTTIGYGLRCVTEECPVA  158
Kir2.3_rat  ---------CIMHVNGFLGAFLFSVETQTTIGYGFRCVTEECPLA  149
Kir3.1_rat  ---------CVANVYNFPSAFLFFIETEATIGYGYRYITDKCPEG  158
Kir3.2_rat  ---------CVTNLNGFVSAFLFSIETETTIGYGYRVITDKCPEG  169
Kir3.3_rat  ---------CVNNLNGFVAAFLFSIETETTIGYGHRVITDQCPEG  135
Kir3.4_rat  ---------CVENLSGFVSAFLFSIETETTIGYGFRVITEKCPEG  164
Kir4.1_rat  ---------CVVQVHTLTGAFLFSLESQTTIGYGFRYISEECPLA  143
Kir4.2_rat  ---------CIMKVDSLTGAFLFSLESQTTIGYGVRSITEECPHA  142
Kir5.1_rat  ---------CVDNVHSFTAAFLFSLETQTTIGYGYRCVTEECSVA  146
Kir6.1_rat  KSGLESAVCVTNVRSFTSAFLFSIEVQVTIGFGGRMMTEECPLA   155
Kir6.2_rat  ---------CVTSIHSFSSAFLFSIEVQVTIGFGGRMVTEECPLA  145
Kir7.1_rat  ---------ICVKHITSFTAAFSFSLETQLTIGYGTMFPSGDCPSA 134
```

FIG.10A

βD-βE domain

```
Kir1.1_rat  YGKLLKTTITPEGETIILDQTNINFVVDAGNENLFFISPL  266
Kir2.1_rat  RAQLLKSRITSEGEYIPLDQIDINVGFDSGIDRIFLVSPI  267
Kir2.2_rat  RAQLIKPRVTEEGEYIPLDQIDIDVGFDKGLDRIFLVSPI  268
Kir2.3_rat  RAQLIKPYMTQEGEYLPLDQRDLNVGYDIGLDRIFLVSPI  259
Kir3.1_rat  RCKLLKSRQTPEGEFLPLDQLELDVGFSTGADQLFLVSPL  268
Kir3.2_rat  RAKLIKSKQTSEGEFIPLNQTDINVGYYTGDDRLFLVSPL  279
Kir3.3_rat  RAKLIRSRQTLEGEFIPLHQTDLSVGFDTGDDRLFLVSPL  245
Kir3.4_rat  RAKLIKSRQTKEGEFIPLNQTDINVGFDTGDDRLFLVSPL  274
Kir4.1_rat  TGKLLQTHQTKEGENIRLNQVNVTFQVDTASDSPFLILPL  253
Kir4.2_rat  SGKLLQTHVTKEGERILLNQATVKFHVDSSSESPFLILPM  252
Kir5.1_rat  RAQLLRYSEDSEG-RTMMAFKDLKLVN----DQIILVTPL  251
Kir6.1_rat  RIQVVKKTTTPEGEVVPTHQQDIPVDNPIESNNIFLVAPL  265
Kir6.2_rat  HMQVVRKTTSPEGEVVPLHQVDIPMENGVGGNSIFLVAPL  255
Kir7.1_rat  SAVLYQERENGE---LYQTSVDFHLDGISSEECPFFIFPL  241
```

βL-βM domain

```
Kir1.1_rat  ATCQVRTSYVPEEVLWGYRFVPIVSKTKEGKYRVDFHNFG  345
Kir2.1_rat  MTTQCRSSYLANEILWGHRYEPVLFE-EKHCYKVDYSRFH  345
Kir2.2_rat  MTTQARSSYLANEILWGHRFEPVLFE-EKNQYKIDYSHFH  346
Kir2.3_rat  MTTQARSSYLASEILWGHRFEPVVFE-EKSHYKVDYSRFH  337
Kir3.1_rat  MTCQARTSYTEDEVLWGHRFFPVISL-EEGFFKVDYSWFH  346
Kir3.2_rat  MTCQARSSYVTSEILWGYRFTPVLTL-EDGFYEVDYNSFH  357
Kir3.3_rat  MTCQARSSYLVDEVLWGHRFTSVLTL-EDGFYEVDYASFH  323
Kir3.4_rat  MTCQARSSYMDTEVLWGHRFTPVLTL-EKGFYEVDYNTFH  352
Kir4.1_rat  ATCQVRTSYLPEEILWGYEFTPAISLSASGKYVADFSLFD  331
Kir4.2_rat  AVCQSRTSYIPEEIYWGFEFVPVVSLSKNGKYVADFSQFE  331
Kir5.1_rat  TSHQSRSSYVPREILWGHRFHDVLEV-KRKYYKVNCLQFE  329
Kir6.1_rat  ITTQARTSYIAEEIQWGHRFVSIVTE-EEGVYSVDYSKFG  343
Kir6.2_rat  ITTQARTSYLADEILWGQRFVPIVAE-EDGRYSVDYSKFG  334
Kir7.1_rat  EICQRRTSYLPSEIMLHHRFAALMTRGSKGEYQVKMENFD  319
```

FIG.10B ns with chimeric KcsA/Kir2.1 channels indicate the cytoplasmic domain is required for Kir2.1 gating [18].

SEQUENCE LISTING

<160> NUMBER OF SEQ ID NOS: 49

<210> SEQ ID NO 1
<211> LENGTH: 5397
<212> TYPE: DNA
<213> ORGANISM: Homo sapiens

<400> SEQUENCE: 1

| | | | | | | |
|---|---|---|---|---|---|---|
| gcgcactgga | gccctggcca | gcgcgcagcc | ttcccggcgc | cggcgggctg | ggtcttggga | 60 |
| attctggttt | gctttggctc | actcgctttt | tacaaaccac | tggatcttac | atgcctctgt | 120 |
| acccccact | tccactccat | gtccccatgc | tcctgcgcca | gcaacaggac | atgttctctg | 180 |
| gatgtcagct | gagtcattaa | agtaactctg | catgtcagta | gacagacctt | ggtagaacca | 240 |
| caaggctccc | agagacaccc | atctctcctc | atttttttgg | tgtgtgtgtc | ttcaccgaac | 300 |
| attcaaaact | gtttctccaa | agcgttttgc | aaaaactcag | actgttttcc | aaagcagaag | 360 |
| cactggagtc | cccagcagaa | gcgatgggca | gtgtgcgaac | caaccgctac | agcatcgtct | 420 |
| cttcagaaga | agacggtatg | aagttggcca | ccatggcagt | tgcaaatggc | tttgggaacg | 480 |
| ggaagagtaa | agtccacacc | cgacaacagt | gcaggagccg | ctttgtgaag | aaagatggcc | 540 |
| actgtaatgt | tcagttcatc | aatgtgggtg | agaaggggca | acggtacctc | gcagacatct | 600 |
| tcaccacgtg | tgtggacatt | cgctggcggt | ggatgctggt | tatcttctgc | ctggctttcg | 660 |
| tcctgtcatg | gctgtttttt | ggctgtgtgt | tttggttgat | agctctgctc | catgggacc | 720 |
| tggatgcatc | caaagagggc | aaagcttgtg | tgtccgaggt | caacagcttc | acggctgcct | 780 |
| tcctcttctc | cattgagacc | cagacaacca | taggctatgg | tttcagatgt | gtcacggatg | 840 |
| aatgcccaat | tgctgttttc | atggtggtgt | tccagtcaat | cgtgggctgc | atcatcgatg | 900 |
| ctttcatcat | tggcgcagtc | atggccaaga | tggcaaagcc | aaagaagaga | acgagactc | 960 |
| ttgtcttcag | tcacaatgcc | gtgattgcca | tgagagacgg | caagctgtgt | ttgatgtggc | 1020 |
| gagtgggcaa | tcttcggaaa | agccacttgg | tggaagctca | tgttcgagca | cagctcctca | 1080 |
| aatccagaat | tacttctgaa | ggggagtata | tccctctgga | tcaaatagac | atcaatgttg | 1140 |
| ggtttgacag | tggaatcgat | cgtatatttc | tggtgtcccc | aatcactata | gtccatgaaa | 1200 |
| tagatgaaga | cagtccttta | tatgatttga | gtaaacagga | cattgacaac | gcagactttg | 1260 |
| aaatcgtggt | catactggaa | ggcatggtgg | aagccactgc | catgacgaca | cagtgccgta | 1320 |
| gctcttatct | agcaaatgaa | atcctgtggg | gccaccgcta | tgagcctgtg | ctctttgaag | 1380 |
| agaagcacta | ctacaaagtg | gactattcca | ggttccacaa | aacttacgaa | gtccccaaca | 1440 |
| ctccccttttg | tagtgccaga | gacttagcag | aaaagaaata | tatcctctca | aatgcaaatt | 1500 |
| cattttgcta | tgaaaatgaa | gttgccctca | caagcaaaga | ggaagacgac | agtgaaaatg | 1560 |
| gagttccaga | aagcactagt | acggacacgc | cccctgacat | agaccttcac | aaccaggcaa | 1620 |
| gtgtacctct | agagcccagg | cccttacggc | gagagtcgga | gatatgactg | actgattcct | 1680 |
| tctctggaat | agttacttta | caacacggtc | tgttggtcag | aggcccaaaa | cagttataca | 1740 |
| gatgacggta | ctggtcaaga | tgggtcaagc | aagcggccac | aagggactga | ggcaagcaca | 1800 |
| atggtttcaa | agaaagactg | taagctccat | gattagcata | aagcactaac | catgtctcca | 1860 |
| tgtgacccga | tggcacatag | atgttgtaga | ataagttatg | ggttttatg | ttttgttttg | 1920 |
| tgttttttcca | aaacttgaac | ttgcaggcaa | gccttggttg | ggtatttgat | ttatccagaa | 1980 |
| tgcttctctt | tagggaacaa | ggatgttttt | aatggcataa | caaaggcaag | actctgcctt | 2040 |

```
aatttttgaa aagctgctaa ctacatgaac acaaatgtgt attttttgttg cagtgtagtt    2100 ttccttttgt gtaattttaa agtcagtgtt gaatttatt gaaagctcat gatgcgcttc      2160
aaagtggcaa gtatttggct attaactgcc aaaacaagag cctgattttt tgaggccagt    2220
aattcgtttg ctagaattga ttttttttct ctctctcttt gttacataag ggcattatgt    2280
aacactagcc gaatggtagc ctctgggttg ttgttttttt cttttcctcc atgatgttaa    2340
tgggttatct caaattttaa gttaaactac ctaaaataaa taccaaagat aatgcatatt    2400
tttgcacagt ggagcttaca cttaaaagaa aacaaagccc catgggctgc cttgaaatca    2460
agagacaata actttgaacc tcagcaagac cttgaaccgc cggttcattt tgcaccttat    2520
tcagaaaata gagcatcata ctcaccgagt ctagtcagtg tagtgctttt aaaaattttg    2580
tcctttcatg taactttttt attttaagag gaagaagaag aaaggggcac acacacacaa    2640
taccgacgtc tatcctttcc tgctaggcag tgctggccag gctcatgtgt agtgtgcgag    2700
atggtgatgt actcttatat ttttctgggc ttttcctttt gcacattcca aaattcattt    2760
cataagacaa gatcttcata ggacctcctt ggcatcctgg cattctcaaa actgagccat    2820
ccagcatgaa agataaatgg gtttaaaccc ttgctgctga atttattgcc tggactgtca    2880
ggacatcacc agcccacctt caccttaggg aagatgccac acctggcctc cacacttgct    2940
cttctgatca gtctgtctgg attgagtcct acagtgtcag ataggcggc aaatgccaaa     3000 gcagggaaac agggaggtgt ggacaagcca gtttgatgca gcacttcaga tcaagtgctt    3060
aggaaggaga ggaaacttgc ctttttttatg gcagaggata gtaatgaaaa tgtctcagta    3120
ttttagggtc aatgagagcc ataaaaatat aacataatca caagtaaagg agataatggt    3180
ctaaaacagc tatttccctt ttctgtgtgc atacttatga ctgaatgtga gctaagcatt    3240
ttctcctgtg gagccctaga gcaggttact aaggaaggac acattgtttt ccagaagcct    3300
cccctgcctg gctgactgcc ttgctagaaa cataattttt ttttttctcac tgaagctcaa    3360 taatggaact cttttttttt ttttttttaa tttaagttc cctatttgtg aattctggga     3420
ttactgactt tcctttttaa ttggagtctc aaaatcaact ctcttatggt attatatctc    3480
tgtatgccat taaaaaacag cttgttctag aatcatgtat tttgtaaact gatgtttgtg    3540
atggtctctg gttcttgaac agccatatct gaatgccgtg cctgcaaaac tatgacaatt    3600
tttgctgttt tcagccttca gatttgatgg cttgggaaac tgaggtgtta ttttcaatga    3660
aacaaagaaa gagatgttaa gcaagtggtt gttttagatc caaatgtaaa ggcaggtttg    3720
ggaaggtgtt taaagagttg gaggaattgg ggattgagtt gtaaagaaaa cttacagaag    3780
aggcaacaat ttggttcttg acagtgagag gatattgagg gcttcagctg ctgctattat    3840
gatgttttgc aaaggaaaat aatcaaacca aagagtattc agtgatatgt aaattaaatg    3900
aagatacagt ggagaatggg ggtgaccaca aaagaggctc cccctaaaca cacagtgctg    3960
ccacttaaaa agacttgaga aatttgaaag ggggtgggta tggggggggc aagaaagagg    4020
gagggaaatc tttcaactta tttctgaaaa agagaaaaaa atataaaatt tctggtgcac    4080
aggtttgttt tttcaagaaa attttgcaga agctatgttt ttaaagtgta cattttataa    4140
agtttatcag atattttcat atttaaagcc aaatgtaaat agaggtctgt aaagaaaaat    4200
aattgccata gaaagtataa tttcagtgca gtaatttctg agagctagta cctatatgct    4260
accggttagc atggttttag caaatatata ccagccttat aaggttcgta ttgctatgtt    4320
cttctgttat ttatttcagc atggactgtt catttgaaac cttttttctag ttattagcgt    4380 tttaacagtt acaagcttta aatggcaatt tttttttttt tttttttttt tttttttttt    4440
```

```
ttgtcaagag ccaagacaca ggtaatgcac gacattgatt gctgcatttt accttcaaaa    4500
tatttgtcct tattgactgg gtctccttaa ttaatgtaca catgtcatta gaatgcagac    4560 ggagggact caccatgaat atctggggtt gattcccaga tgtgtgttgc ttctctattg     4620
caagcagatt ccctgttgga tttacttcgg atttattccc ttttaaagaa ttttttgccca   4680 tatctggaag ggcactatat ttttgggagg agccatagat tcctggttat cctatttta    4740 aacaaaatgt agacaaagtg aactctattt tgattattga gaaggagta gttttctatc    4800 cctctaagag tatacttgaa tcagacattt taaggatgtc actatggcac tgttgtcatt    4860
tccaaattcc tagaaaagtt tgttttactt tgttttatt ctgttaatgc attcttctt    4920 ctctttactt cctttcttac cagtacactc ctatctcaac tctgtttatt tgatgagttc    4980
tgtcccgtaa atcatatttc ccttacaatt aataaatgtc acttcatatt ttataataaa    5040
ccactcagta aaagcaaaag cttgtcctga gaagtagagt gagttctttt tcactctgtg    5100
tctaataatg ttaaggtggg aaaaaaaaaa gtgtggcata gctacctgcc catccccaac    5160
cctcagcaaa gtagaatctc ttttctggta attttgggtt tccgctctgg gctctggcaa    5220
gttgaacaat cctagccatt gacaatcgtg atagttatta ttttcccatt tgctgtcttt    5280
ttgtatctaa agtcttccta ttgtactgca caaaccatgg attgtacata tttttatata    5340
ttatgtctta ttttattatt tctaaataaa aaaattaaaa attgaaaaaa aaaaaaa       5397
```

<210> SEQ ID NO 2
<211> LENGTH: 427
<212> TYPE: PRT
<213> ORGANISM: Homo sapiens

<400> SEQUENCE: 2

```
Met Gly Ser Val Arg Thr Asn Arg Tyr Ser Ile Val Ser Glu Glu
1               5                   10                  15

Asp Gly Met Lys Leu Ala Thr Met Ala Val Ala Asn Gly Phe Gly Asn
                20                  25                  30

Gly Lys Ser Lys Val His Thr Arg Gln Gln Cys Arg Ser Arg Phe Val
            35                  40                  45

Lys Lys Asp Gly His Cys Asn Val Gln Phe Ile Asn Val Gly Glu Lys
        50                  55                  60

Gly Gln Arg Tyr Leu Ala Asp Ile Phe Thr Thr Cys Val Asp Ile Arg
65                  70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu His Gly Asp
                100                 105                 110

Leu Asp Ala Ser Lys Glu Gly Lys Ala Cys Val Ser Glu Val Asn Ser
            115                 120                 125

Phe Thr Ala Ala Phe Leu Phe Ser Ile Glu Thr Gln Thr Thr Ile Gly
        130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
            180                 185                 190

Leu Val Phe Ser His Asn Ala Val Ile Ala Met Arg Asp Gly Lys Leu
        195                 200                 205
```

```
Cys Leu Met Trp Arg Val Gly Asn Leu Arg Lys Ser His Leu Val Glu
        210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
                260                 265                 270

Ile Asp Glu Asp Ser Pro Leu Tyr Asp Leu Ser Lys Gln Asp Ile Asp
            275                 280                 285

Asn Ala Asp Phe Glu Ile Val Val Ile Leu Glu Gly Met Val Glu Ala
        290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335

Tyr Lys Val Asp Tyr Ser Arg Phe His Lys Thr Tyr Glu Val Pro Asn
                340                 345                 350

Thr Pro Leu Cys Ser Ala Arg Asp Leu Ala Glu Lys Lys Tyr Ile Leu
            355                 360                 365

Ser Asn Ala Asn Ser Phe Cys Tyr Glu Asn Glu Val Ala Leu Thr Ser
        370                 375                 380

Lys Glu Glu Asp Asp Ser Gly Asn Gly Val Pro Glu Ser Thr Ser Thr
385                 390                 395                 400

Asp Thr Pro Pro Asp Ile Asp Leu His Asn Gln Ala Ser Val Pro Leu
                405                 410                 415

Glu Pro Arg Pro Leu Arg Arg Glu Ser Glu Ile
            420                 425

<210> SEQ ID NO 3
<211> LENGTH: 4273
<212> TYPE: DNA
<213> ORGANISM: Mus musculus

<400> SEQUENCE: 3
agagcgcact ggagccctgg ccagcgcgca gccttcccag caccggcaag cagggtcttg      60
ggaattctca cttgcttcgg ctcattctct ttcacaaaaa ccactggatc ttacatgctt     120
ctgtaatccc cacttccact ccatgtcccc atgatcctgt accagcaaca ggacaagttc     180
tctggatgtc agctgagtta ctaaggtaac tttgctggtc aaaagaaccc caaggttctc     240
ggaagcatcc atctctcctc attaataaat atatatatta attatatata tatataattt     300
tttttggtgt gtcttcaccg aacattcaaa actgtttctt ctaagggttt tgcaaaaact     360
cagactgttt tctaaagcag aaacactggc gtccccagcg aagcaatggg cagtgtgag      420
aaccaaccgc tacagcatcg tctcttcgga ggaagatggc atgaagctgg ccactatggc     480
agttgccaat ggctttggga tggcaagag taaagtccat acccgacaac agtgcaggag     540
ccgctttgtg aagaaagatg gtcattgcaa tgttcagttt atcaacgtgg gtgagaaggg     600
acagaggtac ctggcagaca tctttactac ctgtgtcgac atccgctgga ggtggatgct     660
ggttatcttc tgtcttgcct tcgtgctctc ctggctgttc tttggctgtg tgttttggtt     720
gatagccctg ctccatgggg atctagatac ttctaaagtg agcaaagcat gcgtgtcaga     780
ggtcaacagc ttcacggctg ccttcctctt tccatcgag acccagacaa ccattggcta     840
tggtttcagg tgtgtgacag acgagtgccc aattgctgtc ttcatggtgg tattccagtc     900
```

-continued

```
aatcgtaggc tgcatcattg acgccttcat cattggtgca gtcatggcga agatggcaaa      960
gccaaagaag agaaatgaga ctcttgtctt cagtcacaat gctgtgattg ccatgaggga     1020
tggcaaactc tgcttgatgt ggagagtggg taaccttcga aagagccacc ttgtggaagc     1080
tcatgtccgg gcacagcttc tcaaatctag gatcacttca aagggggagt atatcccttt     1140
ggaccagata gacatcaatg ttggttttga tagtggaatt gaccgcatat ttctagtgtc     1200
ccccatcact atcgttcacg aaatagatga agacagccct ttatatgact tgagtaagca     1260
ggacattgac aatgcagact ttgaaattgt tgtcatactg gaaggcatgg tggaggcgac     1320
tgccatgaca actcaatgcc ggagttcgta tctggccaat gaaattctct ggggtcaccg     1380
ctatgagcca gtgctctttg aagagaaaca ctactataaa gtagactatt caagattcca     1440
taagacttat gaagtaccta acacccccct ttgtagtgcc agagacttag cagagaagaa     1500
atacatcctt tcaaatgcaa attcattttg ctatgaaaat gaagttgccc taacaagcaa     1560
agaggaagag gaggatagtg agaacggagt cccagagagc acaagcacag actcacctcc     1620
tggcatagat ctccacaacc aggcaagcgt acctctagag cccaggccct aaggcgaga     1680 atcggagata tgactggctg attccgtctt tggaatactt actttgctac acagcctgac     1740
gttggtcaga ggtccgagac agttatacag accatggtac tggtcgagag gtgggtgaaa     1800
gcaagcagcc acaagagact aaggctagca caaaggtttc aaggaaagac taagctggat     1860
gactgatgta aagtgctttg caggcctcca agagacatga tggcacatat ctgttgtagt     1920
ataagttatg gggtttttaa tgtattgttt tgtgttttta caaaacttga atatgcaggc     1980
aagcctcagt ttgggtacat gacttacctg gaatgtttct ctttagggga acaagagtga     2040
ttttaatggc ataacacagg caagactctg ccttaatttt tgaaaagct gctaactaca     2100 tgaacacgaa ctgtattttt gttgcagtgt agtttatctt ttacataacg ttaagacgtc     2160
agtgttgagc attgttgaaa gcgcacagtg tgctttaaag catcaagtat ttggctatta     2220
actgccaaaa atgaaagcct gattttctga ggccagtaat ttgtttgcta aaaattgatc     2280
tctctgtcta cctgtcagtc tctgtctctg tctctctctc gttatctctc tctctctctc     2340
tctctctctc tctctcatta cataaatagca ttatataaca ctagccaaat ggtagcctct     2400
gggttttata cttttctttt ccacaatgct aataggttat ctcaaactttt cagttagacg     2460 accttaaatg aataccaaag ataatgcaca ttgttttgtt tttgttttttg tttttttctt     2520 tttcttttt tttctttcct ttttttttct tttttgcac atggaggtta tattttttta     2580
aaaagaaaca aaggctcctg cacagattgt cttggaaatc cagagacacc atctttgaac     2640
ttcagcaggg tgtgaagcag tccgttcatt tttgcactat agtctgaaaa gaacaccaaa     2700
gtctgatcaa tgtagtgtgt tttcgagtct gttcttttgt gcttctttct tatttggagg     2760
ggaggaggga agcataggtc acagttacat atgcactata atcaatattt ttttctttcc     2820 cttttttctga gcttttctct cttagcacat tccaaagttg gttccataag atcagatctt     2880
ggttgaactt tgttggtaac ctggcacctt ccaaactgtc acccagcagg gaagatgaac     2940
agatttcaaa ttttgcagct gactcatagc cttgactgcc agggcatttc tagctcagtg     3000
tcacattaag aaagatgtct ggcctctagt cttgtccttc taaggtctct gcagagatag     3060
agagagagag agagagagag agagagagag agagagagag agagagagac tttcaatgca     3120
gcaatccact ttacaggtga gagggaagtt tccttttttca tgacagaggg taagagggac     3180
tgtttcagta ttttaggtct tagtgagcca tataaacaca acataattac aagctaagga     3240
gttaagagtc taaagggtta tttctctctc tgtaaacatt catgattaat gccagtgggt     3300
```

```
-continued cattgtctct tggaaagtct cagagcacgt tgccaaggac tcattatttt ctagaagcct    3360
cttttaccta ttccacttcc tttataaaaa cctcccctccc tttcccaaac actagctcaa    3420
tcattcaatt ctccctccct tgtttctct tggttttaat gttctctact tgtaaaccct    3480
ggggctgctg agttcctttt tagttggcgt ctcaaaatca agcctctaat ggtattacac    3540
cctaatatgc cattaaaaat cagcttgttc tagaaccatg tattttattt aggttgatgt    3600
ttgtgccggt ctgtggcttg tgagcctctg tatctggata cagtgcctgt aagaaacgtt    3660
gacaatttct gctgttttca actttctaag tcaatggatt tgaaaactgt tggtgttatg    3720
gaaatcaaga gagaagcgtc gagaaagtgt acatctgggt tttaaggcag ggttgcaagt    3780
tgcttaaaga gtttgctggg ttggggacag ggagaagtca caggagagaa cacagactgg    3840
cttctgacag tgtgaggcta tggaaggctt cagatgctgc tattaaggtg atttgcaaag    3900
taaagtaatc aaaccaaaga gtattcagtg gaatgtcaat caaatgaaga tgcagtaaag    3960
agtgggggtg acaacatgga ctgaccccaa acacaaaaag acttgagtta tttgaaaaga    4020 gggaggggt gggtacagag acaagaaaag tgggagggga aatctttcaa ttttttttat    4080
ctttatttgc ttaaaaagaa gaaaccatct aaaatttctg gtgcatagat ttgttttcg    4140 tttgtttgtt tgttcgtttt ttttcttttt gttttcaag gaaaatttg cagaagcgac    4200 atttttaaag tgtacatttt ataaagttta tcagatattt tcatatttaa agccaaatgt    4260
aaatagaaat ctg                                                         4273
```

<210> SEQ ID NO 4
<211> LENGTH: 428
<212> TYPE: PRT
<213> ORGANISM: Mus musculus

<400> SEQUENCE: 4

```
Met Gly Ser Val Arg Thr Asn Arg Tyr Ser Ile Val Ser Ser Glu Glu
1               5                   10                  15

Asp Gly Met Lys Leu Ala Thr Met Ala Val Ala Asn Gly Phe Gly Asn
                20                  25                  30

Gly Lys Ser Lys Val His Thr Arg Gln Gln Cys Arg Ser Arg Phe Val
            35                  40                  45

Lys Lys Asp Gly His Cys Asn Val Gln Phe Ile Asn Val Gly Glu Lys
        50                  55                  60

Gly Gln Arg Tyr Leu Ala Asp Ile Phe Thr Thr Cys Val Asp Ile Arg
65                  70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu Leu His Gly Asp
                100                 105                 110

Leu Asp Thr Ser Lys Val Ser Lys Ala Cys Val Ser Glu Val Asn Ser
        115                 120                 125

Phe Thr Ala Ala Phe Leu Phe Ser Ile Glu Thr Gln Thr Thr Ile Gly
    130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
            180                 185                 190

Leu Val Phe Ser His Asn Ala Val Ile Ala Met Arg Asp Gly Lys Leu
        195                 200                 205
```

```
         Cys Leu Met Trp Arg Val Gly Asn Leu Arg Lys Ser His Leu Val Glu
             210                 215                 220

Ala His Val Arg Ala Gln Leu Leu Lys Ser Arg Ile Thr Ser Glu Gly
         225                 230                 235                 240

Glu Tyr Ile Pro Leu Asp Gln Ile Asp Ile Asn Val Gly Phe Asp Ser
                         245                 250                 255

Gly Ile Asp Arg Ile Phe Leu Val Ser Pro Ile Thr Ile Val His Glu
                     260                 265                 270

Ile Asp Glu Asp Ser Pro Leu Tyr Asp Leu Ser Lys Gln Asp Ile Asp
                 275                 280                 285

Asn Ala Asp Phe Glu Ile Val Val Ile Leu Glu Gly Met Val Glu Ala
         290                 295                 300

Thr Ala Met Thr Thr Gln Cys Arg Ser Ser Tyr Leu Ala Asn Glu Ile
         305                 310                 315                 320

Leu Trp Gly His Arg Tyr Glu Pro Val Leu Phe Glu Glu Lys His Tyr
                         325                 330                 335

Tyr Lys Val Asp Tyr Ser Arg Phe His Lys Thr Tyr Glu Val Pro Asn
                     340                 345                 350

Thr Pro Leu Cys Ser Ala Arg Asp Leu Ala Glu Lys Lys Tyr Ile Leu
                 355                 360                 365

Ser Asn Ala Asn Ser Phe Cys Tyr Glu Asn Glu Val Ala Leu Thr Ser
         370                 375                 380

Lys Glu Glu Glu Glu Asp Ser Glu Asn Gly Val Pro Glu Ser Thr Ser
         385                 390                 395                 400

Thr Asp Ser Pro Pro Gly Ile Asp Leu His Asn Gln Ala Ser Val Pro
                         405                 410                 415

Leu Glu Pro Arg Pro Leu Arg Arg Glu Ser Glu Ile
                     420                 425

<210> SEQ ID NO 5
<211> LENGTH: 2890
<212> TYPE: DNA
<213> ORGANISM: Homo sapiens

<400> SEQUENCE: 5
ctccgtccca ggggagaagg agaggcgtct gcaggggggca gagaccgcag ctacctgccg         60
ggtgcgcccc ccacccagga gcgctcgctt cgccccctttt cctcccccgc ccccacctcc        120
ttattggtgc tagtttgcag cgcccagctc ctgcgcctttc gcttcgcgtt tgaatctggc        180
tcgccccttc gtattatgtc tgcactccga aggaaatttg gggacgatta tcaggtagtg        240
accacatcgt ccagcggctc gggcttgcag ccccaggggc caggccagga ccctcagcag        300
cagcttgtgc caagaagaa gcggcagcgg ttcgtggaca agaacggccg gtgcaatgta         360
cagcacggca acctgggcag cgagacaagc cgctacctct cggacctctt caccacgctg        420
gtggacctca gtggcgctg gaacctcttc atcttcattc tcacctacac cgtggcctgg        480
cttttcatgg cgtccatgtg gtgggtgatc gcctacactc ggggcgacct gaacaaagcc        540
cacgtcggta actacacgcc ttgcgtggcc aatgtctata acttcccttc tgccttcctc        600
ttcttcatcg agacggaggc caccatcggc tatggctacc gatacatcac agacaagtgc        660
cccgagggca tcatcctctt cctcttccag tccatcctgg gctccatcgt ggacgccttc        720
ctcatcggct gcatgttcat caagatgtcc cagcccaaga gcgcgccga ccctcatg           780
```

```
ttcagcgagc acgcggtgat ctccatgagg gacggaaaac tcacgcttat gttccgggtg     840
ggcaacctgc gcaacagcca catggtctcc gcgcagattc gctgcaagct gctcaaatct     900
cggcagacac ctgagggtga gttccttccc cttgaccaac ttgaactgga tgtaggtttt     960
agtacagggg cagatcaact tttcttgtg tcccccctca caatttgcca cgtgatcgat    1020
gccaaaagcc ccttttatga cctatcccag cgaagcatgc aaactgaaca gttcgagatt    1080
gtcgtcatcc tagaaggcat tgtggaaaca actgggatga cttgtcaagc tcgaacatca    1140
tatactgaag atgaagttct ttggggtcat cgttttttc ctgtaatttc cttagaagag    1200
ggattcttta agttgatta ctcccagttc catgcaacat tgaagtccc caccccacct    1260 tacagtgtga aagagcagga ggaaatgctt ctcatgtcgt cccctttaat agcaccagcc    1320
ataactaaca gcaaagaaag acataattct gtggaatgct tagatggact agatgatatt    1380
actacaaaac taccatctaa gctgcagaaa attactggaa gagaagactt tcccaaaaaa    1440
ctcttgagga tgagttctac aacttcagaa aaagcctaca gcttgggaga cttgcccatg    1500
aaacttcaac gaataagttc agttccgggc aactcagaag aaaaactggt atctaaaacc    1560
accaagatgt tatctgatcc catgagccag tctgtggctg atttgccacc aaagcttcaa    1620
aagatggctg gaggagcagc taggatggaa gggaaccttc cagccaaatt aagaaaaatg    1680
aactctgatc gcttcacata acaaagcact cccttaggca ttatttaatg tttgatttag    1740
taatagtcca atatttggcg atgaggtaat tctccctaag gaatctgaaa gtatattttc    1800
ctcccagttc tacaagcata tttgagaacc cttccttcc caagtattgc gaatgtgcag    1860
aaagcaacag ttacggaggg aggacatcat aaggaagtta ttaacgggca tgtattatca    1920
catcaagcat gcaataatgt gcaaattttg catttagttt tatggcatga tttatatatg    1980
gcatatttat attgtatatt ctggaaaaaa aatatatata tatatttaaa ggggagatac    2040
tctccctgac atttctaaca tatgtattaa gccaaacatg agtgaatagc tttcagggcg    2100
ataaaactaa atatatgtct gtgtgtgtgt gtgtatgtat acacacatat acatatatat    2160
atacacatac atacacatac atacatacat acatatatat ctgataaaat tgtgatgttt    2220
tgttcaaagt tgtagttctt gtgcatgttt actttattag agtaggaagg ctactggcat    2280
taattattaa taccaaatat tttagcctta aattttgtc attttaaaat ctgatttaat    2340
gttttctgct gtttaaggtc ttgggaggct tcaattgta ttttatatga gagaatcaca    2400
caagtttgtg ctatctatgg ccctgcaaaa atataaccat tacatgttta aattgtaaat    2460
tttagagcat accagtactc agtatagcat tgaacatttc ttatgatttt taaaagttgc    2520
tagtactggg gagaaataat tgttgattaa tttgagaatt attcctttcc tagactaatt    2580
aaaatctgga aatctgtttt gtatatgatc taatacaaag atgagctctg aacaaacact    2640
gaatcatgtt aatagacagt agccaagtta tattgaatat atcagaatct gtgtgaagtt    2700
acacaattaa ttgtccctgt ttcaaactga gtaaattgga aacattttct ttcttttct    2760 ggaaattttg tccattttaa aaaccaatca ttttaagaag acatgacaat gcaatgaaac    2820
agatgataaa tatttatgct taaaatatgt atgtctaatt gagtctcttt tttattctgt    2880
tttcttgttt                                                           2890

<210> SEQ ID NO 6
<211> LENGTH: 501
<212> TYPE: PRT
<213> ORGANISM: Homo sapiens
```

```
<400> SEQUENCE: 6

Met Ser Ala Leu Arg Arg Lys Phe Gly Asp Asp Tyr Gln Val Val Thr
1               5                  10                  15

Thr Ser Ser Ser Gly Ser Gly Leu Gln Pro Gln Gly Pro Gly Gln Asp
            20                  25                  30

Pro Gln Gln Gln Leu Val Pro Lys Lys Arg Gln Arg Phe Val Asp
        35                  40                  45

Lys Asn Gly Arg Cys Asn Val Gln His Gly Asn Leu Gly Ser Glu Thr
    50                  55                  60

Ser Arg Tyr Leu Ser Asp Leu Phe Thr Thr Leu Val Asp Leu Lys Trp
65                  70                  75                  80

Arg Trp Asn Leu Phe Ile Phe Ile Leu Thr Tyr Thr Val Ala Trp Leu
                85                  90                  95

Phe Met Ala Ser Met Trp Trp Val Ile Ala Tyr Thr Arg Gly Asp Leu
            100                 105                 110

Asn Lys Ala His Val Gly Asn Tyr Thr Pro Cys Val Ala Asn Val Tyr
            115                 120                 125

Asn Phe Pro Ser Ala Phe Leu Phe Phe Ile Glu Thr Glu Ala Thr Ile
    130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
                165                 170                 175

Ile Gly Cys Met Phe Ile Lys Met Ser Gln Pro Lys Lys Arg Ala Glu
            180                 185                 190

Thr Leu Met Phe Ser Glu His Ala Val Ile Ser Met Arg Asp Gly Lys
            195                 200                 205

Leu Thr Leu Met Phe Arg Val Gly Asn Leu Arg Asn Ser His Met Val
    210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
                245                 250                 255

Thr Gly Ala Asp Gln Leu Phe Leu Val Ser Pro Leu Thr Ile Cys His
            260                 265                 270

Val Ile Asp Ala Lys Ser Pro Phe Tyr Asp Leu Ser Gln Arg Ser Met
            275                 280                 285

Gln Thr Glu Gln Phe Glu Ile Val Val Ile Leu Glu Gly Ile Val Glu
    290                 295                 300

Thr Thr Gly Met Thr Cys Gln Ala Arg Thr Ser Tyr Thr Glu Asp Glu
305                 310                 315                 320

Val Leu Trp Gly His Arg Phe Phe Pro Val Ile Ser Leu Glu Glu Gly
                325                 330                 335

Phe Phe Lys Val Asp Tyr Ser Gln Phe His Ala Thr Phe Glu Val Pro
            340                 345                 350

Thr Pro Pro Tyr Ser Val Lys Glu Gln Glu Glu Met Leu Leu Met Ser
            355                 360                 365

Ser Pro Leu Ile Ala Pro Ala Ile Thr Asn Ser Lys Glu Arg His Asn
    370                 375                 380

Ser Val Glu Cys Leu Asp Gly Leu Asp Asp Ile Thr Thr Lys Leu Pro
385                 390                 395                 400

Ser Lys Leu Gln Lys Ile Thr Gly Arg Glu Asp Phe Pro Lys Lys Leu
                405                 410                 415
```

Leu Arg Met Ser Ser Thr Thr Ser Glu Lys Ala Tyr Ser Leu Gly Asp
              420                 425                 430

Leu Pro Met Lys Leu Gln Arg Ile Ser Ser Val Pro Gly Asn Ser Glu
              435                 440                 445

Glu Lys Leu Val Ser Lys Thr Thr Lys Met Leu Ser Asp Pro Met Ser
450                 455                 460

Gln Ser Val Ala Asp Leu Pro Pro Lys Leu Gln Lys Met Ala Gly Gly
465                 470                 475                 480

Ala Ala Arg Met Glu Gly Asn Leu Pro Ala Lys Leu Arg Lys Met Asn
                  485                 490                 495

Ser Asp Arg Phe Thr
              500

<210> SEQ ID NO 7
<211> LENGTH: 2485
<212> TYPE: DNA
<213> ORGANISM: Homo sapiens

<400> SEQUENCE: 7

| | | | | | |
|---|---|---|---|---|---|
| tgagtagcat | tcattgaatc | tgcggatttc | atgacgtctc | tctgcgtggt | ccaccacttt | 60 |
| tctcctaacc | ggggattttt | tttttcttct | gccactctta | tctttcccca | cttcattcca | 120 |
| cccagtctcc | ctcccccgtc | cctgcccaaa | cgcgcgcccc | tccgccctc | ccttggcccc | 180 |
| agcgcccagc | cctgctctcc | gcgctcggcc | agagggagcc | agtccggaga | cggccgcacc | 240 |
| tggctggaga | ggctgggcgg | gcggaggggt | ggagacccgc | ggacgccggg | aagccggacc | 300 |
| tggagccgga | gcagccgcga | gcagaatgga | gtctcctaac | agcctctcgg | tgctgatgtg | 360 |
| aaatttgacc | atctgattcc | agtttttttc | ttttcctttt | cttttttgca | tttccttccc | 420 |
| tcgccatccg | tcgtgtagtg | aattgttcag | tcttgctccg | tttcaagaga | ggagatcatg | 480 |
| attgagtgaa | gccaccccgt | ccgcagccag | gaaaagcaca | agaagaaac | tgcaacaatg | 540 |
| gccaagctga | cagaatccat | gactaacgtc | ctggagggcg | actccatgga | tcaggacgtc | 600 |
| gaaagcccag | tggccattca | ccagccaaag | ttgcctaagc | aggccaggga | tgacctgcca | 660 |
| agacacatca | gccgagatcg | gaccaaaagg | aaaatccaga | ggtacgtgag | gaaagacgga | 720 |
| aagtgcaatg | ttcatcacgg | caacgtgagg | gagacctatc | gctacctgac | cgatatcttc | 780 |
| accacattag | tggacctgaa | gtggagattc | aacctattga | tttttgtcat | ggtttacaca | 840 |
| gtgacctggc | tctttttttgg | aatgatctgg | tggttgatcg | catacatacg | gggagacatg | 900 |
| gaccacatag | aggacccctc | ctggactcct | tgtgttacca | acctcaacgg | gttcgtctct | 960 |
| gcttttttat | tctcaataga | gacagaaacc | accattggtt | atggctaccg | ggtcatcaca | 1020 |
| gataaatgcc | agagggaat | tattcttctc | ttaatccaat | ctgtgttggg | gtccattgtc | 1080 |
| aatgcattca | tggtgggatg | catgtttgta | aaaatctctc | aacccaagaa | gagggcagag | 1140 |
| accctggtct | tttccaccca | tgcagtgatc | tccatgcggg | atgggaaact | gtgcctgatg | 1200 |
| ttccgggtag | gggaccttag | gaattcccac | attgtggagg | cttccatcag | agccaagttg | 1260 |
| atcaaatcca | aacagacctc | ggaggggag | ttcatcccgt | tgaaccagac | ggatatcaac | 1320 |
| gtagggtatt | acacggggga | tgaccgtctg | tttctggtgt | caccgctgat | cattagccat | 1380 |
| gaaattaacc | aacagagtcc | tttctgggag | atctccaaag | cccagctgcc | caaagaggaa | 1440 |
| ctggaaattg | tggtcatcct | agaaggaatg | gtggaagcca | cagggatgac | atgccaagct | 1500 |
| cgaagctcct | acatcaccag | tgagatcctg | tggggttacc | ggttcacacc | tgtcctgacc | 1560 |
| ctggaggacg | ggttctacga | agttgactac | aacagcttcc | atgagaccta | tgagaccagc | 1620 |

```
acccccatccc ttagtgccaa agagctggcc gagttagcca gcagggcaga gctgcccctg    1680
agttggtctg tatccagcaa actcaaccaa catgcagaac tggagactga agaggaagaa    1740
aagaacctcg aagagcaaac agaaagaaat ggtgatgtgg caaacctgga gaatgaatcc    1800
aaagtttagt gccctagctg ggcaaaccct tctcttctcc ccccaacaca atctttcctt    1860
gtctctcatt ctctttcttt ttctgtctct cttgctttgt tctttatttg tttatattta    1920 attttttacat gaccagaaaa caaatcttca aggtgtaaaa tatctacctg ccctctctca    1980
gttattcaga ttgacaaggt agacatggat ttgatgaaag tgcaaagtgc cctcatttgt    2040
ggcccaagcc tggtctcctc ccaaaatact acacatccaa ctcctggaga tttcagttac    2100
ttacctgcat gtgttgtaca ataccagatc actcaaaaag gtgtgtcaaa gattttacct    2160
gggatatgac aagcaaggtt tctggtgcct atttattcat tcagtgagac acagagtgga    2220
gccctcagtt ttatggatcc caattcattt catctactac agggtgaggt gcttgccccc    2280
atgtgggtgt ggcagttaca gggcccaggt gagctgaaga caaaccactg tacatatata    2340
tgccttatgt aattattttc tttttgtaat tagtaataaa acccagcatg tacaaaagta    2400
ccatagaaca gaactgctaa atactgtaca tagatgtatc attaatgtag gtttagatat    2460
ataactttag aaataagaag caaaa                                          2485
```

<210> SEQ ID NO 8
<211> LENGTH: 423
<212> TYPE: PRT
<213> ORGANISM: Homo sapiens

<400> SEQUENCE: 8

```
Met Ala Lys Leu Thr Glu Ser Met Thr Asn Val Leu Glu Gly Asp Ser
1               5                   10                  15

Met Asp Gln Asp Val Glu Ser Pro Val Ala Ile His Gln Pro Lys Leu
            20                  25                  30

Pro Lys Gln Ala Arg Asp Asp Leu Pro Arg His Ile Ser Arg Asp Arg
        35                  40                  45

Thr Lys Arg Lys Ile Gln Arg Tyr Val Arg Lys Asp Gly Lys Cys Asn
    50                  55                  60

Val His His Gly Asn Val Arg Glu Thr Tyr Arg Tyr Leu Thr Asp Ile
65                  70                  75                  80

Phe Thr Thr Leu Val Asp Leu Lys Trp Arg Phe Asn Leu Leu Ile Phe
                85                  90                  95

Val Met Val Tyr Thr Val Thr Trp Leu Phe Phe Gly Met Ile Trp Trp
            100                 105                 110

Leu Ile Ala Tyr Ile Arg Gly Asp Met Asp His Ile Glu Asp Pro Ser
        115                 120                 125

Trp Thr Pro Cys Val Thr Asn Leu Asn Gly Phe Val Ser Ala Phe Leu
    130                 135                 140

Phe Ser Ile Glu Thr Glu Thr Thr Ile Gly Tyr Gly Tyr Arg Val Ile
145                 150                 155                 160

Thr Asp Lys Cys Pro Glu Gly Ile Ile Leu Leu Leu Ile Gln Ser Val
                165                 170                 175

Leu Gly Ser Ile Val Asn Ala Phe Met Val Gly Cys Met Phe Val Lys
            180                 185                 190

Ile Ser Gln Pro Lys Lys Arg Ala Glu Thr Leu Val Phe Ser Thr His
        195                 200                 205

Ala Val Ile Ser Met Arg Asp Gly Lys Leu Cys Leu Met Phe Arg Val
    210                 215                 220
```

```
Gly Asp Leu Arg Asn Ser His Ile Val Glu Ala Ser Ile Arg Ala Lys
225                 230                 235                 240

Leu Ile Lys Ser Lys Gln Thr Ser Glu Gly Glu Phe Ile Pro Leu Asn
            245                 250                 255

Gln Thr Asp Ile Asn Val Gly Tyr Tyr Thr Gly Asp Asp Arg Leu Phe
        260                 265                 270

Leu Val Ser Pro Leu Ile Ile Ser His Glu Ile Asn Gln Gln Ser Pro
    275                 280                 285

Phe Trp Glu Ile Ser Lys Ala Gln Leu Pro Lys Glu Glu Leu Glu Ile
290                 295                 300

Val Val Ile Leu Glu Gly Met Val Glu Ala Thr Gly Met Thr Cys Gln
305                 310                 315                 320

Ala Arg Ser Ser Tyr Ile Thr Ser Glu Ile Leu Trp Gly Tyr Arg Phe
                325                 330                 335

Thr Pro Val Leu Thr Leu Glu Asp Gly Phe Tyr Glu Val Asp Tyr Asn
            340                 345                 350

Ser Phe His Glu Thr Tyr Glu Thr Ser Thr Pro Ser Leu Ser Ala Lys
        355                 360                 365

Glu Leu Ala Glu Leu Ala Ser Arg Ala Glu Leu Pro Leu Ser Trp Ser
370                 375                 380

Val Ser Ser Lys Leu Asn Gln His Ala Glu Leu Glu Thr Glu Glu Glu
385                 390                 395                 400

Glu Lys Asn Leu Glu Glu Gln Thr Glu Arg Asn Gly Asp Val Ala Asn
                405                 410                 415

Leu Glu Asn Glu Ser Lys Val
            420

<210> SEQ ID NO 9
<211> LENGTH: 2912
<212> TYPE: DNA
<213> ORGANISM: Homo sapiens

<400> SEQUENCE: 9
acacacacac acacacacac acacagagag agagagagag agagagagag agagagagat      60
tgttccagct gctctcgcta gagaaaggga gtgacccaag gggccgcgag tgaagggaca     120
ggatggctta ggtacctctg cccacaggac cccacaacag ggagaggttc cagctacagc     180
tcctccgtgg ggtcatggca ggggctgggg agtcccctca aaagccctga gccccctgc     240
accgccgcta agggacaccc cagaagttag catcagtggg actcggaagc tccgatctca     300
acaacatccc agctatggct ggcgattcta ggaatgccat gaaccaggac atggagattg     360
gagtcactcc ctgggacccc aagaagattc aaaacaggc cgcgattat gtccccattg       420
ccacagaccg tacgcgcctg ctggccgagg gcaagaagcc acgccagcgc tacatggaga     480
agagtggcaa gtgcaacgtg caccacggca acgtccagga gacctaccgg tacctgagtg     540
acctcttcac caccctggtg gacctcaagt ggcgcttcaa cttgctcgtc ttcaccatgg     600
tttacactgt cacctggctg ttcttcggct tcatttggtg gctcattgct tatatccggg     660
gtgacctgga ccatgttggc gaccaagagt ggattccttg tgttgaaaac ctcagtggct     720
tcgtgtccgc tttcctgttc tccattgaga ccgaaacaac cattgggtat ggcttccgag     780
tcatcacaga gaagtgtcca gaggggatta tactcctctt ggtccaggcc atcctgggct     840
ccatcgtcaa tgccttcatg gtggggtgca tgtttgtcaa gatcagccag cccaagaaga     900
gagcggagac cctcatgttt tccaacaacg cagtcatctc catgcgggac gagaagctgt     960
gcctcatgtt ccgggtgggc gacctccgca actcccacat cgtggaggcc tccatccggg    1020
```

```
ccaagctcat caagtcccgg cagaccaaag agggggagtt catcccctg aaccagacag    1080 acatcaacgt gggctttgac acgggcgacg accgcctctt ccttgtgtct cctctgatca    1140
tctcccatga gatcaaccag aagagccctt tctgggagat gtctcaggct cagctgcatc    1200
aggaagagtt tgaagttgtg gtcattctag aagggatggt ggaagccaca ggcatgacct    1260
gccaagcccg gagctcctac atggatacag aggtgctctg gggccaccga ttcacaccag    1320
tcctcacctt ggaaaagggc ttctatgagg tggactacaa caccttccat gatacctatg    1380
agaccaacac acccagctgc tgtgccaagg agctggcaga aatgaagagg aaggccggc    1440 tcctccagta cctccccagc cccccactgc tgggggctg tgctgaggca gggctggatg    1500
cagaggctga gcagaatgaa gaagatgagc ccaaggggct gggtgggtcc agggaggcca    1560
ggggctcggt gtgaggggtg cagcctccct aagacctcct gtcactggct tcagtgaaca    1620
cagacactgc agagcctggg agcaggggag gggaatagtt gagtgtgctg tttgggggct    1680
caggagccat caaggctgtg gggaggaacc ataaacccag ccctcacagc tcccagcaca    1740
gggcctccct gagccagtgg catcctgcct gggccccca tggcagtgct gcctcttgta    1800
ggtgctggct aagggccagg ccaggatgag tttccccatg gtgaatgtta ccggatggca    1860
tctgttctct ccatgccctg ggtcacttcc ttttttgggt ctcacagacc cctccagggg    1920
ctgacaccta gagagaacca tcaccttgtc cctcattcct tccaccctga ggcttgctgt    1980
ggactcagag aggagactta cctgatgaga gctcaaacct ctagtctggg atgagctcac    2040
agagccctca tgagttaaga tccatccata tcacataggc aattccttt aaatcagata    2100 ccaacgaccc attactgaga ggtacagagc gtacagccct tggtgttctc tgctgttatc    2160
tgccaaatgt gtgtgttttt cctctgctgt gttctgtgtg tccagtgtag cctattggag    2220
aatcggtctc attagagtga ctcttagaag gtggcctggg actagacagc ccctctgagc    2280
acatgcatag tggcatcagc agcttcctgg cctactccca atcacactgt gccctgcacc    2340
tcccaccaag ggggaacccc agcagctggg gcttttcgag tgcttttgg cccaagaatc    2400 tcagagtgct tctaatcatc acagtagttt ttgtgttttg ttttgttttg ttttgttttg    2460
ttttgttttg ttttgttttt ttcacaatct cagccagcct gcggtgtgac ctggggagaa    2520
agttgagtgt caggggacat gatgagccag ttggccctga acaggaatg gggcaaagag    2580 aaaggagagc caggagcatt taaaaatcag catctgggcc aggcaagatg gctcacgcct    2640
gtgatcccag catttggga ggccgaggcg ggtggatcat gaggtcagga gatcgagacc    2700
atcctggcta acacggtgaa accccgtctc tactgaaaat acaaaaaatt agccaggcat    2760
ggtggcaggt gcctgtagtc ccagctactc gggaagctga ggcagaagaa tggcatgaac    2820
ctgggaggtg gaggttgcag tgagccaaga tcatgccact gcactccagc ctgggcgaca    2880
gagcgagact ccatctcaaa aaaaaaaaa ac                                   2912
```

<210> SEQ ID NO 10
<211> LENGTH: 419
<212> TYPE: PRT
<213> ORGANISM: Homo sapiens

<400> SEQUENCE: 10

Met Ala Gly Asp Ser Arg Asn Ala Met Asn Gln Asp Met Glu Ile Gly
1               5                   10                  15

Val Thr Pro Trp Asp Pro Lys Lys Ile Pro Lys Gln Ala Arg Asp Tyr
            20                  25                  30

Val Pro Ile Ala Thr Asp Arg Thr Arg Leu Leu Ala Glu Gly Lys Lys
        35                  40                  45

Pro Arg Gln Arg Tyr Met Glu Lys Ser Gly Lys Cys Asn Val His His
 50                  55                  60

Gly Asn Val Gln Glu Thr Tyr Arg Tyr Leu Ser Asp Leu Phe Thr Thr
 65                  70                  75                  80

Leu Val Asp Leu Lys Trp Arg Phe Asn Leu Leu Val Phe Thr Met Val
                 85                  90                  95

Tyr Thr Val Thr Trp Leu Phe Phe Gly Phe Ile Trp Trp Leu Ile Ala
            100                 105                 110

Tyr Ile Arg Gly Asp Leu Asp His Val Gly Asp Gln Glu Trp Ile Pro
            115                 120                 125

Cys Val Glu Asn Leu Ser Gly Phe Val Ser Ala Phe Leu Phe Ser Ile
130                 135                 140

Glu Thr Glu Thr Thr Ile Gly Tyr Gly Phe Arg Val Ile Thr Glu Lys
145                 150                 155                 160

Cys Pro Glu Gly Ile Ile Leu Leu Leu Val Gln Ala Ile Leu Gly Ser
                165                 170                 175

Ile Val Asn Ala Phe Met Val Gly Cys Met Phe Val Lys Ile Ser Gln
            180                 185                 190

Pro Lys Lys Arg Ala Glu Thr Leu Met Phe Ser Asn Asn Ala Val Ile
            195                 200                 205

Ser Met Arg Asp Glu Lys Leu Cys Leu Met Phe Arg Val Gly Asp Leu
210                 215                 220

Arg Asn Ser His Ile Val Glu Ala Ser Ile Arg Ala Lys Leu Ile Lys
225                 230                 235                 240

Ser Arg Gln Thr Lys Glu Gly Glu Phe Ile Pro Leu Asn Gln Thr Asp
                245                 250                 255

Ile Asn Val Gly Phe Asp Thr Gly Asp Asp Arg Leu Phe Leu Val Ser
            260                 265                 270

Pro Leu Ile Ile Ser His Glu Ile Asn Gln Lys Ser Pro Phe Trp Glu
            275                 280                 285

Met Ser Gln Ala Gln Leu His Gln Glu Glu Phe Glu Val Val Val Ile
290                 295                 300

Leu Glu Gly Met Val Glu Ala Thr Gly Met Thr Cys Gln Ala Arg Ser
305                 310                 315                 320

Ser Tyr Met Asp Thr Glu Val Leu Trp Gly His Arg Phe Thr Pro Val
                325                 330                 335

Leu Thr Leu Glu Lys Gly Phe Tyr Glu Val Asp Tyr Asn Thr Phe His
            340                 345                 350

Asp Thr Tyr Glu Thr Asn Thr Pro Ser Cys Cys Ala Lys Glu Leu Ala
            355                 360                 365

Glu Met Lys Arg Glu Gly Arg Leu Leu Gln Tyr Leu Pro Ser Pro Pro
370                 375                 380

Leu Leu Gly Gly Cys Ala Glu Ala Gly Leu Asp Ala Glu Ala Glu Gln
385                 390                 395                 400

Asn Glu Glu Asp Glu Pro Lys Gly Leu Gly Gly Ser Arg Glu Ala Arg
                405                 410                 415

Gly Ser Val

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 11

Asp Tyr Lys Asp Asp Asp Lys Gly
1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Lys Pro Ile Pro Asn Pro Leu Leu Gly Leu Asp Ser Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Gln Lys Leu Ile Ser Glu Glu Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Pro Glu Leu Ala Pro Glu Asp Pro Glu Asp
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Pro Tyr Asp Val Pro Asp Tyr Ala
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Thr Asp Ile Glu Met Asn Arg Leu Gly Lys
1               5                   10

<210> SEQ ID NO 17
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 17

His His His His His His
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 18

His His His His His His His His
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid; This region may encompass 1-3
      residues

<400> SEQUENCE: 19

Cys Cys Xaa Xaa Xaa Cys Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Cys Pro Gly Cys Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Pro Arg Gly Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Asp Asp Asp Asp Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Asn Leu Tyr Phe Gln Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Glu Val Leu Phe Gln Gly Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Leu Arg Lys Ser His Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Leu Arg Asn Ser His Leu
1               5

<210> SEQ ID NO 27
<211> LENGTH: 22
<212> TYPE: PRT
<213> ORGANISM: Rattus sp.

<400> SEQUENCE: 27

Gln Gln Cys Arg Ser Arg Phe Val Lys Lys Asp Gly His Cys Asn Val
1               5                   10                  15

Gln Phe Ile Asn Val Gly
            20

<210> SEQ ID NO 28
<211> LENGTH: 16
<212> TYPE: PRT
<213> ORGANISM: Rattus sp.
```

-continued

<400> SEQUENCE: 28

Gln Leu Leu Lys Ser Arg Ile Thr Ser Glu Gly Glu Tyr Ile Pro Leu
1               5                   10                  15

<210> SEQ ID NO 29
<211> LENGTH: 16
<212> TYPE: PRT
<213> ORGANISM: Rattus sp.

<400> SEQUENCE: 29

Tyr Glu Pro Val Leu Phe Glu Glu Lys His Tyr Tyr Lys Val Asp Tyr
1               5                   10                  15

<210> SEQ ID NO 30
<211> LENGTH: 22
<212> TYPE: PRT
<213> ORGANISM: Rattus sp.

<400> SEQUENCE: 30

Lys Arg Lys Ile Gln Arg Tyr Val Arg Lys Asp Gly Lys Cys Asn Val
1               5                   10                  15

His His Gly Asn Val Arg
            20

<210> SEQ ID NO 31
<211> LENGTH: 16
<212> TYPE: PRT
<213> ORGANISM: Rattus sp.

<400> SEQUENCE: 31

Lys Leu Ile Lys Ser Lys Gln Thr Ser Glu Gly Glu Phe Ile Pro Leu
1               5                   10                  15

<210> SEQ ID NO 32
<211> LENGTH: 16
<212> TYPE: PRT
<213> ORGANISM: Rattus sp.

<400> SEQUENCE: 32

Phe Thr Pro Val Leu Thr Leu Glu Asp Gly Phe Tyr Glu Val Asp Tyr
1               5                   10                  15

<210> SEQ ID NO 33
<211> LENGTH: 11
<212> TYPE: PRT
<213> ORGANISM: Rattus sp.

<400> SEQUENCE: 33

Arg Val Gly Asn Leu Arg Lys Ser His Leu Val
1               5                   10

<210> SEQ ID NO 34
<211> LENGTH: 19
<212> TYPE: PRT
<213> ORGANISM: Rattus sp.

<400> SEQUENCE: 34

Ile Leu Glu Gly Met Val Glu Ala Thr Ala Met Thr Thr Gln Cys Arg
1               5                   10                  15

Ser Ser Tyr

```
<210> SEQ ID NO 35
<211> LENGTH: 9
<212> TYPE: PRT
<213> ORGANISM: Rattus sp.

<400> SEQUENCE: 35

Leu Phe Glu Glu Lys His Tyr Tyr Lys
1               5

<210> SEQ ID NO 36
<211> LENGTH: 161
<212> TYPE: PRT
<213> ORGANISM: Rattus sp.

<400> SEQUENCE: 36

Arg Arg Trp Phe Ile Thr His Ile Phe Gly Arg Ser Arg Gln Arg Ala
1               5                   10                  15

Arg Leu Val Ser Lys Glu Gly Arg Cys Asn Ile Glu Phe Gly Asn Val
            20                  25                  30

Asp Ala Gln Ser Arg Phe Ile Phe Val Asp Ile Trp Cys Val Glu
        35                  40                  45

Asn Ile Asn Gly Met Thr Ser Ala Phe Leu Phe Ser Leu Glu Thr Gln
 50                  55                  60

Val Thr Ile Gly Tyr Gly Phe Arg Phe Val Thr Glu Gln Cys Ala Thr
65                  70                  75                  80

Ala Tyr Gly Lys Leu Leu Lys Thr Thr Ile Thr Pro Glu Gly Glu Thr
                85                  90                  95

Ile Ile Leu Asp Gln Thr Asn Ile Asn Phe Val Val Asp Ala Gly Asn
            100                 105                 110

Glu Asn Leu Phe Phe Ile Ser Pro Leu Ala Thr Cys Gln Val Arg Thr
        115                 120                 125

Ser Tyr Val Pro Glu Glu Val Leu Trp Gly Tyr Arg Phe Val Pro Ile
    130                 135                 140

Val Ser Lys Thr Lys Glu Gly Lys Tyr Arg Val Asp Phe His Asn Phe
145                 150                 155                 160

Gly

<210> SEQ ID NO 37
<211> LENGTH: 158
<212> TYPE: PRT
<213> ORGANISM: Rattus sp.

<400> SEQUENCE: 37

Gly Asn Gly Lys Ser Lys Val His Thr Arg Gln Gln Cys Arg Ser Arg
1               5                   10                  15

Phe Val Lys Lys Asp Gly His Cys Asn Val Gln Phe Ile Asn Val Gly
            20                  25                  30

Glu Lys Gly Gln Arg Tyr Leu Ala Asp Ile Phe Cys Val Ser Glu Val
        35                  40                  45

Asn Ser Phe Thr Ala Ala Phe Leu Phe Ser Ile Glu Thr Gln Thr Thr
 50                  55                  60

Ile Gly Tyr Gly Phe Arg Cys Val Thr Asp Glu Cys Pro Ile Ala Arg
65                  70                  75                  80

Ala Gln Leu Leu Lys Ser Arg Ile Thr Ser Glu Gly Glu Tyr Ile Pro
                85                  90                  95

Leu Asp Gln Ile Asp Ile Asn Val Gly Phe Asp Ser Gly Ile Asp Arg
            100                 105                 110
```

```
Ile Phe Leu Val Ser Pro Ile Met Thr Thr Gln Cys Arg Ser Ser Tyr
        115                 120                 125

Leu Ala Asn Glu Ile Leu Trp Gly His Arg Tyr Glu Pro Val Leu Phe
        130                 135                 140

Glu Glu Lys His Cys Tyr Lys Val Asp Tyr Ser Arg Phe His
145                 150                 155

<210> SEQ ID NO 38
<211> LENGTH: 156
<212> TYPE: PRT
<213> ORGANISM: Rattus sp.

<400> SEQUENCE: 38

Gly Asn Gly Lys Val His Thr Arg Arg Cys Arg Asn Arg Phe Val
1               5                   10                  15

Lys Lys Asn Gly Gln Cys Asn Ile Glu Phe Ala Asn Met Asp Glu Lys
                20                  25                  30

Ser Gln Arg Tyr Leu Ala Asp Met Phe Cys Val Leu Gln Val His Gly
        35                  40                  45

Phe Met Ala Ala Phe Leu Phe Ser Ile Glu Thr Gln Thr Thr Ile Gly
50                  55                  60

Tyr Gly Leu Arg Cys Val Thr Glu Glu Cys Pro Val Ala Arg Ala Gln
65                  70                  75                  80

Leu Ile Lys Pro Arg Val Thr Glu Glu Gly Tyr Ile Pro Leu Asp
                85                  90                  95

Gln Ile Asp Ile Asp Val Gly Phe Asp Lys Gly Leu Asp Arg Ile Phe
            100                 105                 110

Leu Val Ser Pro Ile Met Thr Thr Gln Ala Arg Ser Ser Tyr Leu Ala
        115                 120                 125

Asn Glu Ile Leu Trp Gly His Arg Phe Glu Pro Val Leu Phe Glu Glu
    130                 135                 140

Lys Asn Gln Tyr Lys Ile Asp Tyr Ser His Phe His
145                 150                 155

<210> SEQ ID NO 39
<211> LENGTH: 157
<212> TYPE: PRT
<213> ORGANISM: Rattus sp.

<400> SEQUENCE: 39

Arg Asn Gly Gln Ala His Val Pro Arg Arg Lys Arg Asn Arg Phe
1               5                   10                  15

Val Lys Lys Asn Gly Gln Cys Asn Val Tyr Phe Ala Asn Leu Ser Asn
                20                  25                  30

Lys Ser Gln Arg Tyr Met Ala Asp Ile Phe Cys Ile Met His Val Asn
        35                  40                  45

Gly Phe Leu Gly Ala Phe Leu Phe Ser Val Glu Thr Gln Thr Thr Ile
50                  55                  60

Gly Tyr Gly Phe Arg Cys Val Thr Glu Glu Cys Pro Leu Ala Arg Ala
65                  70                  75                  80

Gln Leu Ile Lys Pro Tyr Met Thr Gln Glu Gly Glu Tyr Leu Pro Leu
                85                  90                  95

Asp Gln Arg Asp Leu Asn Val Gly Tyr Asp Ile Gly Leu Asp Arg Ile
            100                 105                 110

Phe Leu Val Ser Pro Ile Met Thr Thr Gln Ala Arg Ser Ser Tyr Leu
        115                 120                 125
```

Ala Ser Glu Ile Leu Trp Gly His Arg Phe Glu Pro Val Val Phe Glu
130                 135                 140

Glu Lys Ser His Tyr Lys Val Asp Tyr Ser Arg Phe His
145                 150                 155

<210> SEQ ID NO 40
<211> LENGTH: 158
<212> TYPE: PRT
<213> ORGANISM: Rattus sp.

<400> SEQUENCE: 40

Gly Gln Gly Pro Gln Gln Gln Leu Val Pro Lys Lys Arg Gln Arg
1               5                   10                  15

Phe Val Asp Lys Asn Gly Arg Cys Asn Val Gln His Gly Asn Leu Gly
                20                  25                  30

Ser Glu Thr Ser Arg Tyr Leu Ser Asp Leu Phe Cys Val Ala Asn Val
            35                  40                  45

Tyr Asn Phe Pro Ser Ala Phe Leu Phe Phe Ile Glu Thr Glu Ala Thr
50                  55                  60

Ile Gly Tyr Gly Tyr Arg Tyr Ile Thr Asp Lys Cys Pro Glu Gly Arg
65                  70                  75                  80

Cys Lys Leu Leu Lys Ser Arg Gln Thr Pro Glu Gly Glu Phe Leu Pro
                85                  90                  95

Leu Asp Gln Leu Glu Leu Asp Val Gly Phe Ser Thr Gly Ala Asp Gln
            100                 105                 110

Leu Phe Leu Val Ser Pro Leu Met Thr Cys Gln Ala Arg Thr Ser Tyr
        115                 120                 125

Thr Glu Asp Glu Val Leu Trp Gly His Arg Phe Phe Pro Val Ile Ser
130                 135                 140

Leu Glu Glu Gly Phe Phe Lys Val Asp Tyr Ser Gln Phe His
145                 150                 155

<210> SEQ ID NO 41
<211> LENGTH: 159
<212> TYPE: PRT
<213> ORGANISM: Rattus sp.

<400> SEQUENCE: 41

Asp Asp Leu Pro Arg His Ile Ser Arg Asp Arg Thr Lys Arg Lys Ile
1               5                   10                  15

Gln Arg Tyr Val Arg Lys Asp Gly Lys Cys Asn Val His His Gly Asn
                20                  25                  30

Val Arg Glu Thr Tyr Arg Tyr Leu Thr Asp Ile Phe Cys Val Thr Asn
            35                  40                  45

Leu Asn Gly Phe Val Ser Ala Phe Leu Phe Ser Ile Glu Thr Glu Thr
50                  55                  60

Thr Ile Gly Tyr Gly Tyr Arg Val Ile Thr Asp Lys Cys Pro Glu Gly
65                  70                  75                  80

Arg Ala Lys Leu Ile Lys Ser Lys Gln Thr Ser Glu Gly Glu Phe Ile
                85                  90                  95

Pro Leu Asn Gln Thr Asp Ile Asn Val Gly Tyr Tyr Thr Gly Asp Asp
            100                 105                 110

Arg Leu Phe Leu Val Ser Pro Leu Met Thr Cys Gln Ala Arg Ser Ser
        115                 120                 125

```
Tyr Val Thr Ser Glu Ile Leu Trp Gly Tyr Arg Phe Thr Pro Val Leu
            130                 135                 140

Thr Leu Glu Asp Gly Phe Tyr Glu Val Asp Tyr Asn Ser Phe His
145                 150                 155
```

<210> SEQ ID NO 42
<211> LENGTH: 158
<212> TYPE: PRT
<213> ORGANISM: Rattus sp.

<400> SEQUENCE: 42

```
Ala Phe Ser Pro Gly Ser Glu Pro Pro Arg Arg Gly Arg Gln
1               5                   10                  15

Arg Tyr Val Glu Lys Asp Gly Arg Cys Asn Val Gln Gln Gly Asn Val
                20                  25                  30

Arg Glu Thr Tyr Arg Tyr Leu Thr Asp Leu Phe Cys Val Asn Asn Leu
            35                  40                  45

Asn Gly Phe Val Ala Ala Phe Leu Phe Ser Ile Glu Thr Glu Thr Thr
50                  55                  60

Ile Gly Tyr Gly His Arg Val Ile Thr Asp Gln Cys Pro Glu Gly Arg
65                  70                  75                  80

Ala Lys Leu Ile Arg Ser Arg Gln Thr Leu Glu Gly Glu Phe Ile Pro
                85                  90                  95

Leu His Gln Thr Asp Leu Ser Val Gly Phe Asp Thr Gly Asp Asp Arg
            100                 105                 110

Leu Phe Leu Val Ser Pro Leu Met Thr Cys Gln Ala Arg Ser Ser Tyr
            115                 120                 125

Leu Val Asp Glu Val Leu Trp Gly His Arg Phe Thr Ser Val Leu Thr
            130                 135                 140

Leu Glu Asp Gly Phe Tyr Glu Val Asp Tyr Ala Ser Phe His
145                 150                 155
```

<210> SEQ ID NO 43
<211> LENGTH: 163
<212> TYPE: PRT
<213> ORGANISM: Rattus sp.

<400> SEQUENCE: 43

```
Asp Tyr Ile Pro Ile Ala Thr Asp Arg Thr Arg Leu Leu Pro Glu Gly
1               5                   10                  15

Lys Lys Pro Arg Gln Arg Tyr Met Glu Lys Thr Gly Lys Cys Asn Val
                20                  25                  30

His His Gly Asn Val Gln Glu Thr Tyr Arg Tyr Leu Ser Asp Leu Phe
            35                  40                  45

Cys Val Glu Asn Leu Ser Gly Phe Val Ser Ala Phe Leu Phe Ser Ile
50                  55                  60

Glu Thr Glu Thr Thr Ile Gly Tyr Gly Phe Arg Val Ile Thr Glu Lys
65                  70                  75                  80

Cys Pro Glu Gly Arg Ala Lys Leu Ile Lys Ser Arg Gln Thr Lys Glu
                85                  90                  95

Gly Glu Phe Ile Pro Leu Asn Gln Thr Asp Ile Asn Val Gly Phe Asp
            100                 105                 110

Thr Gly Asp Asp Arg Leu Phe Leu Val Ser Pro Leu Met Thr Cys Gln
            115                 120                 125
```

Ala Arg Ser Ser Tyr Met Asp Thr Glu Val Leu Trp Gly His Arg Phe
            130                 135                 140

Thr Pro Val Leu Thr Leu Glu Lys Gly Phe Tyr Glu Val Asp Tyr Asn
145                 150                 155                 160

Thr Phe His

<210> SEQ ID NO 44
<211> LENGTH: 156
<212> TYPE: PRT
<213> ORGANISM: Rattus sp.

<400> SEQUENCE: 44

Ser Arg Pro Leu Val Ala Pro Gly Ile Arg Arg Arg Val Leu Thr
1               5                   10                  15

Lys Asp Gly Arg Ser Asn Val Arg Met Glu His Ile Ala Asp Lys Arg
            20                  25                  30

Phe Leu Tyr Leu Lys Asp Leu Trp Cys Val Val Gln Val His Thr Leu
        35                  40                  45

Thr Gly Ala Phe Leu Phe Ser Leu Glu Ser Gln Thr Thr Ile Gly Tyr
    50                  55                  60

Gly Phe Arg Tyr Ile Ser Glu Glu Cys Pro Leu Ala Thr Gly Lys Leu
65                  70                  75                  80

Leu Gln Thr His Gln Thr Lys Glu Gly Glu Asn Ile Arg Leu Asn Gln
                85                  90                  95

Val Asn Val Thr Phe Gln Val Asp Thr Ala Ser Asp Ser Pro Phe Leu
            100                 105                 110

Ile Leu Pro Leu Ala Thr Cys Gln Val Arg Thr Ser Tyr Leu Pro Glu
        115                 120                 125

Glu Ile Leu Trp Gly Tyr Glu Phe Thr Pro Ala Ile Ser Leu Ser Ala
    130                 135                 140

Ser Gly Lys Tyr Val Ala Asp Phe Ser Leu Phe Asp
145                 150                 155

<210> SEQ ID NO 45
<211> LENGTH: 156
<212> TYPE: PRT
<213> ORGANISM: Rattus sp.

<400> SEQUENCE: 45

His Thr Asn Gly Val Gly Leu Lys Ala His Arg Pro Arg Val Met Ser
1               5                   10                  15

Lys Ser Gly His Ser Asn Val Arg Ile Asp Lys Val Asp Gly Ile Tyr
            20                  25                  30

Leu Leu Tyr Leu Gln Asp Leu Trp Cys Ile Met Lys Val Asp Ser Leu
        35                  40                  45

Thr Gly Ala Phe Leu Phe Ser Leu Glu Ser Gln Thr Thr Ile Gly Tyr
    50                  55                  60

Gly Val Arg Ser Ile Thr Glu Glu Cys Pro His Ala Ser Gly Lys Leu
65                  70                  75                  80

Leu Gln Thr His Val Thr Lys Glu Gly Glu Arg Ile Leu Leu Asn Gln
                85                  90                  95

Ala Thr Val Lys Phe His Val Asp Ser Ser Glu Ser Pro Phe Leu
            100                 105                 110

Ile Leu Pro Met Ala Val Cys Gln Ser Arg Thr Ser Tyr Ile Pro Glu
        115                 120                 125

Glu Ile Tyr Trp Gly Phe Glu Phe Val Pro Val Val Ser Leu Ser Lys
            130                 135                 140

Asn Gly Lys Tyr Val Ala Asp Phe Ser Gln Phe Glu
145                 150                 155

<210> SEQ ID NO 46
<211> LENGTH: 154
<212> TYPE: PRT
<213> ORGANISM: Rattus sp.

<400> SEQUENCE: 46

Gly Tyr Pro Pro Glu His Ala Ile Ala Glu Lys Arg Arg Ala Arg Arg
1               5                   10                  15

Arg Leu Leu His Lys Asp Gly Ser Cys Asn Val Tyr Phe Lys His Ile
            20                  25                  30

Phe Gly Glu Trp Gly Ser Tyr Met Val Asp Ile Phe Cys Val Asp Asn
        35                  40                  45

Val His Ser Phe Thr Ala Ala Phe Leu Phe Ser Leu Glu Thr Gln Thr
    50                  55                  60

Thr Ile Gly Tyr Gly Tyr Arg Cys Val Thr Glu Glu Cys Ser Val Ala
65                  70                  75                  80

Arg Ala Gln Leu Leu Arg Tyr Ser Glu Asp Ser Glu Gly Arg Met Thr
                85                  90                  95

Met Ala Phe Lys Asp Leu Lys Leu Val Asn Asp Gln Ile Ile Leu Val
            100                 105                 110

Thr Pro Val Thr Ser His Gln Ser Arg Ser Ser Tyr Val Pro Arg Glu
        115                 120                 125

Ile Leu Trp Gly His Arg Phe His Asp Val Leu Glu Val Lys Arg Lys
    130                 135                 140

Tyr Tyr Lys Val Asn Cys Leu Gln Phe Glu
145                 150

<210> SEQ ID NO 47
<211> LENGTH: 165
<212> TYPE: PRT
<213> ORGANISM: Rattus sp.

<400> SEQUENCE: 47

Glu Asn Leu Arg Lys Pro Arg Ile Arg Asp Arg Leu Pro Lys Ala Arg
1               5                   10                  15

Phe Ile Ala Lys Ser Gly Ala Cys Asn Leu Ala His Lys Asn Ile Arg
            20                  25                  30

Glu Gln Gly Arg Phe Leu Gln Asp Ile Phe Lys Ser Gly Leu Glu Ser
        35                  40                  45

Ala Val Cys Val Thr Asn Val Arg Ser Phe Thr Ser Ala Phe Leu Phe
    50                  55                  60

Ser Ile Glu Val Gln Val Thr Ile Gly Phe Gly Gly Arg Met Met Thr
65                  70                  75                  80

Glu Glu Cys Pro Leu Ala Arg Ile Gln Val Leu Lys Lys Thr Thr Thr
                85                  90                  95

Pro Glu Gly Glu Val Val Pro Ile His Gln Gln Asp Ile Pro Val Asp
            100                 105                 110

Asn Pro Ile Glu Ser Asn Asn Ile Phe Leu Val Ala Pro Leu Ile Thr
        115                 120                 125

```
Thr Gln Ala Arg Thr Ser Tyr Ile Ala Glu Glu Ile Gln Trp Gly His
            130                 135                 140

Arg Phe Val Ser Ile Val Thr Glu Glu Gly Val Tyr Ser Val Asp
145                 150                 155                 160

Tyr Ser Lys Phe Gly
            165

<210> SEQ ID NO 48
<211> LENGTH: 156
<212> TYPE: PRT
<213> ORGANISM: Rattus sp.

<400> SEQUENCE: 48

Asp Pro Thr Glu Pro Arg Tyr Arg Thr Arg Glu Arg Ala Arg Phe
1               5                   10                  15

Val Ser Lys Lys Gly Asn Cys Asn Val Ala His Lys Asn Ile Arg Glu
                20                  25                  30

Gln Gly Arg Phe Leu Gln Asp Val Phe Cys Val Thr Ser Ile His Ser
            35                  40                  45

Phe Ser Ser Ala Phe Leu Phe Ser Ile Glu Val Gln Val Thr Ile Gly
50                  55                  60

Phe Gly Gly Arg Met Val Thr Glu Glu Cys Pro Leu Ala His Met Gln
65                  70                  75                  80

Val Val Arg Lys Thr Thr Ser Pro Glu Gly Glu Val Val Pro Leu His
                85                  90                  95

Gln Val Asp Ile Pro Met Glu Asn Gly Val Gly Gly Asn Ser Ile Phe
            100                 105                 110

Leu Val Ala Pro Leu Ile Thr Thr Gln Ala Arg Thr Ser Tyr Leu Ala
        115                 120                 125

Asp Glu Ile Leu Trp Gly Gln Arg Phe Val Pro Ile Val Ala Glu Glu
130                 135                 140

Asp Gly Arg Tyr Ser Val Asp Tyr Ser Lys Phe Gly
145                 150                 155

<210> SEQ ID NO 49
<211> LENGTH: 150
<212> TYPE: PRT
<213> ORGANISM: Rattus sp.

<400> SEQUENCE: 49

Ala Pro Leu Leu Ser Gln Arg Tyr Arg Arg Met Val Thr Lys Asp Gly
1               5                   10                  15

His Ser Thr Leu Gln Met Asp Gly Ala Gln Arg Gly Leu Val Tyr Leu
                20                  25                  30

Arg Asp Ala Trp Ile Cys Val Lys His Ile Thr Ser Phe Thr Ala Ala
            35                  40                  45

Phe Ser Phe Ser Leu Glu Thr Gln Leu Thr Ile Gly Tyr Gly Thr Met
50                  55                  60

Phe Pro Ser Gly Asp Cys Pro Ser Ala Ser Ala Val Leu Tyr Gln Glu
65                  70                  75                  80

Arg Glu Asn Gly Glu Leu Tyr Gln Thr Ser Val Asp Phe His Leu Asp
                85                  90                  95

Gly Ile Ser Ser Glu Glu Cys Pro Phe Phe Ile Phe Pro Leu Glu Ile
            100                 105                 110

Cys Gln Arg Arg Thr Ser Tyr Leu Pro Ser Glu Ile Met Leu His His
        115                 120                 125
```

```
-continued

Arg Phe Ala Ala Leu Met Thr Arg Gly Ser Lys Gly Glu Tyr Gln Val
    130                 135             140

Lys Met Glu Asn Phe Asp
145                 150
```

KIR CHANNEL MODULATORS

RELATED PATENT APPLICATION

This patent application claims the benefit of U.S. Provisional Patent Application No. 60/945,321, filed on Jun. 20, 2007, entitled KIR CHANNEL MODULATORS, naming Pegan et al. as inventors, and designated by Confirmation No. 8678. The entire content of the foregoing patent application is incorporated herein by reference, including, without limitation, all text, tables and drawings.

STATEMENT OF GOVERNMENT SUPPORT

This invention was made in part with government support under Grant Nos. R01 GM-056653 and R01 NS-37682 awarded by the National Institutes of Health (NIH) and Grant No. 5F31AA017042-02 awarded by the National Institute on Alcohol Abuse and Alcoholism of the NIH. The government has certain rights in this invention.

FIELD OF THE INVENTION

The invention pertains in part to inwardly rectifying potassium (Kir) channels, and modified channels containing an alcohol-binding site. The invention also pertains in part to the identification of agents that modulate channel activity.

BACKGROUND

Biochemical data indicate that eukaryotic Kir channels form hetero- or homo-tetramers [5, 19]. Kir2.1 channels readily form homo-tetramers, as well as hetero-tetramers with other Kir2 family members such as Kir2.2 and Kir2.3 [5, 20]. One of the hallmarks of Kir2 channels is strong inward rectification, in which $K^+$ ions flow preferentially into rather than out of the cell [8]. Inward rectification is produced by cytosolic polyamines and $Mg^{2+}$ occluding the ion conductance pathway as $K^+$ ions are flowing outward. These positively charged particles are then removed from the pore when $K^+$ ions flow into the cell [9]. Rectification is the primary means of gating for Kir2 channels [10-12]. The rate of rectification by these positively charged polyamine and $Mg^{2+}$ block varies between different members of the Kir family depending on the presence of key hydrophilic residues located at two major locations. The strongest binding site of these blockers resides within the trans-membrane site defined by Asp172 in Kir2.1 and weaker, recruiting sites are comprised of several positive and negative charged residues lining the pore in the cytoplasmic domain [9, 13, 14]. The overall effect of rectification allows Kir2.1 to play a key role in eukaryotic cells by driving the resting membrane potential to EK when the cell is at rest [8].

In addition to rectification, Kir channels possess other gating elements. For example, Kir2.1 channels are opened by the binding of the membrane phospholipid PIP2 directly to the channel [15]. Kir channels also can interact with certain alcohols [29, 30, 31]. Using the functional definition of gates as energetic barriers that block the permeation of potassium, it was proposed that a flexible loop, named the G-loop, at the junction between the cytoplasmic and transmembrane domains, can occlude the permeation pathway as an additional gating element [14, 16]. Therefore, at least two energetic barriers, one located inside the pore-lining M2 helix and the other formed by the G-loop, may operate to control the ionic flow. Of the two, the G-loop is unique by being located in the cytoplasmic domains and is too narrow to permit permeation in the absence of PIP2 [14]. Unlike the T1 domain of voltage-gated K channels for which ions flow through side openings created between T1 and transmembrane domains [17], K ions flow through the central pore of Kir2.1 channels beginning at the cytoplasmic domain and continuing to the selectivity filter. How the G-loop and M2 helix regions work together to control ionic flow is unknown. Studies with chimeric KcsA/Kir2.1 channels indicate the cytoplasmic domain is required for Kir2.1 gating [18].

SUMMARY

A structure of a representative inwardly rectifying potassium (Kir) channel protein in combination with an alcohol has been elucidated, and this structure has identified the location of an alcohol-binding site in this class of channels. Alcohols can modulate the activity of channels in this class, and this finding has led to the discovery of agents that modulate Kir channel activity. It has been determined that two sites in Kir channels directly interact with alcohols, and modified Kir channels with modulated alcohol interactions have been generated. Such findings facilitate identifying agents that bind to alcohol interaction sites of Kir channels and modulate the activity of such channels.

Thus, provided herein are methods for identifying an agent that modulates an inwardly rectifying potassium (Kir) channel activity, which comprise: (a) contacting a Kir channel protein or a modified Kir channel protein having an alcohol-binding site with (i) an agent and (ii) an alcohol, and (b) detecting a Kir channel activity, whereby an agent that alters the activity relative to a control activity determined without the agent is identified as an agent that modulates the Kir channel activity.

The invention also in part includes methods for identifying an agent that modulates an inwardly rectifying potassium (Kir) channel activity, which comprise: (a) contacting a modified Kir channel protein having an alcohol-binding site with an agent, and (b) detecting a Kir channel activity, whereby an agent that alters the activity relative to a control activity determined without the agent is identified as an agent that modulates the Kir channel activity. In related embodiments, also provided are methods for identifying an agent that modulates an inwardly rectifying potassium (Kir) channel activity, which comprise: (a) contacting a modified Kir channel protein having an alcohol-binding site with an agent that binds to the alcohol binding site, and (b) detecting a Kir channel activity, whereby an agent that alters the activity relative to a control activity determined without the agent is identified as an agent that modulates the Kir channel activity.

Provided also are methods for modulating an inwardly rectifying potassium (Kir) channel activity, which comprises contacting a Kir channel protein, or a modified Kir channel protein having an alcohol-binding site, with an alcohol under conditions in which the alcohol modulates the Kir channel activity, where the alcohol comprises four or more carbon atoms, and/or the alcohol comprises two or more hydroxyl moieties. Such methods sometimes further comprise contacting the Kir channel protein or the modified Kir channel protein with an agent and determining whether the agent alters the Kir channel activity relative to a control activity determined without the agent, whereby an agent that alters the activity relative to the control activity is identified as an agent that modulates the Kir channel activity.

The invention also in part features methods for identifying a candidate agent that binds to an inwardly rectifying potassium (Kir) channel protein, which comprise: inserting in silico a structure of an agent into a three-dimensional structure of an alcohol-binding site of a Kir channel protein or a modified Kir channel protein; and comparing the fit of the agent in the three-dimensional structure with the fit of an alcohol in the three-dimensional structure; whereby an agent having a fit comparable to the fit of the alcohol is identified as a candidate agent that binds to a Kir channel protein. In certain embodiments, agents identified by methods herein activate or inhibit a Kir channel protein independent of (e.g., in the absence of) a G-protein or G-protein component (e.g., beta-gamma G-protein subunit).

Also provided are compositions of matter comprising an inwardly rectifying potassium (Kir) channel protein, or a modified Kir channel protein having an alcohol-binding site, and an alcohol, wherein: the alcohol comprises four or more carbon atoms, and/or the alcohol comprises two or more hydroxyl moieties. Provided also are compositions of matter comprising a modified inwardly rectifying potassium (Kir) channel protein having an alcohol-binding site and an alcohol. The invention also in part includes compositions of matter comprising a crystal that includes an inwardly rectifying potassium (Kir) channel protein or a modified Kir channel protein having an alcohol-binding site, and an alcohol. Also in part provided are compositions comprising a modified inwardly rectifying potassium (Kir) channel protein having an alcohol-binding site and an alcohol. The invention also in part provides a composition comprising a modified inwardly rectifying potassium (Kir) channel, where: the unmodified counterpart is activated by an alcohol; and the modification decreases sensitivity of the modified channel to activation by the alcohol. In certain embodiments, the modification results in the channel being inhibited by an alcohol, and in some embodiments the alcohol is MPD or 1-propanol. Also, the invention in part provides a composition comprising a modified inwardly rectifying potassium (Kir) channel, where: the unmodified counterpart is inhibited by an alcohol; and the modification decreases sensitivity of the modified channel to inhibition by the alcohol. In certain embodiments, the modification results in the channel being activated by an alcohol, and in some embodiments, the alcohol is 1-butanol. In certain embodiments, the modified channel is a modified Kir3 channel (e.g., Kir 3.2 or Kir 3.4 channel).

In the above-described methods and compositions, the modified Kir channel protein typically includes an alcohol-binding site. In some embodiments the modified Kir channel protein comprises a DE loop and a LM loop, and in certain embodiments the modified Kir channel protein lacks a transmembrane region. The modified Kir channel protein in some embodiments comprises all or a portion of the N-terminal amino acids before the transmembrane region (e.g., a first N-terminal transmembrane region) from a native Kir channel protein sequence.

In some embodiments the Kir channel protein comprises a Kir2 protein amino acid sequence, and sometimes a modified Kir channel protein comprises an amino acid sequence from a Kir2 protein amino acid sequence. A Kir2 protein amino acid sequence sometimes comprises the sequence of SEQ ID NO: 4 or a substantially identical variant thereof. In some embodiments, a Kir channel protein comprises a Kir3 protein amino acid sequence, and sometimes a modified Kir channel protein comprises an amino acid sequence from a Kir3 protein amino acid sequence. A Kir3 protein amino acid sequence comprises the sequence of SEQ ID NO: 8 or SEQ ID NO: 10 or a substantially identical variant thereof.

Any alcohol that binds to a Kir channel protein or modified Kir channel protein, and optionally modulates the activity of the protein, can be utilized in the methods and compositions described herein. In certain embodiments an alcohol comprises two or more hydroxyl moieties, and sometimes an alcohol comprises two hydroxyl moieties. An alcohol may comprise three hydroxyl moieties in some embodiments, and in certain embodiments an alcohol comprises: about four or more carbon atoms, about five or more carbon atoms, about five to about ten carbon atoms, five carbon atoms or six carbon atoms.

In certain embodiments the Kir channel protein or the modified Kir channel protein is in a cell, and in some embodiments the Kir channel protein or the modified Kir channel protein is in a cell-free system. In some embodiments, the alcohol and/or the agent is in association with a solid phase. A Kir channel protein or modified Kir channel protein may comprise a detectable label in some embodiments, and in certain embodiments, an alcohol comprises a detectable label.

Any relevant Kir channel protein activity or modified Kir channel protein activity can be selected and detected by the person of ordinary skill in the art (e.g., detected by methods described herein). In certain embodiments, the activity comprises binding of the Kir channel protein or the modified Kir channel protein to an alcohol. In some embodiments, the Kir channel activity detected comprises membrane conductance, which can include monitoring electric current conducted by a membrane.

In some embodiments, one or more Kir channel amino acids are modified. In certain embodiments, (i) one or more amino acids located in beta strands D and E, and/or intervening sequences, are modified; (ii) one or more amino acids in beta strands L and M, and/or intervening sequences, are modified; (iii) one or more amino acids in beta strands C and D, and/or intervening sequences, are modified; (iv) one or more amino acids between the transmembrane regions are modified (e.g., one or more amino acids between amino acid position 110 and amino acid position 155 are modified); (v) one or more amino acids in the N-terminus of the Kir channel are modified (e.g., between amino acid position 1 to amino acid position 80); (vi) the modified Kir protein is a modified Kir 3.2c protein and the one or more amino acids are selected from the group consisting of Y58, I244, L257, L342, L344 and Y349; (vii) the modified Kir protein is a modified Kir 3.4 protein and the one or more amino acids are selected from the group consisting of S143 and L252.

The invention also in part provides methods for identifying an agent that modulates an inwardly rectifying potassium (Kir) channel activity at a particular site on the Kir channel, which comprise: (a) contacting an unmodified Kir channel protein and at least one modified Kir channel protein with an agent, wherein each modified Kir channel protein binds an alcohol with lower affinity than the unmodified Kir channel protein, and (b) detecting a Kir channel activity of the unmodified Kir channel protein and the modified Kir channel protein, whereby the agent is identified as an agent that modulates the Kir channel activity at a particular site based on a comparison of the activity of the unmodified Kir channel protein relative to activity of the modified Kir channel protein. In certain embodiments, the modified Kir channel includes one or more amino acid modifications at a particular alcohol binding site.

These and other embodiments are described in the following detailed description, claims and drawings.

BRIEF DESCRIPTION OF THE DRAWINGS

The drawings illustrate certain non-limiting embodiments of the invention. Color drawings corresponding to a channel described herein are set forth in Pegan et al., Biochemistry 45: 8599-8606 (2006).

FIG. 1A is a CPK model of surface model of one of four MPD-bound hydrophobic pocket, N-terminus in red, whereas βDβE loop originates from one subunit, βLβM loop originates from second subunit. FIG. 1B, left, is a ribbon and stick view of MPD bound IRK1 hydrophobic pocket. FIG. 1D is a sequence alignment of the three domains between IRK1 and GIRK2 highlighted amino acids interact with MPD. FIG. 1C is a ribbon and stick view of the corresponding hydrophobic pocket in GIRK2 channels. FIG. 1C shows an example of inwardly rectifying current of IRK1 channel recorded from voltage ramps from −100 to +50 mV. One trace is the basal current with 20K external solution (marked "20K"), a second is MPD modulated current (marked "MPD"), and a third is $Ba^{++}$ blocked current (marked "$Ba^{++}$"). FIG. 1F shows an example of inwardly rectifying current of a GIRK2 channel (sequences disclosed as SEQ ID NOS 27-32, respectively, in order of appearance). FIG. 1G shows the average basal current density of IRK1 and GIRK2 (n=5) at −100 mV. FIG. 1H shows an average percent change of basal current for an IRK ("−" designates inhibition), and a GIRK2 channel ("+" designates activation).

FIG. 2A shows an example trace of a dose response recording for MPD dependent activation of GIRK2 channels. Macroscopic currents at −100 were recorded every 2 seconds as increasing concentration was bath applied using a rapid perfusion apparatus. FIG. 2B shows a dose response curve for activation of MPD (n=6, triangle), 1-PrOH (n=6, circle), and EtOH (n=6, square) was plotted as fold change over basal current vs. Log [mM]. FIG. 2C shows an example trace of GIRK channel activation in cells transfected with GIRK2 and M2R; 5 micromolar Carbachol, 100 mM1-PrOH, 100 mM MPD, and 100 mM EtOH mediated activation. FIG. 2D shows an example trace for activation in cells co-transfected with Myr-Phosducin, along with M2R and GIRK2. FIG. 2E shows an induced steady state current density average for cells in FIG. 2C (solid, n=4) and FIG. 2D (hashed, n=7).

FIG. 3 also shows examples of surface staining of mutant HA-tagged GIRK2 channels, where the top right panel shows anti-HA staining of unpermeabilized cells, the top left panel shows anti-GIRK2 staining of same cell after permeablization, and the bottom left panel shows the merged surface and total GIRK2 channel staining.

FIG. 4E, bottom, shows average basal current density of wild type (n=32), Ala (n=9), Asn (n=6), Ile (n=7), Phe (n=7), Tyr (n=9), and Trp (n=9). FIGS. 4A, 4B, 4C and 4D show example traces of modulation of GIRK2 channels by alcohol, Carbachol, and $Ba^{++}$ (left) and averaged data (right). FIG. 4F shows the mean (±SEM) percentage change from Ba++ sensitive basal current.

FIG. 5C shows the dose-response curve for 1-PrOH and MPD. FIG. 5D-G show that a leucine to tryptophan mutation IRK (L245), or GIRK2 PIP (L257) does not alter alcohol mediated inhibition. FIG. 5D, FIG. 5E, FIG. 5F and FIG. 5G show example traces of modulation by the alcohol series for the inwardly rectifying channels (left) and average data for percentage inhibition (FIG. 5H).

FIG. 6A and FIG. 6B show example traces of modulation by the alcohol series by GIRK4 and GIRK4 S143T channels (left) and mean percentage change from basal data (FIG. 6C). FIG. 6D shows an example trace of modulation by the alcohol series of a GIRK2 PIP S148T mutant channel (left) and average percentage inhibition (FIG. 6E). FIG. 6F shows a dose-response curve for inhibition of a GIRK2 PIP channel, GIRK2-PIP-L257W and GIRK2-PIP-S148T.

FIG. 7E, shows an average basal current density of wild type (n=8), Ala (n=8), Tyr (n=8), and Trp (n=8). FIG. 7A, FIG. 7B, FIG. 7C and FIG. 7D show example traces of modulation of GIRK4* channels by alcohol, Carbachol, and $Ba^{++}$ (left) and mean percentage change from basal current (FIG. 7F).

FIGS. 10A and 10B show alignments of amino acid sequences (SEQ ID NOS 36-49, respectively, in order of appearance) in certain regions of particular Kir channels referred to as N-terminal (designed "N1 domain"), DE (designated "βD-βE domain"), LM (designated "βL-βM domain") and pore (designated "Pore Helix") regions. Sequences shown are for rat channels. Given the degree of sequence identity in the regions specified in FIG. 10, the person of ordinary skill in the art can readily determine corresponding amino acid positions to those shown FIG. 10 for channels from other organisms (e.g., human) using sequence alignment methodology known in the art and described herein.

DETAILED DESCRIPTION

Figures 1A, 1B, 1C, 1D:
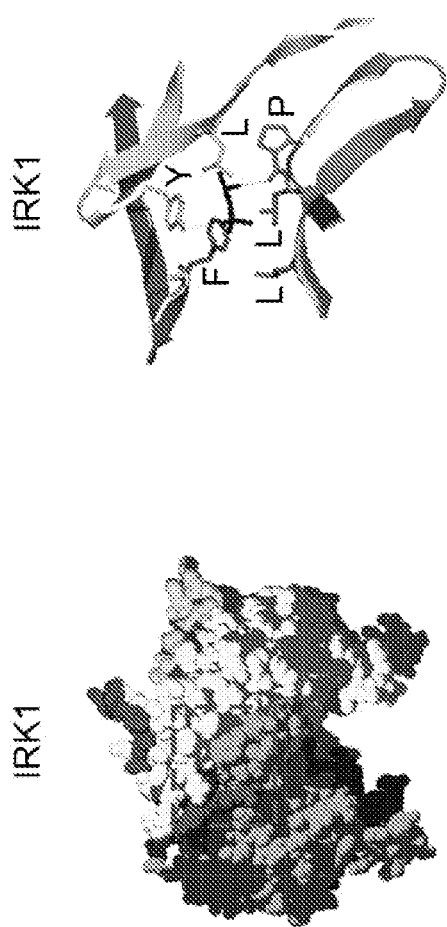
FIGS. 1A-1H show a comparison of MPD-bound IRK1 (also referred to as Kir2.1 or Kir 2) pocket and GIRK2 (also referred to as Kir3.2, Kir3.2c, Kir 3.2) hydrophobic pocket and modulation of IRK1 and GIRK2 by MPD.

Kir channel structures and methods described herein are useful for identifying compounds that modulate Kir channel activities. Kir channel crystals and resulting structures described herein also are useful for identifying structures of novel Kir channel complexes from new crystals.

Kir Channels and Modified Kir Channels

There are about seven Kir channel families currently known, which sometimes are designated as Kir1, Kir2, Kir3, Kir4, Kir5, Kir6 and Kir7 channels. Kir1 members sometimes are referred to as ROMK channels and there are at least two subtypes. Kir2 members sometimes are referred to as IRK channels (e.g., IRK1) and include four subtypes (Kir2.1, Kir2.2, Kir2.3 and Kir 2.4). Kir3 members sometimes are referred to as GIRK channels as they are regulated by G-protein subunits, and there are at least four subtypes (Kir3.1, Kir3.2, Kir3.3 and Kir 3.4, also referred to as GIRK1, GIRK2, GIRK3 and GIRK4). Kir6 members also are referred to as K+ATP channels and there are at least two subtypes (Kir6.1 and Kir6.2).

Certain Kir channels can bind to non-protein ligands, such as an alcohol or phosphatidylinositol bisphosphate (PIP2), and can bind to protein binding partners, such as G-protein subunits. For example, certain Kir3 channels are activated by G-protein beta-gamma subunits and by ethanol, where the G-protein beta-gamma subunit interaction is regulated by PIP2. Certain Kir3 channels also interact with and are inhibited by bupivacaine ($IC_{50}$ of about 20 micromolar). Kir1 and Kir2 channels are insensitive to bupivacaine and they also are G-protein subunit insensitive. Certain Kir2 channels can be inhibited by certain alcohols (e.g., Kir 2.1 channels are inhibited by MPD (described herein) with an IC50 of about 100 mM).

A Kir channel nucleic acid sequence or amino acid sequence may be a prokaryotic or eukaryotic sequence, including, but not limited to, a sequence from an invertebrate, such as a flatworm (e.g., *C. elegans*), or a vertebrate, such as a fish (e.g., *D. rerio*), a rodent (e.g., mouse or rat), an ungulate (e.g., *B. taurus*), a monkey (e.g., *M. mulatta*), an ape (e.g., *P. troglodytes* or *G. beringei*) or human (i.e., *homo sapiens*), for example. The person of ordinary skill in the art can identify nucleic acid and amino acid sequences of various Kir channels by accessing public databases that contain such information (e.g., National Center for Biotechnology Information (NCBI) at the National library of Medicine (NLM), accessible on the World Wide Web (www) at the URL "ncbi.nlm.nih.gov").

For example, a Kir2.1 channel (also sometimes referred to as an IRK1, LQT7, SQT3, HHIRK1 or HHBIRK1 channel) may include a sequence, or may be encoded by a sequence, set forth in the NCBI database, such as a genomic nucleotide sequence (e.g., accession numbers NC_000017.9, NT_010641.15, AC_000060.1 or NW_926918.1), a coding nucleotide sequence (e.g., accession no. NM_000891.2 or NM_008425.3), or an amino acid sequence (e.g., accession no. NP_000882.1). In another example, a Kir3.1 channel (also sometimes referred to as a KGA or a GIRK1 channel) may include a sequence, or may be encoded by a sequence, set forth in the NCBI database, such as a genomic nucleotide sequence (e.g., accession numbers NC_000002.10, NT_005403.16, AC_000045.1 or NW_921585.1), a coding nucleotide sequence (e.g., accession no. NM_002239.2) or an amino acid sequence (e.g., accession no. NP_002230.1). In yet another example, a Kir3.2 channel (also sometimes referred to as a BIR1, GIRK2; KATP2, KCNJ7, hiGIRK2 or MGC126596 channel) may include a sequence, or may be encoded by a sequence, set forth in the NCBI database, such as a genomic nucleotide sequence (e.g., accession numbers NC_000021.7, NT_011512.10, AC_000064.1 or NW_927384.1), a coding nucleotide sequence (e.g., accession no. NM_002240.2) or an amino acid sequence (e.g., accession no. NP_002231.1). In another example, a Kir 3.4 channel (also sometimes referred to as KCNJ5, CIR, KATP1 or GIRK4) may include a sequence, or may be encoded by a sequence, set forth in the NCBI database, such as a genomic nucleotide sequence (e.g., accession numbers NC_000011.8, NT_033899.7, AC_000054.1, NW_925173.1, AC_000143.1, or NW_001838044.1), a coding nucleotide sequence (e.g., accession no. NM_000890.3) or an amino acid sequence (e.g., accession no. NP_000881.3). Nucleic acid and amino acid sequences for other Kir channels can be accessed by the person of ordinary skill in the art in publicly available databases (e.g., World Wide Web URL "ncbi.nlm.nih.gov"), including without limitation, sequences for human Kir2.2 (KCNJ12), Kir2.2 (KCNJ4), Kir3.3 (KCNJ9), Kir4.1 (KCNJ10), Kir4.2 (KCNJ15) and Kir6.2 (KCNJ11) channels and the like.

A modified Kir channel protein or nucleic acid may include one or more amino acid or nucleotide sequence modifications, and contain a substantially identical sequence to a native Kir channel. A modified Kir channel protein may exhibit one or more functions of a corresponding native Kir channel, including, but not limited to, membrane association, ion (e.g., potassium) transport, interaction with a non-protein ligand (e.g., alcohol or PIP2) and interaction with a protein binding partner. A particular function of a modified Kir channel may be modulated with respect to the corresponding native Kir channel function (e.g., the modulated Kir channel may associate with lower affinity to a membrane, or may not measurably associate with a membrane, as compared to the membrane association function of a corresponding native Kir channel).

The term "substantially identical" as used herein with respect to sequences refers to a nucleotide or amino acid sequence sharing a certain amount of sequence identity to a nucleotide sequence or amino acid sequence of a Kir channel or portion thereof. Included are nucleotide sequences or amino acid sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to a native nucleotide sequence or amino acid sequence of a Kir channel (e.g., a sequence disclosed in the NCBI database). A substantially identical sequence also may have one to ten nucleotide or amino acid substitutions as compared to a native Kir channel sequence. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences. Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the World Wide Web (www) URL address "gcg.com"), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at the World Wide Web URL gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Another manner for determining whether two nucleic acids are substantially identical is to assess whether a polynucleotide homologous to one nucleic acid will hybridize to the other nucleic acid under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

An example of a substantially identical Kir channel nucleotide sequence is one that has a different nucleotide sequence than a native Kir channel nucleotide sequence but still encodes the same amino acid sequence encoded by the native Kir channel nucleotide sequence. Another example is a nucleotide sequence that encodes a protein having an amino acid sequence 90% or more, 91% or more, 92% or more, 93% or more, 94% or more, 95% or more, 96% or more, 97% or more, 98% or more or 99% or more identical to an amino acid sequence encoded by a native Kir channel nucleotide sequence.

Kir channel nucleotide sequences and encoded amino acid sequences can be used as "query sequences" to perform a search against public databases to identify other family members or related sequences, for example. Such searches can be performed using the NBLAST and XBLAST programs (version 2.0) of Altschul et al., J. Mol. Biol. 215: 403-10 (1990). BLAST nucleotide searches can be performed with the NBLAST program, score=100, wordlength=12 to obtain homologous nucleotide sequences. BLAST polypeptide searches can be performed with the XBLAST program, score=50, wordlength=3 to obtain amino acid homologous. To obtain gapped alignments for comparison purposes, Gapped BLAST can be utilized as described in Altschul et al., Nucleic Acids Res. 25(17): 3389-3402 (1997). When utilizing BLAST and Gapped BLAST programs, default parameters of the respective programs (e.g., XBLAST and NBLAST) can be used (see the World Wide Web (www) URL address "ncbi.nlm.nih.gov").

Substantially identical nucleotide sequences may include altered codons for enhancing expression of an amino acid sequence in a particular expression system. One or more codons may be altered, and sometimes about 5% or more, about 10% or more or about 20% or more of the codons are altered for optimized expression in an expression system that may include bacteria (e.g., E. coli), yeast (e.g., S. cervesiae), human (e.g., 293 cells), insect, or rodent (e.g., hamster) cells.

Examples of modified Kir channels include those that encode or have one or more amino acid modifications in one or more particular regions of a Kir channel that interact with an alcohol. In some embodiments one or more amino acids located in beta strands D and E, and intervening sequences, are modified. This region is referred to herein as a "DE region," "βD-βE domain" and "βDβE region." This region can be between about amino acid 195 and about amino acid 285 of a Kir channel, for example, and non-limiting examples of amino acid sequences of the region are shown in FIG. 10B.

In certain embodiments, one or more amino acids in beta strands L and M, and intervening sequences, are modified. This region is referred to herein as a "LM region," "βL-βM domain" and "βLβM region." This region can be between about amino acid 275 and about amino acid 350 of a Kir channel, for example, and non-limiting examples of amino acid sequences of the region are shown in FIG. 10B.

In certain embodiments, one or more amino acids in the N-terminal region of the channel, before the first transmembrane region, are modified. This region is referred to herein as a "N-terminal region" and "N1 domain." This region can be between amino acid position 1 and amino acid position 80 in a Kir channel, between amino acid position 1 and amino acid position 70 in a Kir channel, between amino acid position 1 and amino acid position 60 in a Kir channel, or between amino acid position 1 and amino acid position 50 in a Kir channel, for example, and several non-limiting examples of this region are shown in FIG. 10A.

The term "alcohol binding pocket" as used herein refers to a region in a Kir channel protein that includes N1, βD-βE, βL-βM domains.

In certain embodiments, one or more amino acids in beta strands C and D, and intervening sequences, are modified. This region is referred to herein as a "CD region," "βC-βD domain" and "βCβD region."

Figure 9:
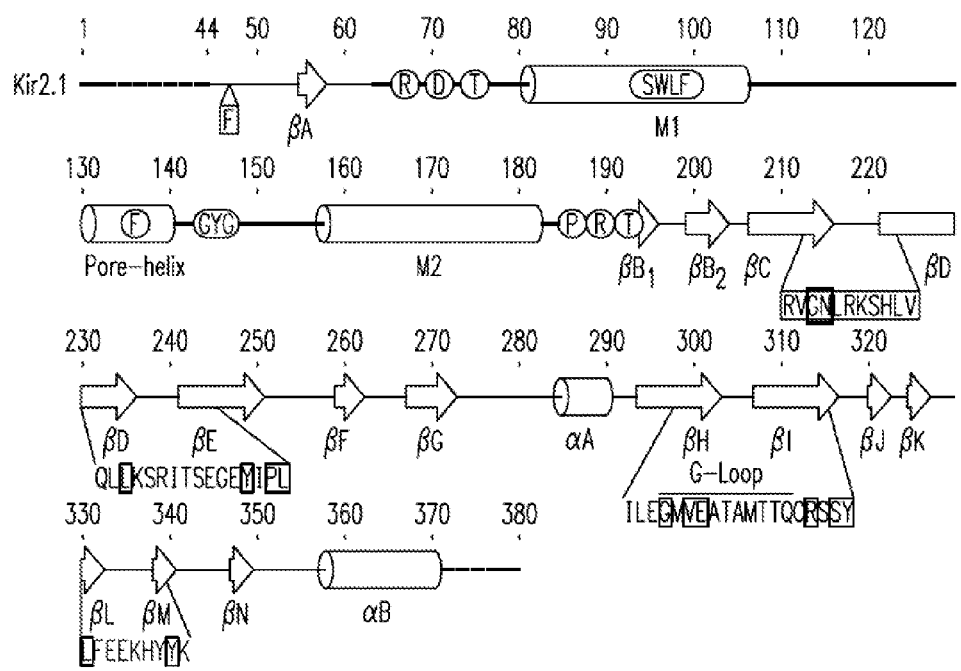
FIG. 9 shows secondary structure elements of Kir2.1 with MPD binding site locations (beta sheets in arrows and alpha helices in cylinders). Figure discloses SEQ ID NOS 33, 28 and 34-35, respectively, in order of appearance.

In some embodiments, one or more amino acids between the transmembrane regions (e.g., designated by "M1" and "M2" in FIG. 9 for a Kir2.1 channel) are modified. This region is referred to herein as a "pore region" and "pore helix." A pore region or pore helix can be, for example, between amino acid position 110 and amino acid position 165, between amino acid position 115 and amino acid position 155, between amino acid position 125 and amino acid position 145, between amino acid position 130 to amino acid position 140, in a region spanning the "pore helix" and the GYG sequence shown in FIG. 9, or within the "pore helix" illustrated in FIG. 9, for example, and several non-limiting examples of this region are shown in FIG. 10A.

In certain embodiments, one or more of the following positions in a Kir protein or modified Kir protein are modified: (i) in Kir2.1, F47, L232, L245, L339, E332 and Y227; (ii) in Kir3.2, Y58, S148, I244, L257, L342, L344 and Y349; (iii) in Kir3.4, S143, L252 and any amino acids corresponding to those listed for Kir2.1 and Kir3.2; and (iv) amino acids in any other Kir protein or modified Kir protein corresponding to one or more positions in N1, βD-βE, or βL-βM domains or pore region as determined by a sequence alignment with a Kir2.1, Kir 3.2, or Kir 3.4 sequence, respectively. In some embodiments, such as those related to embodiments in the preceding paragraph for example, a Kir channel protein may include all, none or some (e.g., include 1, 2, 3, 4, 5, 6, 7, 8, 9, 10, 11, 12, 13, 14, 15, 16, 17, 18, 19 or 20 amino acids from a particular region) of the amino acids in each of the regions specified, independently determined for each region. In certain embodiments, a modified Kir channel comprises no modifications, or one or more modifications, in the pore region and/or the alcohol binding pocket.

The term "amino acid modification" as used herein can be a deletion, addition or substitution. In the case of a substitution, the modification may be conservative or non-conservative, the selection of which is known to a person of ordinary skill in the art. Examples of conservative amino acid modifications include, but are not limited to, basic to basic side chain amino acid substitution (e.g., Lys, Arg), acidic to acidic side chain amino acid substitution (e.g., Glu, Asp), hydrophobic to hydrophobic side chain amino acid substitution (e.g., Ala, Val, Leu, Ile; Trp, Phe, Tyr), polar to polar side chain amino acid (e.g., Ser, Thr) and substitution with an amino acid having a side chain of like size (e.g., Glu, Gln; Asp, Asn; Ser, Cys; Trp, Phe). Non-conservative amino acid substitutions sometimes include substituting a basic or acidic side chain amino acid with a non-basic or non-acidic side chain amino acid (e.g., Lys to Asp) or substituting an amino acid with another having a relatively different size (e.g., Arg to Gly), for example.

In certain embodiments, one or more amino acids that can accept a post translation modification are substituted with an amino acid not capable of bearing the post-translational modification (e.g., phosphoryl, acyl, saccharide, ubiquitin and the like). Certain examples of modified Kir channel proteins are those that include one or more unnatural amino acids. Unnatural amino acids include, but are not limited to, D-isomer amino acids, ornithine, diaminobutyric acid, norleucine, pyrylalanine, thienylalanine, naphthylalanine and phenylglycine, alpha and alpha-disubstituted amino acids, N-alkyl amino acids, lactic acid, halide derivatives of natural amino acids such as trifluorotyrosine, p-Cl-phenylalanine, p-Br-phenylalanine, p-I-phenylalanine, L-allyl-glycine, beta-alanine, L-alpha-amino butyric acid, L-gamma-amino butyric acid, L-alpha-amino isobutyric acid, L-epsilon-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), 2,4-diaminobutyric acid, 4-aminobutyric acid (gamma-Abu), 2-amino butyric acid (alpha-Abu), 6-amino hexanoic acid (epsilon-Ahx), 2-amino isobutyric acid (Aib), 3-amino propionic acid, ornithine, norleucine, norvaline, hydroxyproline, sarcosine, citrulline, homocitrulline, cysteic acid, t-butylglycine, t-butylalanine, an amino acid derivatized with a heavy atom or heavy isotope (e.g., gold isotope, selenium isotope, deuterium, nitrogen isotope; useful for synthesizing protein applicable to X-ray crystallographic structural analysis or nuclear magnetic resonance analysis), phenylglycine, cyclohexylalanine, fluoroamino acids, designer amino acids such as beta-methyl amino acids, Ca-methyl amino acids, Na-methyl amino acids, naphthyl alanine, and the like.

In certain embodiments, modified Kir channel sequences may lack one or more amino acids, or may lack nucleotides that encode such missing amino acids. Such modified sequences may be missing one to ten amino acids (or the codons encoding them in the corresponding nucleotide sequence), or longer stretches of consecutive amino acids may be removed. Consecutive amino acids from one or both ends of a Kir channel may be removed, and consecutive amino acids in one or more interior regions of a Kir channel may be removed. In certain embodiments, one or more amino acids capable of bearing a post-translational modification (e.g., phosphoryl, acyl, saccharide, ubiquitin) may be removed. One or more amino acids may be removed from a functional region of a native Kir channel, and in some embodiments, the once functional region may no longer retain the same function (e.g., the modification may result in the region becoming semi-functional or non-functional). For example, one or more amino acids may be removed from a transmembrane region of a Kir channel, and the modification may result in the modified protein not associating measurably with a membrane. In certain embodiments, such as those involving Kir2 and Kir3 channels, two or more consecutive amino acids may be removed from a region spanning about amino acid 60 to about amino acid 195, which corresponds to a transmembrane region (e.g., amino acids from a region spanning about amino acid 65 to about amino acid 188 in a Kir 2.1 channel, or a region spanning about amino acid 64 to about amino acid 189 in a Kir3.1 channel). In some embodiments, two or more consecutive amino acids may be removed from an N-terminal region of a Kir channel outside of the channel domain, for example, in a region spanning about amino acid 1 to about amino acid 45. In certain embodiments, consecutive amino acids from a region spanning about amino acid 1 to about amino acid 43 are removed in a Kir2.1 channel, or consecutive amino acids in a region spanning about amino acid 1 to about amino acid 40 are removed in a Kir3.1 channel. In certain embodiments, two or more amino acids may be removed from a C-terminal region of a Kir channel outside of the channel domain, for example, amino acids after about amino acid 365. In some embodiments, a Kir2.1 channel or a Kir3.1 channel may terminate at about amino acid 371.

A modified Kir channel or modified Kir channel generally includes an alcohol-binding site, and often includes a DE loop region and a LM loop region. In some embodiments, a modified Kir channel includes a N-terminal region, a DE loop region and a LM loop region. In certain embodiments, a N-terminal region spans from about amino acid position 1 to about position 45, and can span from (i) about amino acid position 1 to about position 43 in a Kir2.1 channel, or (ii) about amino acid 1 to about amino acid 40 in a Kir3.1 channel, for example. In some embodiments, a DE loop region, which also can be referred to as a "BD loop" region, can span (i) about amino acid position 230 (e.g., Q230) to about position 245 (e.g., L245) for Kir2.1; (ii) about amino acid position 231 (e.g., K231) to about position 246 (e.g., L246) for Kir3.1; or (iii) about amino acid position 242 (e.g., K242) to about position 257 (e.g., L257) for Kir3.2. In some embodiments, a LM loop region can span (i) about amino acid position 330 (e.g., L330) to about position 338 (e.g., K338) for Kir2.1; (ii) about amino acid position 331 (e.g., I331) to about position 339 (e.g., K339) for Kir3.1; or (iii) about amino acid position 342 (e.g., L342) to about position 350 (e.g., E350) for Kir3.2. In some embodiments, certain amino acids in a Kir protein, such as one or more amino acids in a N-terminal region, a DE loop region and/or a LM loop region are modified. In certain embodiments, a modified Kir channel protein includes about 400 or fewer, about 350 or fewer, about 300 or fewer, about 250 or fewer, about 200 or fewer, about 150 or fewer or about 100 or fewer amino acids.

A particular Kir channel protein or modified variant may be present in a composition as a monomer or in combination with one or more other proteins. A Kir channel may be in association with a protein binding partner, such as one or more partners described hereafter. In certain embodiments, a Kir channel is a multimer of one or more other like Kir channel units (homomultimer) or one or more different Kir channel units (heteromultimer). Heteromultimers may include two or more like Kir channel units and one or more different Kir channel units. Multimers can include any number of Kir channel units, such as dimers, trimers, tetramers, hexamers or octamers, for example. Kir channels sometimes are tetramers, such as homotetramers (e.g., four Kir3.1 units or four Kir3.2 units) or heterotetramers (e.g., two Kir3.1 units and two Kir3.2 units). Multimeric Kir channels may include one or more modified Kir channel units (e.g., all Kir channels may be modified Kir channels in each multimer). A Kir channel multimer may be in combination with another non-Kir channel binding partner in certain embodiments. Thus, the term "Kir channel protein" as used herein refers to a Kir channel monomer, homomultimer or heteromultimer, which may be in association with one or more other proteins, molecules or agents. Further, a Kir channel protein can be referenced as containing a certain Kir subunit. For example, a Kir channel protein homomultimer or heteromultimer containing one or more Kir3.2 subunits or Kir3.4 subunits can be referred to as a "Kir3.2-containing" channel protein or "Kir3.4-containing" channel protein, respectively.

In some embodiments, a Kir channel or modified Kir channel protein, or a nucleic acid that encodes such a protein, is isolated or purified. The term "isolated" as used herein refers to material removed from its original environment (e.g., the natural environment if it is naturally occurring, or a host cell if expressed exogenously), and thus is altered "by the hand of man" from its original environment. The terms "isolated" and "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Alcohols

A suitable alcohol that interacts with (e.g., binds to) a Kir channel or modified Kir channel may be utilized and selected by the person of ordinary skill in the art in methods and compositions described herein. An alcohol that specifically binds to a Kir channel or modified Kir channel sometimes is selected. An alcohol may modulate an activity of a Kir channel or modified Kir channel. For example, an alcohol can activate a Kir3 channel and can inhibit a Kir2 channel.

A Kir channel or modified Kir channel may be contacted with an alcohol in any convenient manner. An alcohol may be added to a system at the same time a Kir channel or modified Kir channel is added, or before or after the channel is added to the system. For example, an alcohol may be added to one or more wells of a microwell plate before or after a Kir channel or modified Kir channel is added to wells in a screening assay embodiment. In another example, a crystalline form of a Kir channel may be prepared under conditions in which an alcohol is added to crystallization conditions at the same time the channel is added or is added before or after the channel is added.

Alcohols include those that comprise a straight chain or branched C1-C20 alkyl or C1-C20 alkenyl linked to one or more hydroxyl moieties (e.g., one, two, three or four hydroxyl moieties). Monohydroxy alcohols include, but are not limited to, methanol, ethanol, propanol, butanol, pentanol, hexanol, heptanol, octanol, nonanol, decanol and dodecanol, and included herein are multi-hydroxy versions of such alcohols (e.g., containing two or three hydroxyl moieties). In certain embodiments the alcohol comprises two or more hydroxyl moieties, and sometimes the alcohol comprises two hydroxyl moieties. An alcohol may comprise three hydroxyl moieties in some embodiments, and in certain embodiments an alcohol comprises: about four or more carbon atoms, about five or more carbon atoms, about five to about ten carbon atoms, five carbon atoms or six carbon atoms.

Alcohols that can be utilized include, but are not limited to, 2-methyl-2,4-pentanediol (MPD); 3-methyl-1,3,5-pentanetriol; 2,5-dimethyl-1,2,6-hexanetriol and 2,4-pentanediol. Alcohols can contain one or more chiral centers. A mixture of isomers may be provided (a racemate), or a particular isomer in substantially pure form may be provided (e.g., (S)-(+)-2-methylpentane-2,4-diol). For alcohols having two or more chiral centers, a group of isomers, in which one or more or all chiral centers are resolved, may be provided. Other alcohols that can be utilized include, without limitation, methanol, ethanol, propanol (e.g., 1-propanol), butanol (e.g., 1-butanol) and the like.

An alcohol may include a detectable label (e.g., a radioisotope incorporated in the alcohol (e.g., $^{14}C$, $^{3}H$)). The amount of alcohol utilized can be determined by the person of ordinary skill in the art from known information, information provided herein and information accessed by routine determinations of the effect of an alcohol on channel activity.

Agents

Agents utilized in the methods and compositions described herein can be any molecule that interacts with (e.g., binds to), or potentially interacts with, a Kir channel or modified Kir channel, and suitable agents can be selected by the person of ordinary skill in the art. An agent, in certain embodiments, specifically binds to a Kir channel or modified Kir channel. An agent may be provided in any convenient form, such as in substantially pure form (e.g., isolated form), for example. Agents may be screened according to a particular activity or function of a Kir channel as described herein. An agent may directly compete with, or may indirectly affect (e.g., allosterically influence), the binding of a Kir channel ligand or binding partner to a Kir channel or modified Kir channel. An agent may, for example, directly compete with an alcohol for an alcohol-binding site of a Kir channel or modified Kir channel, and an agent may be selected that has one or more chemical or structural attributes in common with an alcohol for such applications.

A person of ordinary skill in the art may select an agent from a variety of different molecules, including, but not limited to, organic compound agents, inorganic compound agents, peptide and protein agents (e.g., peptide, peptioid, antibody and binding partner agents) and nucleic acid agents (e.g., ribozyme, antisense, interfering RNA (RNAi) and short heteronuclear RNA (siRNA) agents). Organic and inorganic compounds can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive (see, e.g., Zuckermann et al., J. Med. Chem. 37: 2678-85 (1994)); spatially addressable parallel solid phase or solution phase libraries; synthetic library methods requiring deconvolution; "one-bead one-compound" library methods; and synthetic library methods using affinity chromatography selection. Biological library and peptoid library approaches are typically limited to peptide libraries, while the other approaches are applicable to peptide, non-peptide oligomer or small molecule libraries of compounds (Lam, Anticancer Drug Des. 12: 145, (1997)). Examples of methods for synthesizing molecular libraries are described, for example, in DeWitt et al., Proc. Natl. Acad. Sci. U.S.A. 90: 6909 (1993); Erb et al., Proc. Natl. Acad. Sci. USA 91: 11422 (1994); Zuckermann et al., J. Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994). Libraries of compounds may be presented in solution (e.g., Houghten, Biotechniques 13: 412-421 (1992)), oron beads (Lam, Nature 354: 82-84 (1991)), chips (Fodor, Nature 364: 555-556 (1993)), bacteria or spores (Ladner, U.S. Pat. No. 5,223,409), plasmids (Cull et al., Proc. Natl. Acad. Sci. USA 89: 1865-1869 (1992)) or on phage (Scott and Smith, Science 249: 386-390 (1990); Devlin, Science 249: 404-406 (1990); Cwirla et al., Proc. Natl. Acad. Sci. 87: 6378-6382 (1990); Felici, J. Mol. Biol. 222: 301-310 (1991); Ladner supra.). Organic and inorganic compounds may have one or more chiral centers, and mixtures of isomers (racemates) or substantially isolated isomers may be provided.

An organic or inorganic compound sometimes is a small molecule. Small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A variety of antibodies and antibody fragments are available to and can be generated by the person of ordinary skill in the art. An antibody or antibody fragment selected by the artisan sometimes binds to a Kir channel or modified Kir channel unit or a complex with a Kir channel ligand or binding partner. An antibody or antibody fragment may bind to a Kir channel complex without significantly disrupting binding between the channel and its ligand or binding partner, or alternatively the antibody may bind and disrupt interactions between the channel and its ligand or binding partner.

Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. Polyclonal and monoclonal antibodies that bind specific antigens are commercially available, and methods for generating such antibodies are known. In general, polyclonal antibodies are produced by injecting an isolated antigen (e.g., Kir channel or fragment thereof) into a suitable animal (e.g., a goat or rabbit); collecting blood and/or other tissues from the animal containing antibodies specific for the antigen and purifying the antibody. Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen (e.g., Kohler & Milstein, Nature 256:495 497 (1975) and StGroth & Scheidegger, J Immunol Methods 5:1 21 (1980)).

Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain. Given that the variable region of an antibody is formed from six complementarity-determining regions (CDRs) in the heavy and light chain variable regions, one or more CDRs from one antibody can be substituted (i.e., grafted) with a CDR of another antibody to generate chimeric antibodies. Also, humanized antibodies are generated by introducing amino acid substitutions that render the resulting antibody less immunogenic when administered to humans.

An agent sometimes is an antibody fragment, such as a Fab, Fab', F(ab)'2, Dab, Fv or single-chain Fv (ScFv) fragment, and methods for generating antibody fragments are known (see, e.g., U.S. Pat. Nos. 6,099,842 and 5,990,296 and PCT/GB00/04317). In some embodiments, the fragment is a single-chain antibody fragment, which sometimes is constructed by joining a heavy chain variable region with a light chain variable region by a polypeptide linker (e.g., the linker is attached at the C-terminus or N-terminus of each chain) by recombinant molecular biology processes. Such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342,221). Antibody fragments often comprise engineered regions such as CDR-grafted or humanized fragments. In certain embodiments the binding partner is an intact immunoglobulin, and in other embodiments the binding partner is a Fab monomer or a Fab dimer.

Nucleic acid agents can be utilized. Methods for designing and utilizing RNAi and siRNA are known, e.g., Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Antisense nucleic acid agents also may be utilized, and may contain DNA or RNA structures or synthetic nucleic acid structures known to the person of ordinary skill in the art.

Synthetic structures include, but are not limited to, peptide nucleic acid (PNA), alpha anomeric, phosphorothioate derivatives, acridine-substituted, 2'-o-methylribonucleotide-containing and chimeric RNA/DNA alternative structures (e.g., Inoue et al., FEBS Lett. 215: 327-330 (1987); Gaultier et al., Nucleic Acids. Res. 15: 6625-6641 (1987); U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; 5,614,622; 5,739,314; 5,955,599; 5,962,674; 6,117,992; WIPO publications WO 00/56746, WO 00/75372 and WO 01/14398). Use of ribozyme nucleic acids also is known to the person of ordinary skill in the art (e.g., U.S. Pat. No. 5,093,246 or Haselhoff and Gerlach, Nature 334: 585-591 (1988); Cech et al. U.S. Pat. No. 4,987,071; Cech et al. U.S. Pat. No. 5,116,742 and Bartel & Szostak, Science 261: 1411-1418 (1993)).

Kir Channel Activities

Certain methods described herein involve the detection of a Kir channel activity. One or more activities can be detected at a particular time or in a particular assay, and a person of ordinary skill in the art can select one or more activities for detection. Examples of Kir channel activities include, but are not limited to, interaction of a channel with a non-protein ligand; interaction of a channel with a protein binding partner; interaction of a channel with a membrane; localization of a Kir channel or modified Kir channel in a cell; post-translational modification state of a Kir channel or modified Kir channel; expression level of a Kir channel or modified Kir channel; interaction of a Kir channel or modified Kir channel with an ion (e.g., potassium ion); interaction of a Kir channel or modified Kir channel with an agent (e.g., specific binding of an agent to a Kir channel or modified channel; measurement of binding affinity), and transport of an ion (e.g., potassium) by a channel.

Examples of non-protein ligands include, but are not limited to, an alcohol (e.g., described above), PIP2 or a structural variant thereof and an anesthetic (e.g., bupivacaine). Examples of protein binding partners include, but are not limited to, the same or different Kir channel or modified Kir channel units (e.g., channel homomultimers or heteromultimers), AKAP5, DLG1, SLG4, IL16 and G-protein beta-gamma subunits. For example, Kir2.1 channel protein binding partners include, but are not limited to, A kinase anchor protein 5 (AKAP5); Synapse associated protein 97 (DLG1); Synapse associated protein 90 (DLG4); Interleukin 16 (IL16); NP_004973.1 (KCNJ8); Kir2.3; Kir5.1; Kir6.2 and another Kir2.1 channel. Kir3.1 channel protein binding partners include, but are not limited to, potassium inwardly rectifying channel subfamily J member 5 (KCNJ5; also known as CIR, GIRK4, KATP1 and KIR3.4); potassium channel inwardly rectifying subfamily J. member 9 (KCNJ9; NP_004974.2; also known as RP11-536C5.1, GIRK3 and KIR3.3); G-protein beta and another Kir3.1 or Kir3.2 channel protein, for example. Kir3.2 channel protein binding partners include, but are not limited to, beta-2-adrenergic receptor (ADRB2); dopamine receptor D2 (DRD2); potassium channel inwardly rectifying subfamily J. member 9 (KCNJ9; NP_004974.2); G-protein beta-gamma; Galphai/o and Galphaq G proteins; and another Kir3.1 or Kir3.2 channel protein, for example. Kir3.3 and Kir3.2c channels also can bind to sorting nexin 27, for example. Binding partner sequences can be identified by the person of ordinary skill in the art by accessing public databases (e.g., NCBI), the nucleotide sequences may be isolated based on such information, and binding partner proteins may be expressed therefrom.

Methods for identifying an interaction between a membrane and a Kir channel or modified Kir channel, or the cell localization of such channels, are known in the art. Such methods include cell-free and cellular assays, and optionally involve the use of microscopy to identify the location of the Kir channel or modified Kir channel (e.g., the channel sometimes is labeled with a microscopy-detectable molecule). Methods sometimes include cross-linking a Kir channel or modified Kir channel to a membrane or cell component before imaging the location of the channel. Localization methods also sometimes include fractionating and detecting the presence or absence of a channel in different portions of a cell or membrane preparation (e.g., sedimentation).

Ion binding and ion transport by a Kir channel or modified Kir channel can be measured and quantified in a number of approaches known to the person of ordinary skill in the art. For example, ion transport can be detected by electrophysiological alterations in cells or vesicles containing a Kir channel or modified Kir channel. Different electrical parameters can be monitored in cells or vesicles containing a Kir channel to determine ion transport, such as voltage, electric current and resistance. Patch clamp methods are known (e.g., described hereafter) and automated electrophysiological detectors of ion transport are available (e.g., Patchliner©, Nanion Technologies; Munchen, Germany).

The presence or absence of a Kir channel post-translational modification can be detected by any method known to a person of ordinary skill in the art. Any modification can be monitored, such as addition or removal of a phosphoryl, alkyl (e.g., methyl), fatty acid (e.g., myristoyl or palmitoyl), isoprenyl, glycosyl (e.g., polysaccharide), acetyl or peptidyl (e.g., ubiquitin). Modifications sometimes are detected by reacting a Kir channel with an antibody that specifically binds to the post-translationally added moiety (e.g., anti-phosphotyrosine or anti-phosphoserine antibodies). Multiple glycosidic linkages are known to the artisan, including, but not limited to N-glycosidic linkages (e.g., GlcNAc-β-Asn, Glc-β-Asn, Rha-Asn and Glc-β-Arg linkages); β-glycosidic linkages (e.g., linkages to Ser. Thr, Tyr, Hyp (hydroxyproline), and Hyl (hydroxylysine); GalNAc-Ser/Thr, GalNAc-β-Ser/Thr, Gal-Ser/Thr, Man-Ser/Thr, Fuc-Ser/Thr, Glc-β-Ser, Pse-Ser/Thr, DiActrideoxyhexose-Ser/Thr, FucNAc-β-Ser/Thr, Xyl-β-Ser, Glc-Thr, GlcNAc-Thr, Gal-β-Hyl, Gal-Hyp, Gal-β-Hyp, Ara-Hyp Ara-β-Hyp, GlcNAc-Hyp, Glc-Tyr and Glc-β-Tyr linkages); C-mannosyl linkages (e.g., mannosyl linkage to C-2 of the Trp through a C—C bond); phosphoglycosyl linkages (e.g., attachment of sugar (e.g., GlcNAc, Man, Xyl, and Fuc) to protein via a phosphodiester bond; GlcNAc-1-P-Ser, Man-1-P-Ser, Xyl-1-P-Ser, Fuc-β-1-P-Ser linkages); and glypiated linkages (e.g., Man is linked to phosphoethanolamine, which in turn is attached to the terminal carboxyl group of a protein). Extent of glycosylation can be assessed by the artisan using known methods (e.g., Spiro, Glycobiology 12: 43R-56R (2002)).

A control activity sometimes is measured to determine the presence or absence of an effect of an agent on a particular biological activity, and to quantify an effect identified. A control activity in some embodiments is a Kir channel activity detected when no agent is present in the system. Control activities also may be determined when a known activator or known inhibitor of a Kir channel activity is present in the system. Measurements of a Kir channel activity in the presence of an agent can be compared to control measurements and the effects of such agents on channel activity can be determined.

Detection of Kir Channel Activities

Components may be contacted in any convenient and suitable format or system by the person of ordinary skill in the art to detect a Kir channel activity. As used herein, the term "system" refers to an environment that receives assay components (e.g., Kir channel, modified Kir channel, alcohol, binding partner and/or agent components), including, but not limited to microtiter plates (e.g., 96-well or 384-well plates), silicon chips having molecules immobilized thereon and optionally oriented in an array (see, e.g., U.S. Pat. No. 6,261, 776 and Fodor, Nature 364: 555-556 (1993)), microfluidic devices (see, e.g., U.S. Pat. Nos. 6,440,722; 6,429,025; 6,379, 974; and 6,316,781) and cell culture vessels. The system can include attendant equipment, such as signal detectors, robotic platforms, pipette dispensers and microscopes. A system sometimes is an in vitro system, sometimes is an in vivo system, sometimes is cell-free, sometimes includes one or more cells, sometimes includes or is a cell sample from an animal (e.g., a biopsy, organ, appendage), and sometimes is a non-human animal in certain embodiments. Cells may be extracted from any appropriate subject, such as a mouse, rat, hamster, rabbit, guinea pig, ungulate (e.g., equine, bovine, porcine), monkey, ape or human subject, for example. Components can be added to the system in any order that allows detection of the desired channel activity.

Assay systems sometimes are heterogeneous or homogeneous. In heterogeneous assays, one or more reagents and/or assay components are immobilized on a solid phase, and complexes can be detected on the solid phase at the end of the reaction (e.g., channel-alcohol complexes). In homogeneous assays, the entire reaction is carried out in a liquid phase. In either approach, the order of addition of reactants can be varied to obtain different information about the molecules being tested. For example, agents that agonize channel/binding partner interactions can be identified by conducting the reaction in the presence of the agents in a competition format. Alternatively, test molecules that agonize preformed complexes, e.g., agents with higher binding constants that displace one of the components from the complex, can be tested by adding an agent to the reaction mixture after complexes have been formed. A complex may comprise a channel and a non-protein ligand (e.g., alcohol, PIP2, anesthetic) or a channel and a protein binding partner, for example.

In some embodiments, the reaction can be conducted in a liquid phase in the presence or absence of an agent, where the reaction products are separated from unreacted components, and the complexes are detected (e.g., using an immobilized antibody specific for one of the binding components to anchor any complexes formed in solution, and a labeled antibody specific for the other partner to detect anchored complexes). Depending upon the order of addition of reactants to the liquid phase, agents that inhibit complex or that disrupt preformed complexes can be identified, for example.

In a heterogeneous assay embodiment, one or more assay components are anchored to a solid surface and a non-anchored component or reagent often is labeled, either directly or indirectly. The anchored molecule can be immobilized by non-covalent or covalent attachments. Alternatively, an immobilized antibody specific for the molecule to be anchored can be used to anchor the molecule to the solid surface. A partner of the immobilized species may be exposed to the coated surface with or without an agent. After the reaction is complete, unreacted components can be removed (e.g., by washing) such that a significant portion of any complexes formed remain immobilized on the solid surface. Where the non-immobilized species is pre-labeled, detection of label immobilized on the surface is indicative of complex formation. Where the non-immobilized species is not pre-labeled, an indirect label can be used to detect complexes anchored to the surface (e.g., by using a labeled antibody specific for the initially non-immobilized species). Depending upon the order of addition of reaction components, test compounds that inhibit complex formation or disrupt preformed complexes can be detected.

The term "solid support" or "solid phase" as used herein refers to a wide variety of materials including solids, semi-solids, gels, films, membranes, meshes, felts, composites, particles, and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Diamandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997 (1998); Kessler et al., Agnew. Chem. Int. Ed. 40: 165 (2001); Smith et al., J. Comb. Med. 1: 326 (1999); Orain et al., Tetrahedron Lett. 42: 515 (2001); Papanikos et al., J. Am. Chem. Soc. 123: 2176 (2001); Gottschling et al., Bioorg. And Medicinal Chem. Lett. 11: 2997 (2001). For example, Kir channels or modified Kir channels may be purified by a poly-histidine tag-chelating resin (e.g., ProBond™ purification system (Invitrogen, California)) and/or a cysteine-rich tag purification resin (e.g., Lumio® agent (Invitrogen, California) linked to a solid phase. Provided also are arrays comprising one or more, two or more, three or more, etc., Kir channels or modified Kir channels immobilized at discrete sites on a solid support in an ordered array. Such arrays sometimes are high-density arrays, such as arrays in which each spot comprises at least 100 protein molecules per square centimeter. Solid supports include but are not limited to a glass slide, a microchip, a microtiter plate, a chromatography support, a nanotube, and the like. Types of solid supports, linker molecules for covalent and non-covalent attachments to solid supports, and methods for immobilizing nucleic acids, proteins and other molecules to solid supports are known (e.g., U.S. Pat. Nos. 6,261,776; 5,900,481; 6,133,436; and 6,022, 688; and WIPO publication WO 01/18234).

In certain embodiments, a Kir channel, modified Kir channel or agent may be linked to a phage via a phage coat protein. Molecules capable of interacting with the protein or peptide linked to the phage are immobilized to a solid phase, and phages displaying proteins or peptides that interact with the immobilized components adhere to the solid support. Nucleic acids from the adhered phages then are isolated and sequenced to determine the sequence of the protein or peptide that interacted with the components immobilized on the solid phase. Methods for displaying a wide variety of peptides or proteins as fusions with bacteriophage coat proteins are well known (Scott and Smith, Science 249: 386-390 (1990); Devlin, Science 249: 404-406 (1990); Cwirla et al., Proc. Natl. Acad. Sci. 87: 6378-6382 (1990); Felici, J. Mol. Biol. 222: 301-310 (1991)). Methods are also available for linking the test polypeptide to the N-terminus or the C-terminus of the phage coat protein. The original phage display system was disclosed, for example, in U.S. Pat. Nos. 5,096,815 and 5,198, 346. This system used the filamentous phage M13, which required that the cloned protein be generated in E. coli and required translocation of the cloned protein across the E. coli inner membrane. Lytic bacteriophage vectors, such as lambda, T4 and T7 are more practical since they are independent of E. coli secretion. T7 is commercially available and described in U.S. Pat. Nos. 5,223,409; 5,403,484; 5,571,698; and 5,766,905.

In some embodiments, the artisan detects an interaction between Kir channel or modified Kir channel units, sometimes an interaction between one or more of such units with one or more other molecules, and sometimes a modulatory effect of an agent on such interactions. As used herein, the term "interaction" can refer to reversible binding of particular system components to one another, and such interactions can be quantified. Binding affinity can be quantified by plotting signal intensity as a function of a range of concentrations or amounts of a reagent, reactant or other system component. Quantified interactions can be expressed in terms of a concentration or amount of a reagent required for emission of a signal that is 50% of the maximum signal ($IC_{50}$). Quantified interactions can be expressed as a dissociation constant ($K_d$ or $K_i$), and other kinetic parameters can be elucidated (e.g., $K_m$, $k_{cat}$, $k_{on}$, $k_{off}$ parameters) using kinetic methods known in the art.

A variety of signals can be detected to identify the presence, absence or amount of an interaction. A signal from a detectable label linked to an assay component before or after the components are contacted with one another may be detected. A detectable label can be covalently linked to an assay component, and sometimes is in association with an assay component in a non-covalent linkage. Non-covalent linkages can be effected by a binding pair, in which one binding pair member is in association with an assay component and the other binding pair member is in association with the detectable label. Any suitable binding pair can be utilized to effect a non-covalent linkage, including, but not limited to, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA). Covalent linkages also can be effected by a binding pair, such as a chemical reactive group/complementary chemical reactive group (e.g., sulfhydryl/maleimide, sulfhydryl/haloacetyl derivative, amine/isotriocyanate, amine/succinimidyl ester, and amine/sulfonyl halides). Methods for attaching such binding pairs to reagents and effecting binding are known to the artisan.

Any detectable label suitable for detection of an interaction or biological activity in a system can be appropriately selected and utilized by the person of ordinary skill in the art. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., $^{125}I$, $^{131}I$, $^{35}S$, $^{31}P$, $^{32}P$, $^{33}P$, $^{14}C$, $^{3}H$, $^{7}Be$, $^{28}Mg$, $^{57}Co$, $^{65}Zn$, $^{67}Cu$, $^{68}Ge$, $^{82}Sr$, $^{83}Rb$, $^{95}Tc$, $^{96}Tc$, $^{103}Pd$, $^{109}Cd$, and $^{127}Xe$); light scattering labels (e.g., U.S. Pat. No. 6,214,560); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and the like.

A change in refractive index at a solid optical surface, where the change is caused by the binding or release of a refractive index enhancing molecule near or at the optical surface, is another type of signal that can be detected as a measure of component interaction. These methods for determining refractive index changes of an optical surface are based upon surface plasmon resonance (SPR). SPR is observed as a dip in light intensity reflected at a specific angle from the interface between an optically transparent material (e.g., glass) and a thin metal film (e.g., silver or gold). SPR depends upon the refractive index of the medium (e.g., a sample solution) close to the metal surface. A change of refractive index at the metal surface, such as by the adsorption or binding of material near the surface, will cause a corresponding shift in the angle at which SPR occurs. SPR signals and uses thereof are further exemplified in U.S. Pat. Nos. 5,641,640; 5,955,729; 6,127,183; 6,143,574; and 6,207,381, and WIPO publication WO 90/05295 and apparatuses for measuring SPR signals are commercially available (Biacore, Inc., Piscataway, N.J.). In certain embodiments, protein reagent can be linked via a linker to a chip having an optically transparent material and a thin metal film, and interactions between and/or with the reagents can be detected by changes in refractive index.

Other signals representative of structure may also be detected, such as NMR spectral shifts (see, e.g., Arthanari & Bolton, Anti-Cancer Drug Design 14: 317-326 (1999)), mass spectrometric signals and fluorescence resonance energy transfer (FRET) signals (e.g., Lakowicz et al., U.S. Pat. No. 5,631,169; Stavrianopoulos et al. U.S. Pat. No. 4,868,103). In FRET approaches, a fluorophore label on a first, "donor" molecule is selected such that its emitted fluorescent energy will be absorbed by a fluorescent label on a second, "acceptor" molecule, which in turn is able to fluoresce due to the absorbed energy. Alternately, the "donor" polypeptide molecule may simply utilize the natural fluorescent energy of tryptophan residues. Labels are chosen that emit different wavelengths of light, such that the "acceptor" molecule label may be differentiated from that of the "donor". Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FRET binding event can be conveniently measured using standard fluorometric detection means well known (e.g., using a fluorimeter). Molecules useful for FRET are known (e.g., fluorescein and terbium). FRET can be utilized to detect interactions in vitro or in vivo.

Other types of signals bearing on Kir channel activity are electrophysioloical signals that detect and can quantify ion transport (e.g., electrophysiological assays described herein). Such signals can be monitored in a heterogenous or homogenous format.

A Kir channel activity determination may include one or more separation processes. Multiple separation processes are available, such as gel electrophoresis, sedimentation (e.g., gradient sedimentation) and flow cytometry processes, for example. Flow cytometry processes include, for example, such as flow microfluorimetry (FMF) and fluorescence activated cell sorting (FACS); U.S. Pat. Nos. 6,090,919 (Cormack, et al.); 6,461,813 (Lorens); and 6,455,263 (Payan)). In some embodiments, cells also may be washed of unassociated detectable label, and detectable label associated with cellular components may be visualized (e.g., by microscopy).

Agents identified as having a modulatory effect on a Kir channel activity can be analyzed and compared to one another (e.g., ranked). Provided are compositions of agents identified as a Kir activity modulators, as well as pharmaceutical compositions comprising such agents and a pharmaceutically acceptable carrier. Included also within the scope of the invention is information descriptive of agents that modulate a Kir channel activity, and methods of using such agents. Accordingly, provided is structural information descriptive of an agent identified by a method described herein as modulating a Kir channel activity. In certain embodiments, information descriptive of molecular structure (e.g., chemical formula or sequence information) sometimes is stored and/or renditioned as an image or as three-dimensional coordinates. The information often is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

The presence, absence or amount of one or more Kir channel activities can be identified for two or more Kir channels and compared for each channel. In certain embodiments, a first channel contains unmodified monomers or unmodified subunits in a multimer. In some embodiments, a second channel, or subsequent channel, includes one or more modified monomers or modified subunits in a multimer. The channels may be full-length channel subunits or truncated channel subunits in some embodiments. In certain embodiments, a subunit includes one or more modifications in a pore region, and in some embodiments, includes one or more modifications in an alcohol binding pocket. Such Kir channels can be utilized in part for methods of identifying an agent that modulates an inwardly rectifying potassium (Kir) channel activity at a particular site on the Kir channel, which comprise: (a) contacting an unmodified Kir channel protein and at least one modified Kir channel protein with an agent, where each modified Kir channel protein binds an alcohol with lower affinity than the unmodified Kir channel protein, and (b) detecting a Kir channel activity of the unmodified Kir channel protein and the modified Kir channel protein, whereby the agent is identified as an agent that modulates the Kir channel activity at a particular site based on a comparison of the activity of the unmodified Kir channel protein relative to activity of the modified Kir channel protein. In an embodiment, agent binding is assessed for three channels: (i) a channel comprising a modification in the pore region that modulates alcohol binding, (ii) a channel comprising a modification in the alcohol binding pocket that modulates binding of the alcohol, and (iii) a channel that does not include the modifications of (i) and (ii) and binds the alcohol better than (i) and (ii) (e.g., binds an alcohol with an affinity similar to native protein). In the foregoing embodiment, an agent that binds to (i) and (iii), and binds with lower affinity to (ii), is identified as an agent that binds to the pore region.

Compositions and Crystals

Provided herein are compositions of matter comprising an inwardly rectifying potassium (Kir) channel protein, or a modified Kir channel protein having an alcohol-binding site, and an alcohol, where the alcohol comprises four or more carbon atoms, and/or the alcohol comprises two or more hydroxyl moieties. Also provided are compositions of matter comprising a modified inwardly rectifying potassium (Kir) channel protein having an alcohol-binding site and an alcohol. In certain embodiments, the modified Kir channel lacks a functional transmembrane region, and optionally lacks an N-terminal region and/or a C-terminal region outside of the channel domain. Alcohol embodiments and Kir channel modification embodiments are described herein. Also provided are compositions comprising an alcohol defined herein, as well as pharmaceutical compositions comprising such alcohols and a pharmaceutically acceptable carrier.

Kir channels and modified Kir channels sometimes are provided in crystalline form. Protein crystals can be produced from highly concentrated solutions of a protein (e.g., saturated or supersaturated solutions). Such solutions may be restored to equilibrium by reducing the polypeptide concentration, preferably through precipitation of the polypeptide crystals. Thus, provided is solution comprising a concentrated amount of a Kir channel or modified Kir channel. Proteins may be induced to crystallize from supersaturated solutions by adding agents that alter the protein surface charges or perturb the interaction between the polypeptide and bulk media to promote associations that lead to crystallization. Compounds known as "precipitants" often are used to decrease the solubility of the polypeptide in a concentrated solution by forming an energetically unfavorable precipitating layer around the polypeptide molecules (Weber, Adv. Prot. Chem. 41:1-36 (1991)). In addition to precipitants, other materials are sometimes added to the polypeptide crystallization solution. These include buffers to adjust the pH of the solution and salts to reduce the solubility of the polypeptide. Various precipitants are known in the art and include, for example, ethanol, 3-ethyl-2-4 pentanediol, certain polyglycols, such as polyethylene glycol, and the like.

Commonly used polypeptide crystallization methods include, for example, batch, hanging drop, seed initiation, and dialysis methods. In each of these methods, continued crystallization is promoted after nucleation by maintaining a supersaturated solution. In the batch method, the polypeptide can be mixed with precipitants to achieve supersaturation, the vessel sealed, and set aside until crystals appear. In a dialysis method, the polypeptide is retained in a sealed dialysis membrane that is placed into a solution containing precipitant. Equilibration across the membrane increases the polypeptide and precipitant concentrations thereby causing the polypeptide to reach supersaturation levels.

In hanging drop techniques (McPherson, J. Biol. Chem. 251:6300-6303 (1976)), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization involves introducing a nucleation site into a concentrated polypeptide solution. Generally, a concentrated polypeptide solution is prepared and a seed crystal of the polypeptide is introduced into this solution. If the concentrations of the polypeptide and of any precipitants are correct, the seed crystal will provide a nucleation site around which a larger crystal forms.

Some proteins may be resistant to crystallization. However, several techniques are available to the person of ordinary skill in the art. Removal of polypeptide segments at the amino or carboxy terminal end of a protein facilitates production of crystalline protein samples. Such procedures can involve treatment of the protein with one of several proteases including trypsin, chymotrypsin, subtilisin, and the like. This treatment can result in the removal of flexible polypeptide segments likely to negatively affect crystallization. Alternatively, removal of coding sequences from the gene encoding the protein to be crystallized facilitates the recombinant expression of shortened proteins that can be screened for crystallization. In certain embodiments, N-terminal and C-terminal regions outside the channel domain are removed from the Kir channel by modifying the nucleic acid that encodes the channel, as described herein.

Crystals produced by such techniques have a wide range of uses. For example, high quality crystals are suitable for X-ray or neutron diffraction analysis to determine a three-dimensional structure of a Kir channel, to design mutants thereof, to determine ligand binding properties and pharmacokinetics thereof, and the like. In addition, crystallization can serve as a further purification method. In some instances, a polypeptide or protein will crystallize from a heterogeneous mixture into crystals. Isolation of such crystals by methods known in the art, for example, filtration, centrifugation, and the like, followed by re-dissolving the polypeptide affords a purified solution suitable for use in growing the high-quality crystals needed for diffraction studies. The high-quality crystals also may be dissolved in water and then formulated to provide an aqueous solution having other uses as desired.

Thus, provided is a composition of matter comprising a crystal that includes an inwardly rectifying potassium (Kir) channel protein, or a modified Kir channel protein having an alcohol-binding site, and an alcohol. The term "crystal" or "crystalline form" refers to a crystal of sufficient quality to determine an x-ray crystal structure. A crystal may include one or more other non-protein ligands other than the alcohol, and may include one or more protein binding partners. In certain embodiments, the crystallized Kir channel comprises one or more amino acid mutations, sometimes lacks a portion of the N-terminal region outside of the channel domain, sometimes lacks a transmembrane region, and sometimes lacks a portion of the C-terminus outside of the channel domain. In some embodiments, the Kir channel or modified channel includes a Kir2 sequence, and sometimes a Kir2.1 sequence. The crystal may crystallize in group C2. In certain embodiments a unit cell has dimensions of a is about 140 (e.g., 140.67), b is about 100 (e.g., 98.87) and c is about 100 (e.g., 98.09), where alpha and gamma are about 90 and beta is about 130 (e.g., 130.68). The crystal may be produced by vapor diffusion, sometimes by hanging drops, and may be co-crystallized with an alcohol described herein (e.g., a C4-C10 alcohol containing one or two or more hydroxyl moieties). In certain embodiments, crystals are flash frozen in liquid nitrogen. In some embodiments, the three-dimensional structure resulting from the crystal is at a resolution of 2.5 Å or less, and sometimes about 2.0 Å. The resulting structure sometimes is determined by molecular replacement techniques. Examples of structural coordinates directed to Kir channel structures, include but are not limited to, those accessed by accession nos. 2GIX (Cytoplasmic Domain Structure of Kir2.1 containing Andersen's Mutation R218Q and Rescue Mutation T309K; Release Date: 25 Jul. 2006; Exp. Method: X Ray Diffraction; Resolution: 2.02 Å; Inward rectifier potassium channel 2; Mutation: R218Q, T309K; Chains: A, B, C, D; Authors: Pegan, S., Arrabit, C., Slesinger, P. A., Choe, S.); 1U4F (Crystal Structure of Cytoplasmic Domains of IRK1 (Kir2.1) channel; Release Date: 8 Mar. 2005; Exp. Method: X Ray Diffraction; Resolution: 2.41 Å; Molecule: Inward rectifier potassium channel 2; Fragment: Cytoplasmic domain; Chains: A, B, C, D; Authors: Pegan, S., Arrabit, C., Zhou, W., Kwiatkowski, W., Collins, A., Slesinger, P. A., Choe, S.) and 1U4E (Crystal Structure of Cytoplasmic Domains of GIRK1 channel; Release Date: 8 Mar. 2005; Exp. Method: X Ray Diffraction; Resolution: 2.09 Å; Molecule: G protein-activated inward rectifier potassium channel 1; Fragment: Cytoplasmic domain; Chains: A; Authors: Pegan, S., Arrabit, C., Zhou, W., Kwiatkowski, W., Collins, A., Slesinger, P. A., Choe, S.), at World Wide Web URL "www.rcsb.org/pdb/."

Methods of Using Kir Channel Structures

In some embodiments, provided are methods for utilizing structure coordinates obtained by X-ray crystallography of crystals comprising a Kir channel or modified Kir channel and an alcohol. In certain embodiments, the methods include utilizing information obtained from high-resolution structures of a modified Kir channel and an alcohol.

Because Kir channels or modified Kir channels may crystallize in more than one crystal form, the structure coordinates provided herein are particularly useful for solving the structure of other crystal forms of Kir channels or modified Kir channels, optionally in association with other molecules. In some embodiments, the coordinates of the three dimensional structure defined herein are utilized in molecular replacement techniques to determine the structure from another crystal comprising a Kir channel or modified Kir channel.

Also provided are methods for predicting whether an agent is capable of binding to a Kir channel or modified Kir channel. Such methods can comprise modeling an agent that potentially interacts with the alcohol-binding site of a Kir channel or modified Kir channel, where the alcohol-binding site is defined by structure coordinates of the alcohol-binding site or fragment thereof of a Kir channel, and where the structure coordinates are derived from crystals of the Kir channel or modified Kir channel complexed with an alcohol. Such methods sometimes include inserting the agent into the three-dimensional structure of the alcohol binding site in silico, which sometimes is referred to as "docking" the agent into the alcohol-binding site structure. The methods also sometimes include determining the fit of the agent in the alcohol-binding site structure, and optionally comparing criteria of the fit of the agent compared to other molecules. Fit criteria are known in the art and methods for determining fit also are known. In certain embodiments, an energy minimization algorithm is performed after the agent is inserted into the alcohol-binding site structure, and the energy minimum is quantified. Energy minimization algorithms can allow certain portions of the binding site—agent structure to re-position and adopt a more favorable orientation. Sometimes the energy minimum of the binding site—agent structure is compared to the energy minimum of a reference structure, such as a binding site—alcohol structure (e.g., the energy minimum with MPD docketed in the alcohol-binding site), for example. Upon said comparison, a fit of an agent is determined a "comparable fit" or "favorable fit" if the energy minimum of the binding site—agent structure is similar to or lower than the energy minimum of the reference structure, for example.

Tools and computer programs useful for determining three-dimensional structures from crystallographic x-ray diffraction patters and performing structural analysis are known to the person of ordinary skill in the art. Examples of such tools and algorithms are set forth in U.S. Patent Application Publication No. 20060194949, published Aug. 31, 2006, entitled "Structure of the farnesoid x receptor ligand binding domain and methods of use therefore" (Downes et al.).

Agents leading to a structure having favorable binding properties (e.g., displaying a similar, or a lower, energy minimum as compared to the reference structure) sometimes are tested further. Further testing can determine whether an agent interacts favorably with a Kir channel or modified Kir channel, and sometimes an agent is tested to determine whether it modulates a Kir channel activity. Examples of such assays are described herein. Also provided are compositions of agents identified by such methods, as well as pharmaceutical compositions comprising such agents and a pharmaceutically acceptable carrier. Thus, such methods can be used to identify agents in silico that can bind to Kir channels, and therefore identify new activators and new inhibitors of a Kir channel activity.

Kir Channel Nucleic Acids

Kir channel and modified Kir channel proteins can be produced from nucleic acids, also referred to herein as "nucleic acid reagents," which can be included in a kit described hereafter. A nucleic acid reagent can be from any source or composition, such as DNA, cDNA, RNA or mRNA, for example, and can be in any form (e.g., linear, circular, supercoiled, single-stranded, double-stranded, and the like). A nucleic acid reagent sometimes is a plasmid, phage nucleic acid, autonomously replicating sequence (ARS), centromere, artificial chromosome or other nucleic acid able to replicate or be replicated in vitro or in a host cell. Such nucleic acid reagents are selected for their ability to guide production of the desired protein or nucleic acid molecule. When desired, the nucleic acid reagent can be altered as known in the art such that codons encode for a different amino acid than is normal, including unconventional or unnatural amino acids (including detectably labeled amino acids).

A nucleic acid reagent can comprise certain elements that can be selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and a selection element. A nucleic acid reagent is provided with one or more of such elements and other elements may be inserted into the nucleic acid before the template is inserted or contacted with an transcription and/or translation system (e.g., in vitro or in vivo transcription/translation). In some embodiments, a provided nucleic acid reagent comprises a promoter, 5'UTR, optional 3'UTR and insertion element(s) by which a target nucleotide sequence is inserted (i.e., cloned) into the template. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for target protein production, and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter often interacts with a RNA polymerase, an enzyme that catalyses synthesis of nucleic acids using a preexisting nucleic acid. When the template is a DNA template, an RNA molecule is transcribed before protein is synthesized. Enzymes having polymerase activity suitable for use in the present methods include any polymerase that is active in the chosen system with the chosen template to synthesize protein. Certain promoters that can be utilized are of viral origin. Certain promoters are tissue specific and drive expression of the target sequence only in specific tissues. Such sequences are readily accessed by the artisan, such as by searching one or more public or private databases, for example, and the sequences are readily adapted to nucleic acid reagents described herein.

A 5' UTR may comprise one or more endogenous elements and may include one or more exogenous elements with respect to the nucleic acid reagent backbone or target sequence. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the transcription and/or translation system being utilized. A 5' UTR sometimes comprises one or more of the following elements known to the artisan: translational enhancer sequence, transcription initiation site, transcription factor binding site, translation regulation site, translation initiation site, translation factor binding site, ribosome binding site, replicon, enhancer element, internal ribosome entry site (IRES), and silencer element.

A 3' UTR may comprise one or more endogenous elements and may include one or more exogenous elements with respect to the nucleic acid reagent backbone or target sequence. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the transcription and/or translation system being utilized. A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

The target sequence in the nucleic acid is expressed and generally includes a Kir channel-encoding or modified Kir channel-encoding nucleotide sequence. The target sequence optionally includes other elements. The target nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). An ORF may be from any suitable source, sometimes from genomic DNA, mRNA, reverse transcribed RNA or complementary DNA (cDNA) or a nucleic acid library comprising one or more of the foregoing.

A nucleotide sequence encoding an amino acid tag sometimes is an optional sequence within the target sequence. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG (SEQ ID NO: 11)), V5 (e.g., GKPIPNPLLGLDST (SEQ ID NO: 12)), c-MYC (e.g., EQKLISEEDL (SEQ ID NO: 13)), HSV (e.g., QPELAPEDPED (SEQ ID NO: 14)), influenza hemagglutinin, HA (e.g., YPYDVPDYA (SEQ ID NO: 15)), VSV-G (e.g., YTDIEMNRLGK (SEQ ID NO: 16)), bacterial glutathione-S-transferase, maltose binding protein, a streptavidin- or avidin-binding tag, thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 17) or His8 (SEQ ID NO: 18)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 19), wherein X is any amino acid and n is 1 to 3, and the cysteine-rich sequence sometimes is CCPGCC (SEQ ID NO: 20). In certain embodiments, the tag comprises a cysteine-rich element and a polyhistidine element (e.g., CCPGCC (SEQ ID NO: 20) and His6 (SEQ ID NO: 17)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3, 2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide, as described in greater detail hereafter.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the cells from which a cell-free extract is prepared. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondria targeting signal (e.g., amino acid sequence that forms an amphipathic helix); peroxisome targeting signal (e.g., C-terminal sequence in YFG from S. cerevisiae); and a secretion signal (e.g., N-terminal sequences from invertase, mating factor alpha, PHO5 and SUC2 in S. cerevisiae; multiple N-terminal sequences of B. subtilis proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470, 719); lam beta signal sequence (e.g., U.S. Pat. No. 5,389, 529); B. brevis signal sequence (e.g., U.S. Pat. No. 5,232, 841); and P. pastoris signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to a the ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I(E/D)GR), thrombin (e.g., recognition site LVPRGS (SEQ ID NO: 21)), enterokinase (e.g., recognition site DDDDK (SEQ ID NO: 22)), TEV protease (e.g., recognition site ENLYFQG (SEQ ID NO: 23)) or PreScission™ protease (e.g., recognition site LEVLFQGP (SEQ ID NO: 24)), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons.

Any convenient cloning strategy known to the artisan may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example. Other insertion sites include, but are not limited to, topoisomerase insertion sites and recombinase insertion sites (e.g., loxP for Cre recombinase; attB, attP, attL, and attR sequences, and mutants, fragments, variants and derivatives thereof, which are recognized by the recombination protein λ Int and by the auxiliary proteins integration host factor (IHF), FIS and excisionase (Xis)).

A nucleic acid reagent sometimes contains one or more origin of replication (ORI) elements, and sometimes contains one or more transcription regulation sites. A nucleic acid reagent often includes one or more selection elements. Selection elements often are utilized using known processes to determine whether a nucleic acid reagent is included in a cell (e.g., antibiotic resistance, fluorescent protein gene detection).

A Kir channel or modified Kir channel protein can be produced from a nucleic acid reagent using expression techniques known to the person of ordinary skill in the art. Several methods are known to the artisan for transferring nucleic acid reagents into cells for expression of the Kir channel or modified Kir channel, which methods are known as transfection and transduction. The terms "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like. Several expression systems are known to and can be selected by the person of ordinary skill in the art, and elements of the nucleic acid reagent generally are selected based upon the intended expression system. For example, expression systems may be selected for particular cell types that include, but are not limited to, bacterial cells (e.g., *Escherichia* spp. cells (e.g., Expressway™ HTP Cell-Free *E. coli* Expression Kit, Invitrogen, California) such as DH10B, Stb12, DH5-alpha, DB3, DB3.1 for example), DB4, DB5, JDP682 and ccdA-over (e.g., U.S. application Ser. No. 09/518,188), *Bacillus* spp. cells (e.g., *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells); photosynthetic bacteria (e.g., green non-sulfur bacteria (e.g., *Choroflexus* spp. (e.g., *C. aurantiacus*), *Chloronema* spp. (e.g., *C. gigateum*)), green sulfur bacteria (e.g., *Chlorobium* spp. (e.g., *C. limicola*), *Pelodictyon* spp. (e.g., *P. luteolum*), purple sulfur bacteria (e.g., *Chromatium* spp. (e.g., *C. okenii*)), and purple non-sulfur bacteria (e.g., *Rhodospirillum* spp. (e.g., *R. rubrum*), *Rhodobacter* spp. (e.g., *R. sphaeroides, R. capsulatus*), *Rhodomicrobium* spp. (e.g., *R. vanellii*)); yeast cells (e.g., *Saccharomyces cerevisiae* cells and *Pichia pastoris* cells); insect cells (e.g., *Drosophila* (e.g., *Drosophila melanogaster*), *Spodoptera* (e.g., *Spodoptera frugiperda* Sf9 and Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells). These and other suitable cells are available commercially, for example, from Invitrogen Corporation, (Carlsbad, Calif.), American Type Culture Collection (Manassas, Va.), and Agricultural Research Culture Collection (NRRL; Peoria, Ill.). In vitro transcription and translation systems also may be selected by the person of ordinary skill in the art. Post expression, the Kir channel protein or modified Kir channel protein can be optionally isolated or purified.

Kits

Kits comprise one or more containers that include one or more of the compositions and/or components described herein. A kit comprises one or more of the components in any number of separate containers, packets, tubes, vials, microtiter plates and the like, or the components may be combined in various combinations in such containers. A kit can comprise a Kir channel or modified Kir channel protein, alcohol, one or more agents or nucleic acid reagent.

A kit can include components described herein in any combination. A kit may comprise one, two, three, four, five or more components described herein. For example, a kit can include (1) a Kir channel or modified Kir channel protein described herein; (2) a nucleic acid reagent that encodes a channel of (1); (3) a Kir channel or modified Kir channel in combination with a detectable label; (4) an alcohol; (5) an alcohol in combination with a detectable label; (6) components for crystallizing a channel of (1); and other combinations of components described herein.

A kit sometimes is utilized in conjunction with a method, and sometimes includes instructions for performing one or more methods and/or a description of one or more compositions or reagents. Instructions and/or descriptions may be in printed form and may be included in a kit insert. A kit in some embodiments includes one or more components described herein and instructions that direct the user to another component not included in the kit. A kit also may include a written description of an internet location that provides such instructions or descriptions.

EXAMPLES

The following examples illustrate but do not limit the invention. Kir2.1 channels play a role in maintaining the correct resting potential in eukaryotic cells. Recently, specific amino acid mutations in the Kir2.1 inwardly rectifying potassium channel have been found to cause Andersen's Syndrome in humans. Here, individual Andersen's Syndrome mutants R218Q, G300V, E303K, and delta 314-315 are analyzed and multiple effects on the ability of the cytoplasmic domains in Kir2.1 channels to form proper tetrameric assemblies are identified. For the R218Q mutation, a second site mutation (T309K) also was identified that restored tetrameric assembly but not function. The Kir channels were successfully crystallized and structures of the N- and C-terminal cytoplasmic domains of Kir2.1-R218Q/T309KS were solved (at 2.0 Å). This new structure revealed multiple conformations of the G-loop and CD loop, providing an explanation for channels that assemble but do not conduct ions. Glu303 forms both intra and inter-subunit salt bridges depending on the conformation of the G-loop, suggesting that E303K mutant stabilizes both closed and open G-loop conformations. In the Kir2.1-R218Q/T309KS structure, it was discovered that the DE loop forms a hydrophobic pocket that binds 2-methyl-2, 4-pentanediol, which is located near the putative G beta gamma-activation site of Kir3 channels. Finally, a potassium ion bound to the cytoplasmic domain for this class of K channels was observed.

Andersen's Syndrome (AS) is a rare autosomal disorder in which patients exhibit electrophysiological symptoms of periodic paralysis, a prolonged QT interval, and ventricular arrhythmias[1, 2]. Also present in AS individuals are distinct physical abnormalities that include low-set ears, clinodactyl), scoliosis, hypertelorism, and micrognathia [1, 3-5]. AS has been directly linked to the Kir2.1 inwardly rectifying potassium channel [4, 5]. Point mutations occurring at one of 15 sites and two internal deletions in Kir2.1 channels have been found in patients with AS (FIG. 1) [1-4, 6, 7]. Despite their important physiological roles, the structural basis underlying molecular mechanisms of functional disorders caused by these specific mutations leading to AS have remained poorly understood. The ability of Kir2 subunits to assemble with AS-affected Kir2.1 subunits and restore surface expression without ion-conducting function has been a subject of recent discussion. Non-conducting hetero-tetramers containing AS-affected Kir2.1 subunits indicate that the AS-affected Kir2.1 subunits provide a dominant negative effect on the channels [5]. Furthermore, a recent report showed that AS-affected Kir2.1 channels carrying mutants: D71V, delta 95-98, S136F, G144S, N216H, R218Q, G300V, V302M, E303K, and delta 314-315, were largely incapable of reaching the membrane by themselves; but G144S, N216H, G300V, and E303K could be transported successfully if co-expressed with wild-type (wt) Kir2.1 [21]. Nevertheless, these channels were all non-conducting like the hetero-tetrameric Kir2.x channels containing AS-affected Kir2.1 subunits [5, 21](but see [2]). The loss of functional Kir2 channels on the membrane can clearly alter membrane excitability in many tissues, such as in heart [22].

The mechanism by which wild-type Kir2.1 and Kir2.3 channels recover surface expression with some AS-affected Kir2.1 channel subunits but impair channel activity is not well understood. Based on the structure of the N-terminal and C-terminal domains of wild-type Kir2.1 at 2.4 Å [14], it was previously proposed that AS mutations could interfere with the function of the G-loop and thereby alter gating. Based on electrophysiological studies of full-length channels, the flexibility of the pore-facing G-loop appeared to be essential for proper channel function [14]. Alternatively, it was suggested that some of these AS mutations such as R218Q may interfere with the ability of the channel to form a tetramer. In the present study, biochemical techniques were used to probe how four cytoplasmic AS mutations in Kir2.1, R218Q, G300V, E303K, and delta 314-315, impact the stability of functional tetrameric channels. For one mutation, R218Q, it has been determined that a second site mutation, T309K, can rescue tetrameric assembly but does produce functional channels. The atomic structure of the Kir2.1 cytoplasmic domain containing two mutations, R218Q and T309K, is described, which provides additional evidence implicating the G-loop in gating and tetrameric assembly. In the course of this study, a novel ligand bound to a biologically relevant site in the C-terminal domain was identified. The 2.0 Å structure also places a single potassium ion in the cytoplasmic domain of the ion-permeation pathway, which may affect $K^+$ permeation.

Example 1

Experimental Procedures

Molecular Biology and Protein Purification.

Fusion constructs Kir2.1S, N-terminal (44-64) and C-terminal (189-371), and Kir2.1L, N-terminal (44-64) and C-terminal (189-428), were generated from mouse Kir2.1 (FIG. 1) and linked through 2-step PCR prior to being cloned into an octa-histidine (SEQ ID NO: 18) expression vector modified from pet28a (Invitrogen). Andersen's Syndrome mutations were incorporated via Quick-Change Site-directed Mutagenesis Kit (Stratagene).

Kir2.1 mutants were grown in Terrific Broth at 37 degrees C. to the OD600 of 0.6, then induced with 0.5 mM IPTG for 3 hours prior to harvesting. Cells were lysed in 0.5M NaCl, 20 mM Tris-HCl pH 8.5, 10% glycerol, 7 mM beta-mercaptoethanol, 0.1 mM PMSF, 10 mM imidazole and 0.5 mg lysozyme per 100 ml of lysate. The lysate was sonicated and spun at 94,000 G for 45 minutes. The supernatant was loaded on a 2 ml-packed nickel affinity column (Qiagen), washed with 5 ml of lysis buffer without PMSF, and then eluted with lysis buffer with 250 mM imidazole. Thrombin was added to the eluted fraction and it was dialyzed against the sizing column buffer, 150 mM NaCl, 5 mM Tris-HCl pH 8.5, 2 mM DTT. Kir2.1 was then purified by S200 Sepharose chromatography and concentrated to 10 mg/ml with 10 mM DTT. Kir2.1 proteins were loaded on a G4000PWXL HPLC column (TOSOH) equilibrated in 150 mM NaCl, 5 mM Tris-HCl 8.5, 2 mM DTT. Molecular weight (MW) of the tetramer complex was calculated by Minidawn static light scattering requiring the use of the extinction coefficient of the monomer. The extinction coefficient was derived from the primary sequence of the protein.

Crystallography.

Kir2.1S-R218Q/T309 (R218Q/T309KS) was crystallized in the space group C2 at 4 degrees C. by vapor diffusion with hanging drops mixed 1:1 with 35% 2-methyl-2,4, pentanediol (MPD), 0.1 M Na/$KPO_4$ pH 6.2, 50 mM NaCl. Crystals were placed in a precipitation solution for 15 seconds prior to flash freezing in liquid nitrogen. Data sets were collected for R218Q/T309KS and R218Q/T309KL at Advanced Light Source (ALS), Berkeley, and Stanford Linear Accelerator Center (SSRL), respectively. Molecular replacement solutions were derived using the model of wild-type Kir2.1L by Phaser. The final model was refined with the 2.0 Å data from R218Q/T309KS by the software CCP4 suite.

Electrophysiology.

Full-length wild-type Kir2.1 (NM_008425.3 cDNA) and the following point mutants, R218Q, T309K, T309R, R218Q/T309R and R218Q/T309K, were constructed in pBSK using PCR [23]. All constructs were confirmed by DNA sequencing. In vitro methyl-capped cRNAs were synthesized from linearized cDNA and transcribed with T3 RNA polymerase (Stratagene). The quality of cRNA was estimated using an ethidium-stained formaldehyde gel. Oocytes were isolated from *Xenopus laevis* frogs as described previously [24]. The experimental procedure was approved by the IACUC at The Salk Institute. Oocytes were injected with a 46 nl solution containing cRNA for the Kir2.1 channels (0.5 to 5 ng) and incubated in ND96 (96 mM NaCl, 2 mM KCl, 1 mM $CaCl_2$, 1 mM $MgCl_2$, 5 mM HEPES, pH 7.6 with NaOH) for 1-4 days at 16 degrees C.

Macroscopic currents were recorded using the two-electrode voltage-clamp method as described previously [24]. Briefly, currents were recorded from oocytes with Geneclamp 500 amplifier (Axon Instruments), filtered at 0.05-2 kHz, digitized (0.1-2 kHz) with a Digidata 1200 A/D interface (Axon Instruments) and stored on a laboratory computer. Electrodes were filled with 3 M KCl and had resistances of 0.6-1 MOhms. Oocytes were perfused continuously with an extracellular "95K" solution (90 mM KCl, 2 mM $MgCl_2$ and 10 mM HEPES; pH 7.5 with ~5 mM KOH), "2K" solution (2 mM KCl, 88 mM NaCl, 2 mM $MgCl_2$ and 10 mM HEPES; pH 7.5 with ~5 mM NaOH) or "95Na" solution (90 mM NaCl, 2 mM $MgCl_2$ and 10 mM HEPES; pH 7.5 with ~5 mM NaOH). The 95Na was used to determine the leakage current and subtracted directly from the currents measured in 95K and 2K. A small chamber (0.125×0.600 in) with fast perfusion was used to exchange the extracellular solution and was connected to ground via a 3 M KCl agarose bridge. Macroscopic currents were elicited with 150 ms voltage-steps from −100 mV to +50 mV. Mutants were studied in 2-3 different batches of oocytes. The current amplitude was measured at the end of a 150 ms step pulse. All values are given as mean±SEM.

Example 2

Structural Characterization and Identification of Alcohol-Binding Site

Effects of AS Mutations on the Assembly of the Cytoplasmic Domains of Kir2.1.

Figure 1E:
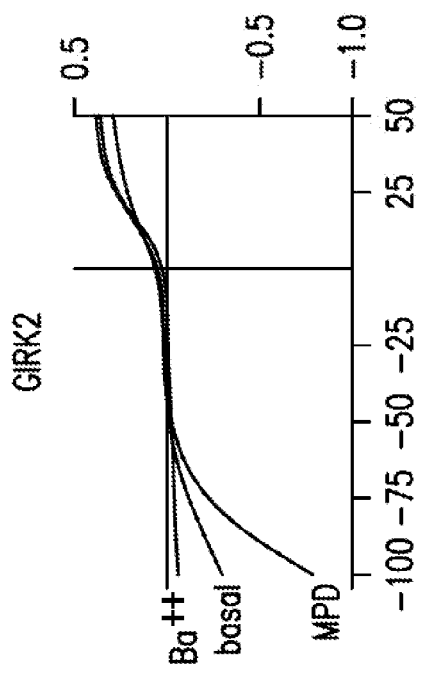

To investigate the effect of specific AS mutation on the tetrameric assembly of the channel, AS mutations, R218Q, G300V, E303K, and delta 314-315, were introduced individually into the Kir2.1L construct (N-terminal 44-64 fused to C-terminal 189-428; FIG. 1). Of these mutants, R218Q, G300V, and E303K were selected on their ability to traffic to the cell membrane when co-expressed with wild-type Kir2.1 and their proposed roles in gating (G300V), forming intra- (R218Q) and inter subunit (E303K) interactions [14, 21]. The delta 314-315 was chosen because it does not allow proper trafficking when co-expressed with wild-type. Each of these mutations has a distinct effect on the quaternary state of the channel's cytoplasmic domains. delta 314-315 in Kir2.1L (delta 314-315L) resulted mostly in mis-folded protein. R218Q (R218QL) produced mildly-larger aggregates (FIG. 2b). Unlike delta 314-315L and R218QL, E303KL produced significant amounts of soluble tetrameric protein. E303KL eluted earlier than wild-type on S200 Sepharose size chromatography (designated as profile 2 in FIG. 2b). The G300VL also eluted to the left of the wild-type reproducibly, but not to the same extent as the E303K, and was designated as profile 1. G300V and E303K without the flexible tail (truncated at position 372 named as Kir2.1S [14]), showed a similar left shift in their elution, indicating that these changes were not caused by the flexible C-terminal tail of Kir2.1L (residues 373-428). Attempts to crystallize G300V and E303K were unsuccessful. However, these results already demonstrate the two Kir2.1 AS mutations cause the cytoplasmic domain to adopt conformations that are distinct from that of the wild-type species.

Figure 2A:
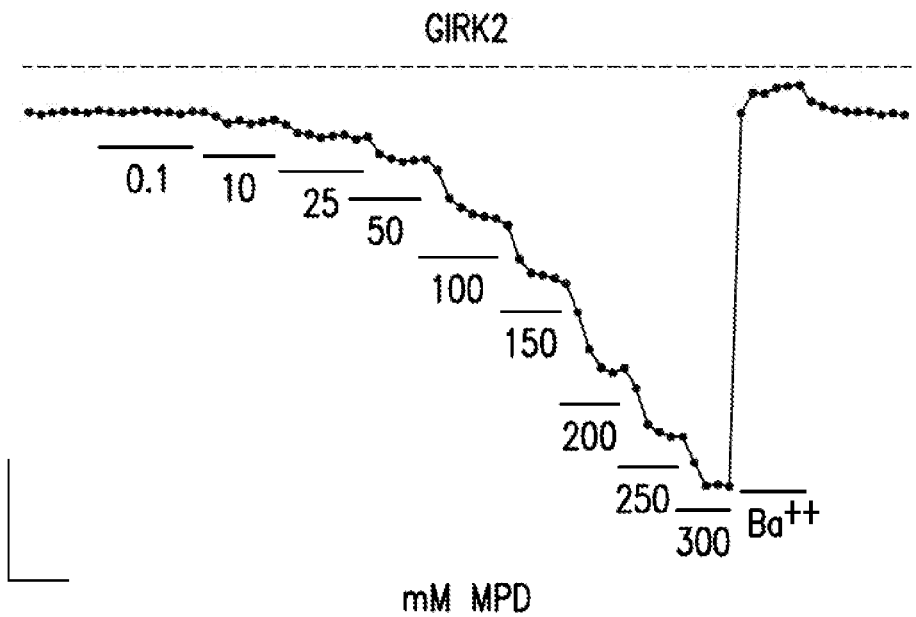
FIGS. 2A-2E show MPD activates GIRK2 in a similar manner to other alcohols.
Figure 2B:
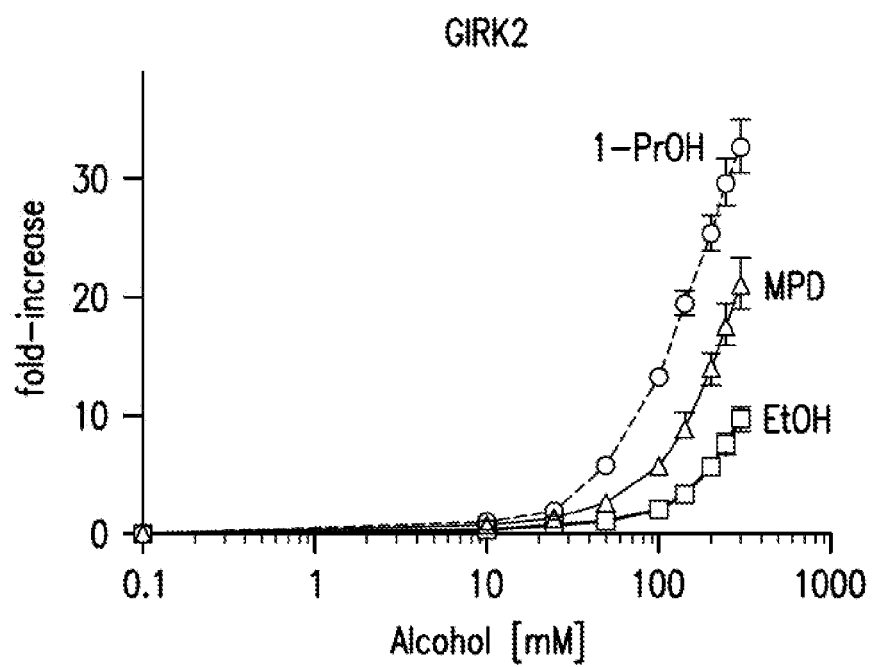
Figure 2C:
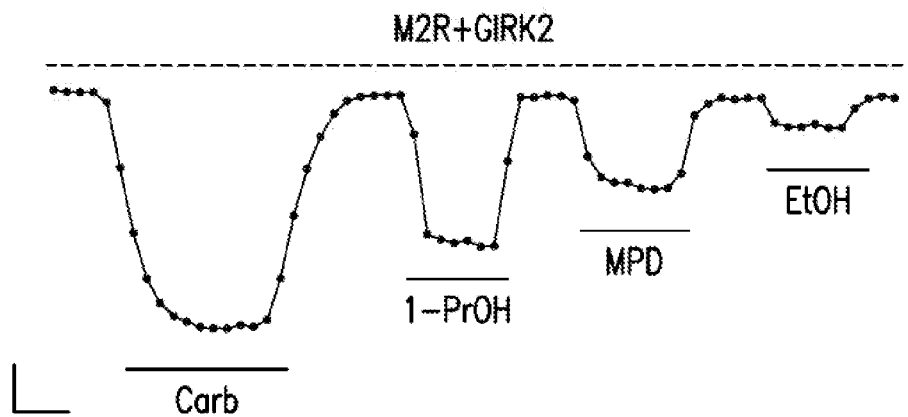
Figure 3:
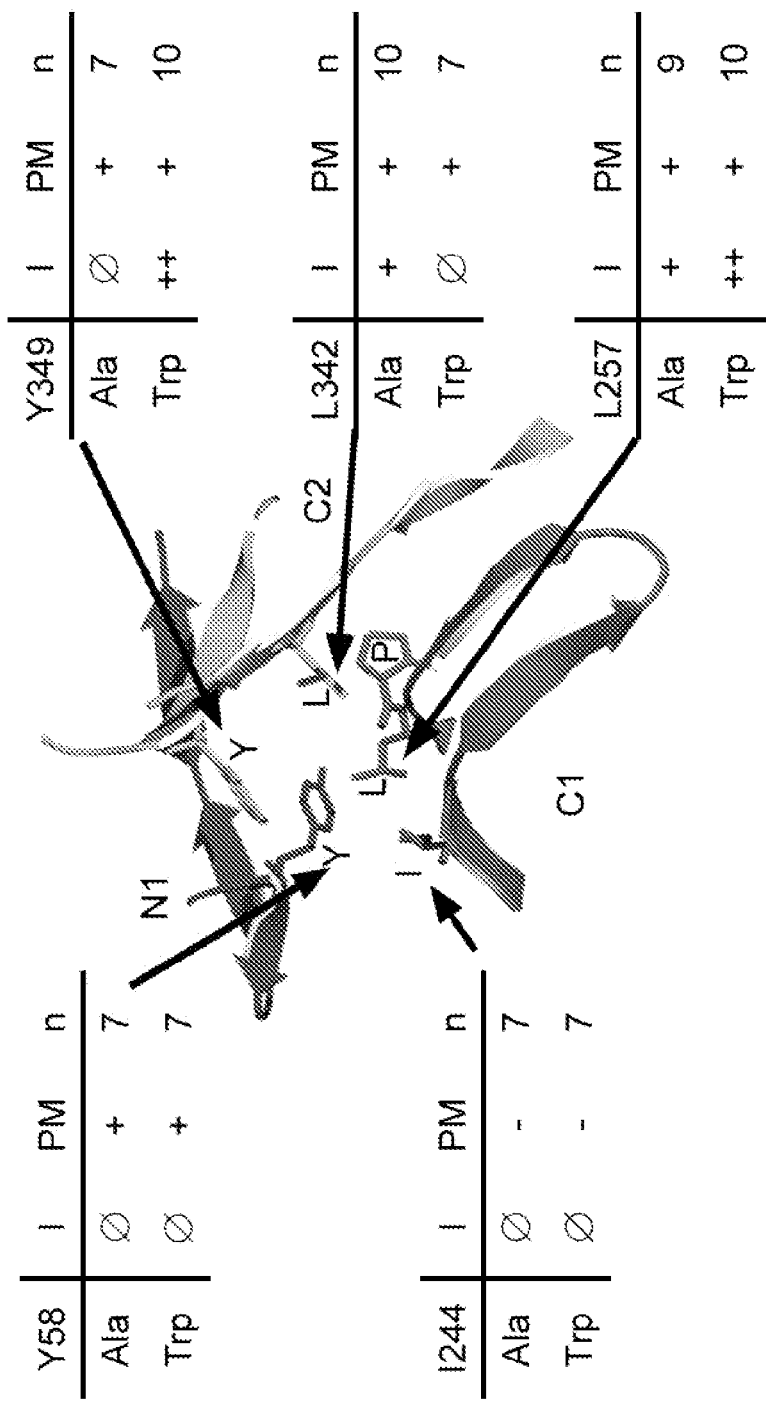
FIG. 3 shows results of a Ala/Trp scan of the MPD pocket in GIRK2 channel, and is a summary of Ala/Trp mutagenesis, which shows barium blocked inward current density, (I), where ø<1 pA/pF, +<5 pA/pF, ++>5 pA/pF and plasma membrane (PM) indicates presence (+) or absence (−) of detection of extracellular HA-tagged GIRK2 channels.

To understand the nature of the mildly-aggregating R218Q, it was reasoned that changing the Thr309 to a positive charge residue would restore a polar interaction similar to the native one present in Kir2.1 between Arg218 and Thr309 (FIG. 2C). Here, the electrophysiological properties of these mutants were examined. A two-electrode voltage clamp method was used to record macroscopic currents in oocytes injected with cRNA for Kir2.1 or Kir2.1 mutants. It was previously shown that additional change to Lys or Arg at Thr309 could restore the tetrameric assembly of the Kir2.1L [14]. However, both R218Q/T309R and R218Q/T309K did not restore the wild-type current of the channel (FIG. 3). Furthermore, it was apparent from the sizing column that the extent of conformational change in Kir2.1L-R218Q/T309K (R218Q/T309KL) or Kir2.1L-R218Q/T309R(R218Q/T309RL) is similar to G300VL, profile 1, as they both eluted nearly at the same position. These results lead to the idea that these two double mutants share an altered non-functional conformation, as with G300V, that disrupts channel function.

G-Loop Conformation of a Double Mutant R218Q/T309K.

The ability of the R218Q/T309K and R218Q/T309R to restore the native tetrameric state of the cytoplasmic domains, but be trapped in an altered conformation (profile 1; FIG. 2b) and fail to rescue channel function suggests that Arg218 may play a more complex role than just forming a stable tetramer. Furthermore, the G300VL-like profile and proximity of Arg218 to the G-loop structure suggested that mutation of R218Q may be affecting the flexible G-loops in the same way as the G300V mutation. In order to resolve the molecular impact of the R218Q mutation, the x-ray crystal structure of the isolated R218Q/T309KL and R218Q/T309RL proteins were sought. Both R218Q/T309KL and R218Q/T309RL produced crystals in 35% t-butanol; (0.1 M citrate, pH 5.2, 0.2 M MgCl$_2$), in the 14 space group, which diffracted to 6.0 Å in one direction and 4.0 Å in the other. Subsequently, crystals of the R218Q/T309KS lacking the 56 C-terminal residues of Kir2.1L grew in a 35% MPD, 50 mM NaCl, 0.1 M Na/KPO$_4$ condition in the C2 space group, diffracting to 2.0 Å resolution (a=140.67 Å, b=98.82 Å, c=98.09 Å; alpha=90°, beta=130.68°, gamma=90°). The structure of R218Q/T309KS was determined. There is one tetramer per asymmetric unit containing 818 residues, 713 waters, four MPD molecules, and one K+ ion (Table 1).

TABLE 1

| Crystallographic data for R218Q/T309K$_s$ | |
|---|---|
| Data Collection | |
| Protein/data set | R218Q/T309K$_s$ |
| Space group | C2 |
| Cell constants | a = 140.67 |
| | b = 98.87 |
| | c = 98.09 |
| | alpha = gamma = 90 |
| | beta = 130.68 |
| Wavelength (Å) | 1.000 |
| Source | ALS |
| Resolution (Å) | 2.0 |
| Total observations/total reflections | 238256/66107 |
| Completeness (highest-resolution shell) | 99.45 (94.17) |
| I/σ (highest-resolution shell) | 13.4 (2.7) |
| $R_{sym}^a$ | 0.086 |
| Model refinement | |
| Total reflections (reflections for test) | 62743 (3363) |
| $R_{work}(\%)/R_{free}(\%)^b$ | 17.8/23.0 |
| Protein atoms/water atoms | 6546/713 |
| R.m.s. deviation of bond lengths (Å) | 0.018 |
| R.m.s. deviation of bond angles (°) | 1.65 |

$^a R_{sym} = \Sigma_h \Sigma_i |I_i(h) - <I(h)|\Sigma_h \Sigma_i\ I_i(h)$, where $I_i(h)$ is the $i^{th}$ measurement and $<I(h)>$ is weighted mean of all measurements of I(h).
$^b R_{free} = h(|F(h)_{obs}| - |F(h)_{calc}|)/h|F(h)_{obs}|$ for reflections in the working and test sets, respectively.
R.m.s., root mean square.

Figure 4A:
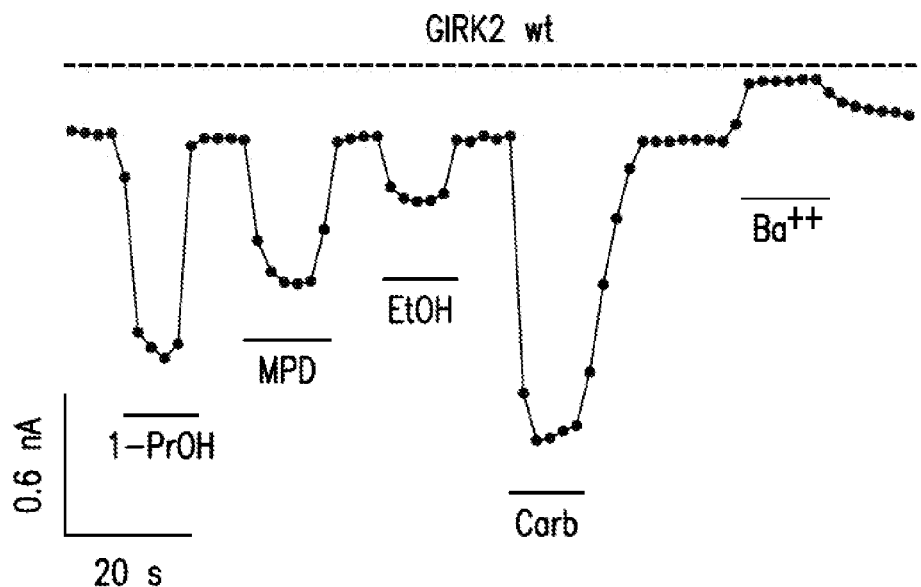
FIGS. 4A-4F show amino acid substitutions at GIRK2 Leu257 leads to alteration of alcohol and Gβγ mediated currents.
Figure 4B:
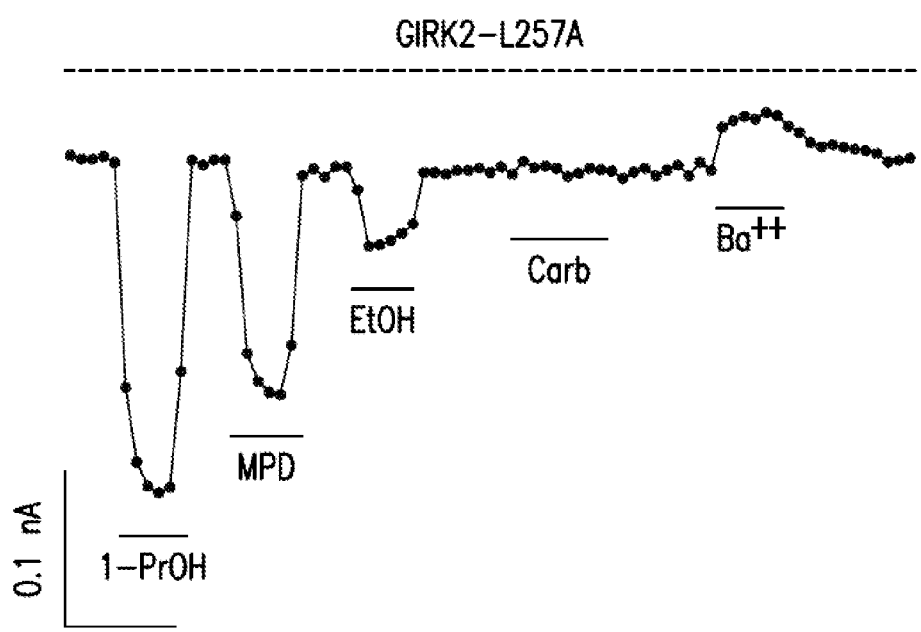
Figure 4C:
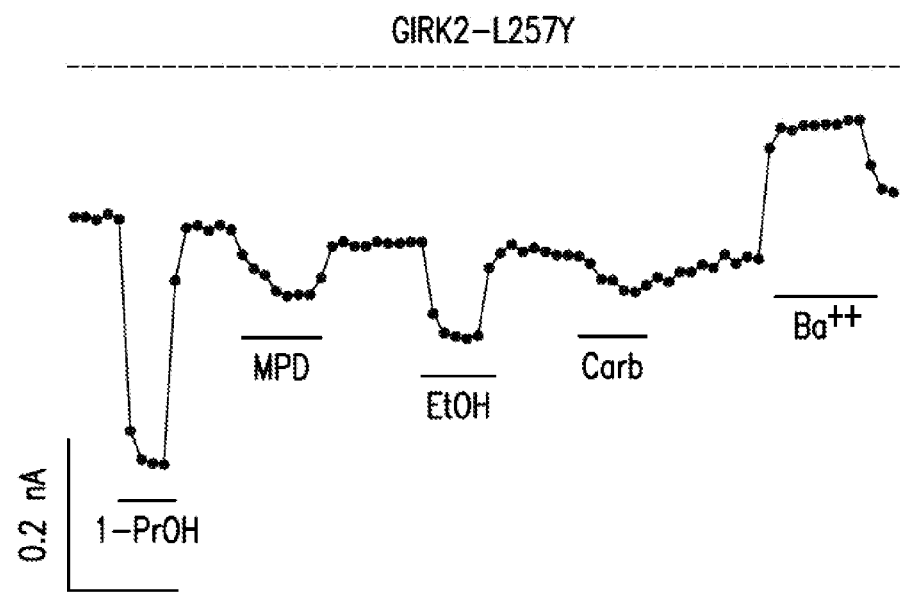
Figure 4D:
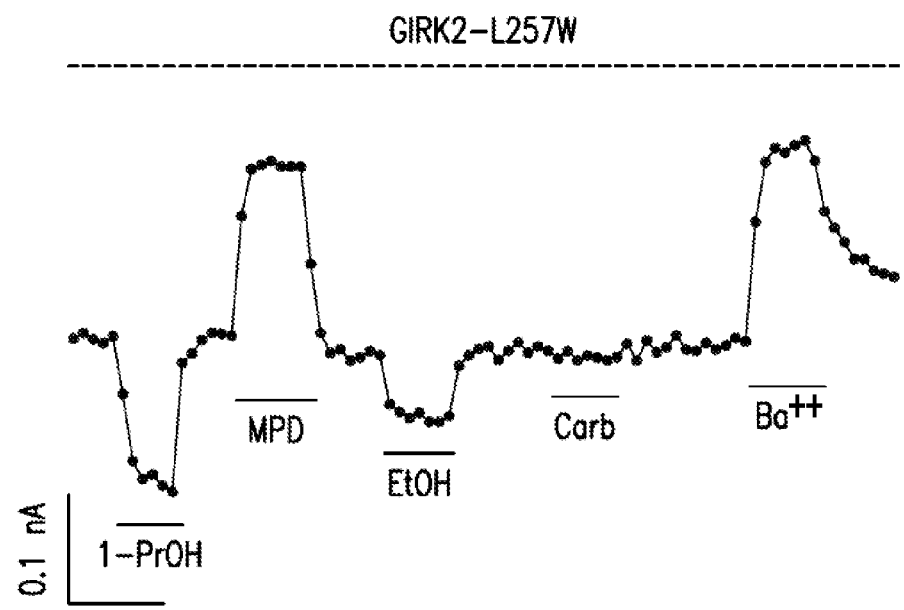
Figure 4E:
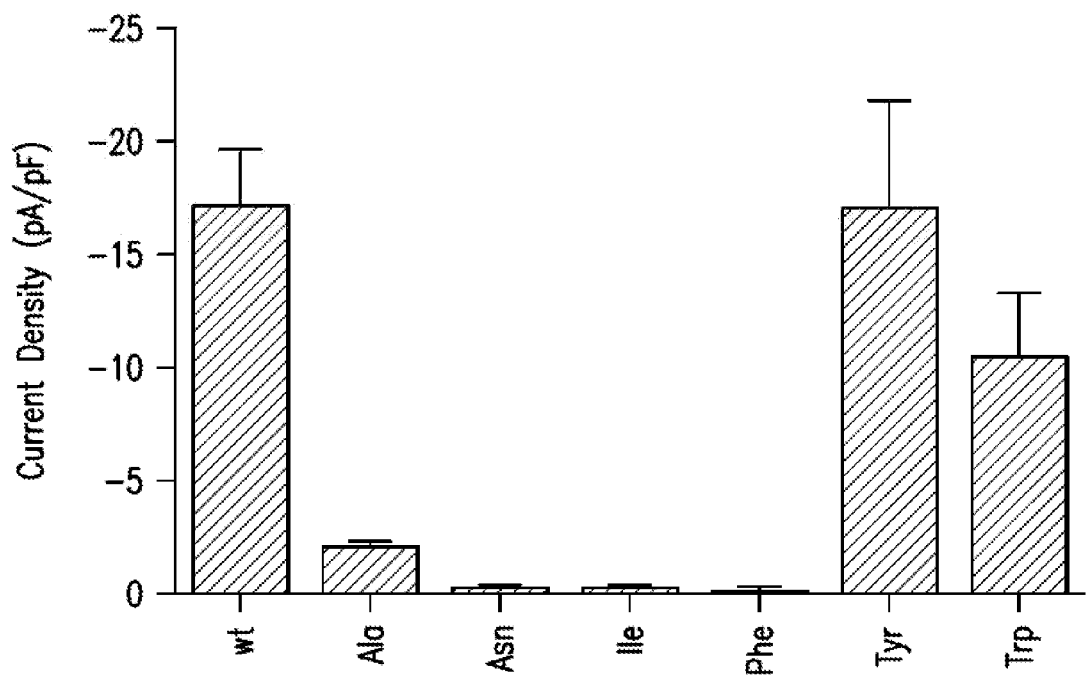

The overall scaffold of R218Q/T309KS is similar to that of the wild-type Kir2.1L (FIGS. 4A and 4B). Closer inspection of the two structures show five regions that differ significantly (FIGS. 4C and 4D). One of these regions was the linker between N- and C-terminal domains; the electron density supported only the main chain placement with high temperature factors, suggesting higher flexibility of the region. Two other regions included the loop between beta sheet D and beta sheet E (DE loop) and the region from the beginning of the beta sheet L to beta sheet M (LM loop) (FIG. 4C; see below). FIG. 4C shows the G-loop and CD loop.

Figure 5A:
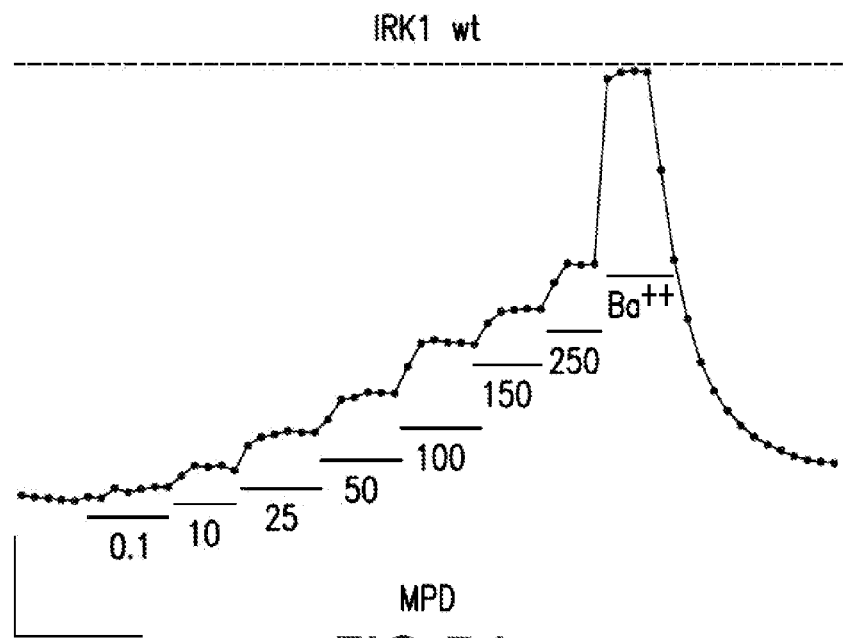
FIGS. 5A-5H show the dose response for MPD inhibition in IRK1 and GIRK2-PIP.
Figure 5B:
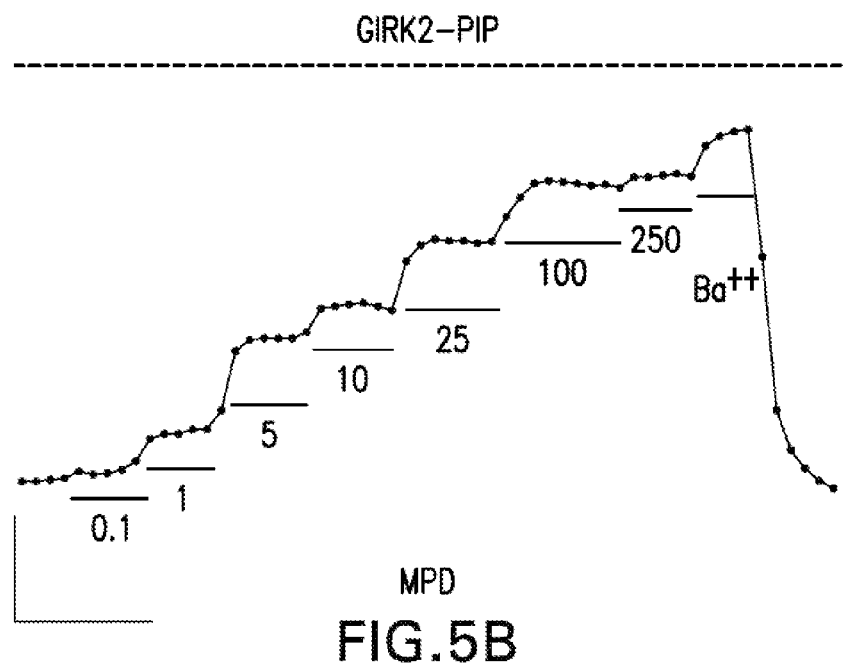

These structural changes are non-uniform in each subunit. G-loops of monomers B and D collapsed toward the center of the pore reducing the pore size of channel from 5.7 Å to 3.6 Å between the carboxyl oxygen of Ala 304 of monomer B and C-beta of Ala 304 in the monomer D (FIG. 4D). In contrast to the monomers B and D collapsing in, the monomers A and C are displaced away from the center of the channel to a more open conformation resulting in a 9.41 Å distance between their C-beta of Ala 304. G-loops of all four subunits have relatively low temperature factors than those in the wild-type structure. Closer inspection of the G-loop and CD loop regions shows that beta sheet I backbone containing T309K is unperturbed, and the conformational change is restricted to the CD loop containing R218Q and the G-loop (FIGS. 5a,b). Monomer D subunit regains the polar interaction between R218Q and T309K as predicted in FIG. 2C (FIG. 5B). Surprisingly, the other three monomers have a mix of conformations, with monomers A and B having relatively high temperature factors than the wild-type. These non-uniform conformational changes of the CD loop and the reduced temperature factors of the displaced G-loops observed in the R218Q/T309KS structure result in asymmetrical displacement of the G-loop with a smaller opening than that of the wild-type Kir2.1L channel.

Disruption of K219 by R218Q Creates Different Salt Bridge Partners for E303K.

Figure 5C:
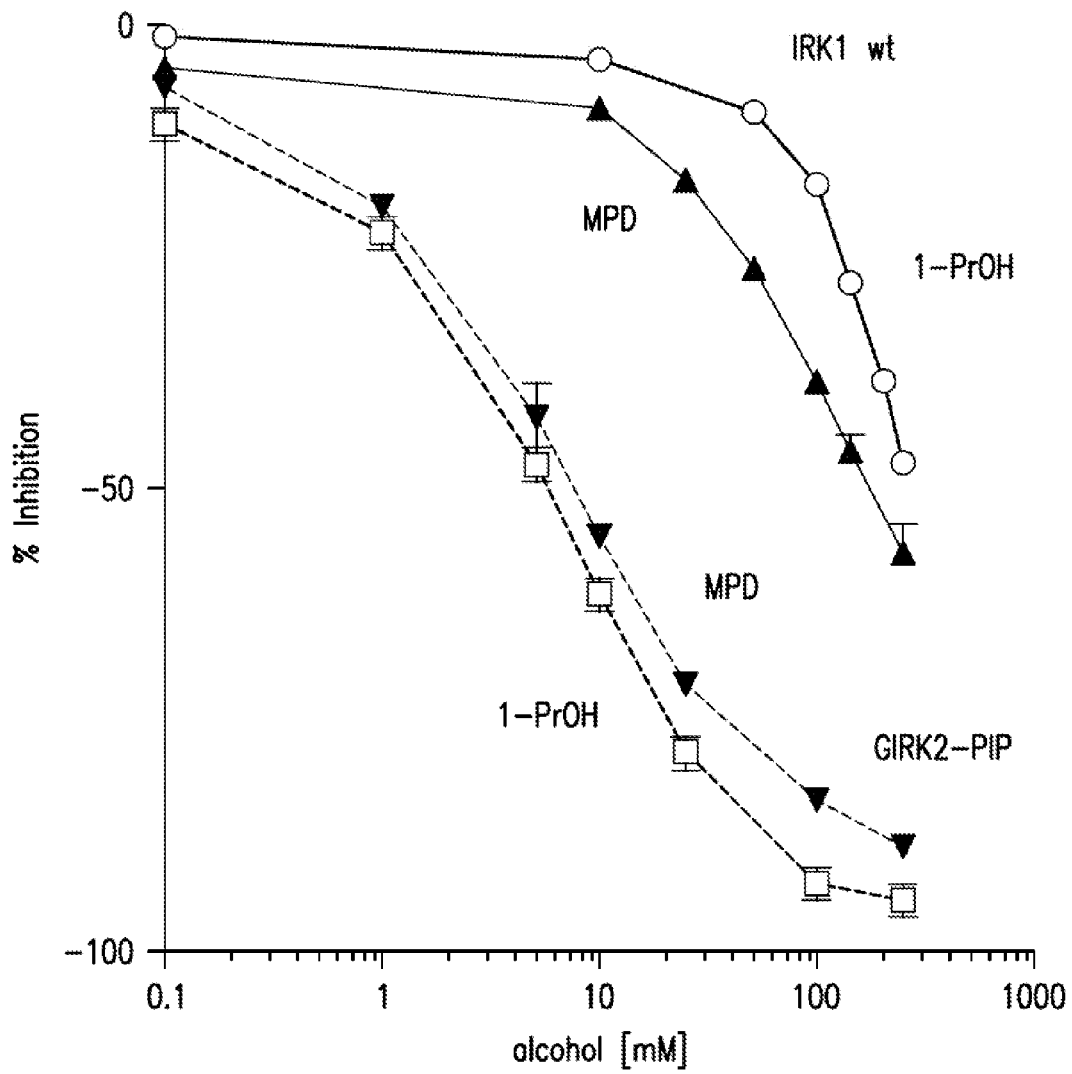

In the wild-type structure, Lys219 side chain points into a void that is expected to be a putative PIP2 binding site and Arg218 points also out of the site [2, 14]. In the R218Q/T309KS structure, Lys219 in monomers A, B, and D are highly flexible (FIGS. 5A and 5B). In contrast, the Lys219 in the monomer C has a low temperature factor (electron density peak at 1.7 σ and interacts with the carboxyl oxygen of intra-subunit Val56, rotated 180 degrees from its wild-type orientation. Like Lys219, Glu303 also shows a non-uniform difference in position. Two different conformations of the G-loop near the Glu303 were observed. In the wild-type, as with monomers A and B of R218Q/T309KS, Glu303 forms a salt bridge to Arg 312 across monomer to monomer. The other conformation shows that E303K of monomer C interacts with His221 of the C subunit forming the intra-subunit charge pair (FIG. 5C). These local disparities contribute to the formation of the asymmetric disposition of the G-loops (FIG. 4D).

Alcohol-Binding Site

During the course of our AS mutant study, it was discovered a small molecule of 2-methyl-2,4-pentanediol (MPD) bound to the cytoplasmic domain. MPD was found in all four subunits of R218Q/T309KS, in a hydrophobic pocket formed by amino acids in the DE and LM loops. A comparison between R218Q/T309KS and the wild-type Kir2.1L structures suggests that MPD induces a structural change in the Kir2.1 channel that brings the DE and LM loops closer towards each other (FIG. 4C). If MPD induces structural changes in Kir2.1 cytoplasmic domains, then MPD could affect the gating properties of the full-length channel. The hydrophobic residues interacting directly with MPD are conserved between the Kir2 and Kir3 families. Two amino acids, Pro244 and Tyr337, form H-bonds with the hydroxyl groups of MPD and are conserved in Kir2.1 and Kir3.2c but differ in Kir3.1 (FIG. 1). These loops have been previously shown to be part of putative G beta gamma activation site in Kir3 channels [24]. Whether the binding of MPD or analogs to this site will activate or suppress Kir channels is unknown. With the likely he presence of the MPD site in both Kir2 and Kir3 channels and its location near the putative G beta gamma G protein activation site, MPD has been exploited as a framework for the design a novel drug to modulate Kir2 and/or Kir3 channels (e.g., Example 3 hereafter).

Figure 6A:
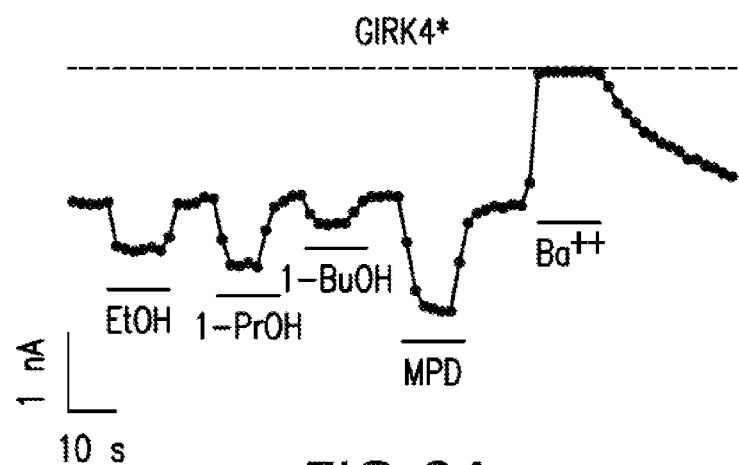
FIGS. 6A-6F show a serine to threonine mutation at the pore domain of GIRK4 and GIRK2 PIP leads to change in modulation by alcohols.
Figure 6B:
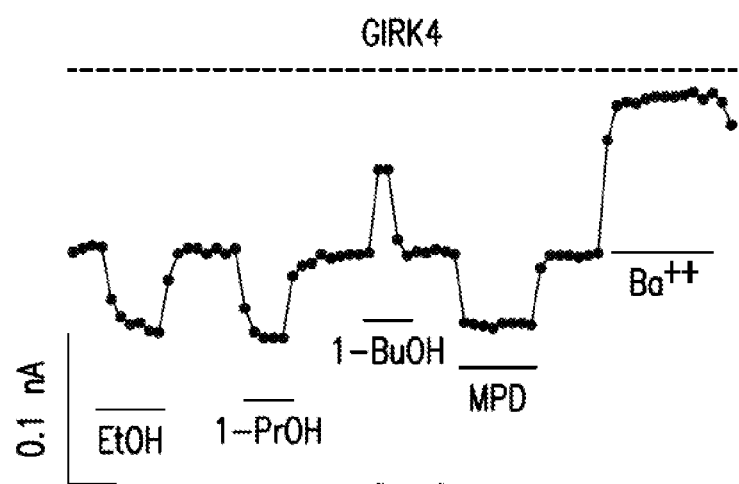

The DE and LM loops are two of the regions that are divergent between the wild-type Kir2.1L and R218Q/T309L structures (FIGS. 4C and 4D). Both regions form key interactions between adjacent monomers. Examination of the DE and LM loops identified electron density attributed to MPD. The distinct C2 tetrahedral coordination of MPD coupled with the resulting stereochemistry of the C4 atom allows easy placement within the density with agreeable (Fo-Fc) density (FIG. 6B). Extensive interactions of MPD with the solvent-accessible site show H-bonding and hydrophobic interactions pull the DE and LM loops closer together (FIG. 6B). For example, the O2 atom of MPD contacts Tyr337. The other oxygen atom 04 of MPD forms H-bond interactions with the carbonyl oxygen of Pro244 and Tyr242 via water. Phe47, Leu232, Leu245, and Leu330 provide the hydrophobic interactions with the methyl groups of MPD.

K+ Binding at the Cytoplasmic Pore Entrance.

Analysis of the electron density present in the pore of R218Q/T309KS, revealed a single K+ at the cytoplasmic end of the pore (FIG. 4B). Surprisingly, the coordination of the K+ is not formed by anionic residues in the pore, but is mediated through eight caging waters. These waters are arranged in an antiprism arrangement, with four located on the cytoplasmic side of the potassium ion and the other four located internally to the pore, similar to that of backbone and water coordinated $K^+$ of previous KcsA trans-membrane structures (FIGS. 6C and 6D) [25]. The electron density in Fo-Fc maps is consistent with $K^+$ present during purification and crystallization. Placement of $Na^+$, the only other cation in the crystallization buffer, and biologically relevant $Mg^{2+}$ in the position of $K^+$ would not account for electron density in the Fo-Fc maps, nor the 2.69-2.89 Å optimum bond distance to the water molecules typical of $K^+$ coordination [26]. All of these waters are coordinated via H-bonds to the anionic side chain and backbone carboxyl oxygen of Asp255. The presence of the water-caged $K^+$ completely occluding the pore establishes this site as the first binding site in the $K^+$ permeation pathway toward the selectivity filter.

Significance of Asymmetry in AS Mutants

For the R218Q AS mutant, it was hypothesized that changing the Thr309 to a positively charged residue (Lys) would restore a polar interaction found in wild-type Kir2.1 between Arg218 and Thr309 (FIG. 2C). Sizing chromatography and structural (2.0 Å) analyses of R218Q/T309KS revealed the presence of a significant asymmetrical conformation at a critical region (G-loop) in the permeation pathway. Both this and the previous structure [14] were solved as tetramers in the asymmetric unit, allowing the subunit to be refined independently of each other. In two of the four subunits, the G loop is displaced from its normal position. This arrangement may explain why the tetrameric assembly of the Kir2.1 channel's cytoplasmic domains is insufficient to restore ion-conducting functionality. The G-loop is anchored at one end by a flexible Gly at position 300, which likely allows the G-loop to pivot [14]. The other end of the G-loop lacks a single flexible amino acid. Here, the inter-loop side chain interactions are formed by two sets of binding pairs, Arg218/Thr309 and Glu303/Arg312, which form both inter-subunit salt bridges between G-loops and intra-subunit polar interactions with the CD loop. This arrangement suggests that mutations that alter these interactions would result in a displaced G loop and a non-functional pore. Consistent with this structure, the T3091 mutation was recently identified in patients with AS [27].

Arg218 has also been implicated in binding PIP2 and gating of Kir2.1 [2]. Altering the interaction between Arg218 and Thr309 may alter the ability of Arg218 to stabilize PIP2 binding. Based on the observations that Glu303 can form different salt-bridges, with Arg312 or His221, and that Arg218 interacts with Thr309, it was reasoned that the binding of PIP2 to Lys219 induces the movement of the CD loop, which alters the position of the G-loop through the Arg218/Thr309 interaction. The Glu303 residue would then break its inter-subunit salt-bridge to create a new intra-subunit one with His221, compensating for the energetic cost of breaking the previous salt-bridge and allowing the G-loop greater flexibility. These actions would allow the G-loop aperture to open enough for hydrated K+ ion to pass. These studies provide a plausible mechanism for PIP2 gating. Future experiments will uncover further details of PIP2-dependent gating of Kir2.1 channels.

In order for Kir channels to influence membrane excitability, they must be first targeted properly to the plasma membrane. Specific AS-affected Kir2.1L cytoplasmic domain mutants that can form tetramers appear to be trafficked properly to the membrane in their full-length form [5, 21]. The inability of delta 314-315 AS-affected Kir2.1 channels to reach the membrane [21] and our finding that delta 314-315L is mainly expressed in the inclusion bodies is consistent with the interpretation that delta 314-315 Kir2.1 channels are misfolded and cannot form a tetramer in the absence or presence of wild-type subunits, prior to leaving the endoplasmic reticulum. On the other hand, both G300V and E303K, which can form stable homo-tetramers with their cytoplasmic domains, have been shown to be successfully trafficked to the membrane [2, 5, 21]. When co-expressed wild-type channel subunits, the heteromers either do not function or have impaired function [5, 21] (but see [2]). The R218Q/T309KS structure suggests that the ability to attain the symmetry of Kir2.1 cytoplasmic domains near the G-loop gate is required for the proper function of the channel. This structure would explain how heteromeric channels carrying AS-affected subunits can be trafficked properly to the cell surface but remain non-conducting [5, 21].

Hydrated K+ Bound to Asp255 in Kir2-R218Q/T309K Structure

Previous x-ray structural studies of KirBac1.1 have uncovered K+ ions in the selectivity filter [16]. K+ ions were not resolved in the cytoplasmic domains of KirBac1.1, Kir3.1, or Kir2.1 [14, 16, 28]. Most likely, the lack of K+ ions in the crystallization buffer of Kir3.1 and Kir2.1 can explain the absence of this ion in the structure [14, 16, 28]. For KirBac1.1, two residues are absent in the loop that form the cytoplasmic end of the pore, resulting in a wider opening that may not coordinate a hydrated K+ ion through the waters of the first hydration shell [16]. Finding a single hydrated K+ ion in the inner vestibule of Kir2.1 along the permeation pathway is intriguing because of the known conduction properties of K+ channels. Potassium ions and polyamines are focused on the central water-filled canal leading to the selectivity filter. The central location and exact coordination of the K+ suggest the ion permeation pathway of the cytoplasmic domain is more like a set of stops mediated by both waters and anionic side chains, not a hydrophilic wall that only recruits K+ ions at random sites along its wall [9, 12, 13]. Asp255 represents one of the first positions along this permeation pathway for both polyamines and potassium ions. Although the 'long-pore' effect of K channels is attributed to the multiple potassium ions located in the selectivity filter, the presence of the hydrated potassium ion along the central canal demonstrates that the long pore indeed extends quite far into the cytoplasm.

Citations

1. Plaster, N. M., et al., Mutations in Kir2.1 cause the developmental and episodic electrical phenotypes of Andersen's syndrome. Cell, 2001. 105(4): p. 511-9.
2. Lopes, C. M., et al., Alterations in conserved Kir channel-PIP2 interactions underlie channelopathies. Neuron, 2002. 34(6): p. 933-44.
3. Donaldson, M. R., et al., PIP2 binding residues of Kir2.1 are common targets of mutations causing Andersen syndrome. Neurology, 2003. 60(11): p. 1811-6.
4. Tristani-Firouzi, M., et al., Functional and clinical characterization of KCNJ2 mutations associated with LQT7 (Andersen syndrome). J Clin Invest, 2002. 110(3): p. 381-8.
5. Preisig-Muller, R., et al., Heteromerization of Kir2.x potassium channels contributes to the phenotype of Andersen's syndrome. Proc Natl Acad Sci USA, 2002. 99(11): p. 7774-9.
6. Hosaka, Y., et al., Function, subcellular localization and assembly of a novel mutation of KCNJ2 in Andersen's syndrome. J Mol Cell Cardiol, 2003. 35(4): p. 409-15.
7. Chen, L., et al., A glutamate residue at the C terminus regulates activity of inward rectifier K+ channels: implication for Andersen's syndrome. Proc Natl Acad Sci USA, 2002. 99(12): p. 8430-5.
8. Hille, B., Ion Channels of Excitable Membranes. Third ed. 2001, Sunderland, Mass.: Sinauer Associates, Inc.
9. Nichols, C. G. and A. N. Lopatin, Inward rectifier potassium channels. Annu Rev Physiol, 1997.59: p. 171-91.
10. Lu, Z. and R. MacKinnon, Electrostatic tuning of Mg2+ affinity in an inward-rectifier K+ channel. Nature, 1994. 371(6494): p. 243-6.
11. Lopatin, A. N., E. N. Makhina, and C. G. Nichols, Potassium channel block by cytoplasmic polyamines as the mechanism of intrinsic rectification. Nature, 1994. 372 (6504): p. 366-9.
12. Kubo, Y. and Y. Murata, Control of rectification and permeation by two distinct sites after the second transmembrane region in Kir2.1 K+ channel. J Physiol, 2001. 531 (Pt 3): p. 645-60.
13. Fujiwara, Y. and Y. Kubo, Functional Roles of Charged Amino Acid Residues on the Wall of the Cytoplasmic Pore of Kir2.1. J Gen Physiol, 2006.
14. Pegan, S., et al., Cytoplasmic domain structures of Kir2.1 and Kir3.1 show sites for modulating gating and rectification. Nat Neurosci, 2005. 8(3): p. 279-87.
15. Huang, C. L., S. Feng, and D. W. Hilgemann, Direct activation of inward rectifier potassium channels by PIP2 and its stabilization by Gbetagamma. Nature, 1998. 391 (6669): p. 803-6.
16. Kuo, A., et al., Crystal structure of the potassium channel KirBac1.1 in the closed state. Science, 2003. 300(5627): p. 1922-6.
17. Long, S. B., E. B. Campbell, and R. Mackinnon, Crystal structure of a mammalian voltage-dependent Shaker family K+ channel. Science, 2005. 309(5736): p. 897-903.
18. Lu, Z., A. M. Klem, and Y. Ramu, Ion conduction pore is conserved among potassium channels. Nature, 2001. 413 (6858): p. 809-13.
19. Silverman, S. K., H. A. Lester, and D. A. Dougherty, Subunit stoichiometry of a heteromultimeric G protein-coupled inward-rectifier K+ channel. J Biol Chem, 1996. 271(48): p. 30524-8.
20. Fink, M., et al., Dominant negative chimeras provide evidence for homo and heteromultimeric assembly of inward rectifier K+ channel proteins via their N-terminal end. FEBS Lett, 1996. 378(1): p. 64-8.
21. Bendahhou, S., et al., Defective potassium channel Kir2.1 trafficking underlies Andersen-Tawil syndrome. J Biol Chem, 2003. 278(51): p. 51779-85.
22. Zaritsky, J. J., et al., The consequences of disrupting cardiac inwardly rectifying K(+) current (I(K1)) as revealed by the targeted deletion of the murine Kir2.1 and Kir2.2 genes. J Physiol, 2001. 533(Pt 3): p. 697-710.
23. Kubo, Y., et al., Primary structure and functional expression of a mouse inward rectifier potassium channel. Nature, 1993. 362(6416): p. 127-33.
24. Finley, M., et al., betaL-betaM loop in the C-terminal domain of G protein-activated inwardly rectifying K(+) channels is important for G(betagamma) subunit activation. J Physiol, 2004. 555(Pt 3): p. 643-57.
25. Zhou, Y., et al., Chemistry of ion coordination and hydration revealed by a K+ channel-Fab complex at 2.0 Å resolution. Nature, 2001. 414(6859): p. 43-8.
26. Periole, X., et al., Simple Two-body Cation-Water Interaction Potentials Derived from ab Initio Calculations. Comparison to Results Obtained with an Empirical Approach. J. Phys. Chem., 1997 (101): p. 5018-5025.
27. Bendahhou, S., et al., In vivo and in vitro functional characterization of Andersen's syndrome mutations. J Physiol, 2005. 565(Pt 3): p. 731-41.

28. Nishida, M. and R. MacKinnon, Structural basis of inward rectification: cytoplasmic pore of the G protein-gated inward rectifier GIRK1 at 1.8 Å resolution. Cell, 2002. 111(7): p. 957-65.
29. Lewohol, J., et al., G-protein-coupled inwardly rectifying potassium channels are targets of alcohol action. Nature Neuroscience 1999. 2(12): p 1084-1090.
30. Kobayashi, T., et al., Ethanol opens G-protein-activated inwardly rectifying K+ channels. Nature Neuroscience 1999. 2(12): p 1091-1097.
31. Zhou, W., et al., Mechanism underlying bupivacaine inhibition of g protein-gated inwardly rectifying K+ channels. Proc. Natl. Acad. Sci. 2006. 98: p. 6482-6487.

Example 3

Kir Channel Modulators

It has been determined that inwardly rectifying potassium (Kir) channels are regulated directly by small molecule alcohol compounds. Three-dimensional crystallographic analysis of Kir channels has elucidated atomic details of binding pocket interactions with 2-methyl-2,4-pentanediol (MPD). MPD inhibits Kir2 channel activity and activates Kir3 channel activity. Amino acid substitutions in this hydrophobic pocket of the channel protein may alter the response to MPD. As determined by patch-clamp determinations of ion transport activity, a racemic mixture of 2-methyl-2,4-pentanediol, (±)MPD, activates Kir3 channels with an EC50 of >200 mM and inhibits Kir2 homotetramer channels with an $IC_{50}$ of ~200 mM. The time course of inactivation or activation is within seconds of (±)MPD application. Bupivacaine inhibits Kir3.1/3.4 and Kir3.1/3.2 channels with an $IC_{50}$ of ~20-40 micromolar [31].

The following also were observed. Maximal activation of Kir3 channels by 100 mM (±)MPD is 280% that of 100 mM EtOH. Maximal activation of Kir3 channels by 100 mM R(-)2 methyl-2,4-pentanediol is 60% that of 100 mM (±)MPD. Maximal activation of Kir3 channels by 100 mM 3-methyl-1,3,5-pentanetriol is 70% that of 100 mM (±)MPD. Maximal activation of Kir3 channels by 100 mM 2,5-dimethyl-1,2,6-hexanetriol is 70% that of 100 mM (±)MPD. Maximal activation of Kir3 channels by 100 mM (±) 2,4-pentanediol is 50% that of 100 mM (±)MPD.

The effect of MPD on Kir2 channel activity was analyzed further. FIG. 7 shows a dose response curve for MPD inhibition of Kir2.1 channels expressed in HEK293 cells. The fractional current remaining is plotted as a function of MPD concentration. The response for each cell was fit with the Hill equation. The average IC50 and Hill coefficients are shown (n=6). This data shows that MPD inhibits Kir2 channel activity.

Example 4

Determination that Alcohol Binds at Two Sites

Alcohol is abuse is a major health problem worldwide. Consumption of alcohol leads to an overall increase in inhibition of the central nervous system. Alcohols are postulated to alter neural activity in the brain by modulating ion channels. Many ligand-gated ion channels, such as those gated by GABA, N-methyl-D-aspartate, glycine, acetylcholine, and serotonin, are sensitive to alcohols (Cardoso et al., 1999; Lovinger et al., 1989; Mihic et al., 1997; Zhou and Lovinger, 1996). The molecular mechanism by which alcohol alters channel function, however, is not well understood (Deitrich et al., 1989). Alcohol was initially hypothesized to indirectly alter the function of channels by changing the fluidity of the lipid bilayer. More recently, studies have suggested that alcohol acts directly on the channel protein. For example, mutations in the TM2 and TM3 domains of glycine and GABA channels alter the sensitivity to alcohol modulation (Mihic et al., 1997; Wick et al., 1998). In addition to these ligand-gated channels, G protein-gated inwardly rectifying potassium (GIRK or Kir3) channels are also modulated by alcohols (Kobayashi et al., 1999; Lewohl et al., 1999). GIRK channels serve a role in determining neuronal excitability; loss of GIRK channels promotes susceptibility to seizures (Signorini et al., 1997). GIRK channels are involved in the response to alcohol. Mice lacking GIRK2 channels exhibit diminished alcohol-dependent analgesia (Blednov et al., 2003) and self-administer more alcohol than wild-type mice (Blednov et al., 2001).

Ethanol potentiates $GABA_B$ receptor activation of GIRK channels in neurons and in heterologous expression systems (Kobayashi et al., 1999; Lewohl et al., 1999). GIRK channels are activated by range of alcohol carbon chain lengths at low mM concentrations. For comparison, a blood alcohol level of 0.1% is ~22 mM and could approach 75 mM in intoxicated individuals. Pertussis-toxin treatment, which prevents $GABA_B$ receptor activation of GIRK channels, does not alter activation by alcohol (Kobayashi et al., 1999), indicating that alcohol activation does not depend on receptor coupling. Using C-terminal truncation mutants, Lewohl et al (1999) demonstrated the distal C-terminal domain of GIRK2 is involved in alcohol activation. Furthermore, alcohols with a carbon chain length greater than four carbons (1-butanol) failed to activate GIRK channels, suggesting a 'cutoff' effect for alcohol activation (Kobayashi et al., 1999). Similar cutoff effects were found for alcohol modulation of GABA and glycine-activated channels (Wick et al., 1998). Taken together, these studies suggest that activation of GIRK channels by alcohols involves a physical site within the channel but the location of this putative site has eluded detection.

Recently, the structure of a variant of IRK1 was solved that contained 2,4 methyl-pentane diol (MPD) bound to the crystals (Pegan et al., 2006). While MPD is commonly used as a cryoprotectant, it is also a type of alcohol. The MPD pocket is located at the interface of two adjacent IRK1 subunits and has features similar to the odorant alcohol binding protein, LUSH, which was crystallized with ethanol (Kruse et al., 2003). In both structures, the alcohol pocket is formed by hydrophobic amino acids and H-bonds between amino acid side-chains and the alcohol. In contrast to GIRK channels, however, IRK1 channels are inhibited by alcohols of different carbon chain lengths (Kobayashi et al., 1999; Lewohl et al., 1999). Thus, alcohols can produce two different effects with inwardly rectifying potassium channels. In the current study, it was hypothesized that the MPD pocket is the site of alcohol modulation for inward rectifiers. It was discovered that MPD pocket is involved in alcohol activation of GIRK channels, converging with G protein activation, while a second site on the extracellular side of the channels in involved in alcohol inhibition.

1. RESULTS

MPD, an alcohol bound to IRK1 crystal structure modulates IRK1 and GIRK2. A crystal structure of the cytoplasmic domain of IRK1 was published that was obtained by directly fusing the N- and the C-terminal of IRK1, leaving out the transmembrane domains (Pegan 2006 and reported herein). In this structure, four of the subunits come together to make a tetrameric cytoplamsic domain. It was reported that an alcohol, 2-Methyl, 2-4-pentane diol, which is cryopreservant, was bound to the 4 subunit interfaces, at distinct water accessible, hydrophobic pockets (FIG. 1a). A closer examination of the sites of interaction showed that the alcohol was interacting with hydrophobic amino-acid side chains from three different domains, the N-terminus, and βL-βM domain of one subunit and βD-βE domain of a second subunit (FIG. 1b). There were additional H-bond interaction between one of the OH group of MPD and a backbone carbonyl group from the βD-βE domain. Additionally there was a second, weaker H-bond interaction between an OH group of Tyrosine from the βL-βM group and the second OH of MPD. This pattern of interaction was almost identical in all four of the MPD interacting hydrophobic pocket in the structure.

Structural comparison between the IRK1 (Pegan et al., 2006; Pegan et al., 2005) and GIRK2 (Inanobe, 2007), a G-protein sensitive member of the IRK family, reveal that a similar hydrophobic pocket exists in the GIRK2 channels, and that the amino-acids that align the pocket are conserved between the two channels (FIGS. 1b,c,d). With the findings that MPD was bound to a distinct hydrophobic pocket in the IRK1 structure, and that this pocket is conserved between IRK1 and GIRK2, the effect of this pocket on alcohol interactions with IRK and GIRK channels was determined in studies described hereafter.

Using whole-cell patch clamp, technique in HEK293T cells transfected with IRK1 or GIRK2 channels, it was determined that MPD does in fact modulate these channels. Addition of 100 mM MPD inhibits the inward currents of the IRK1 channel, without changing the reversal potential or altering inward rectification (FIG. 1e). This inwardly rectifying current is blocked completely by the application of 1 mM $Ba^{++}$, which blocks the channel near the selectivity filter.

Figure 1F:
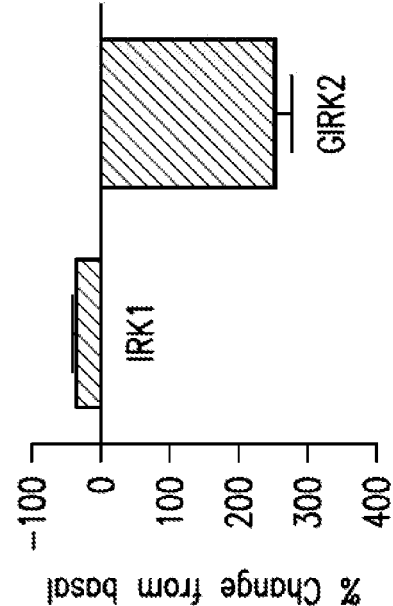
Figure 1G:
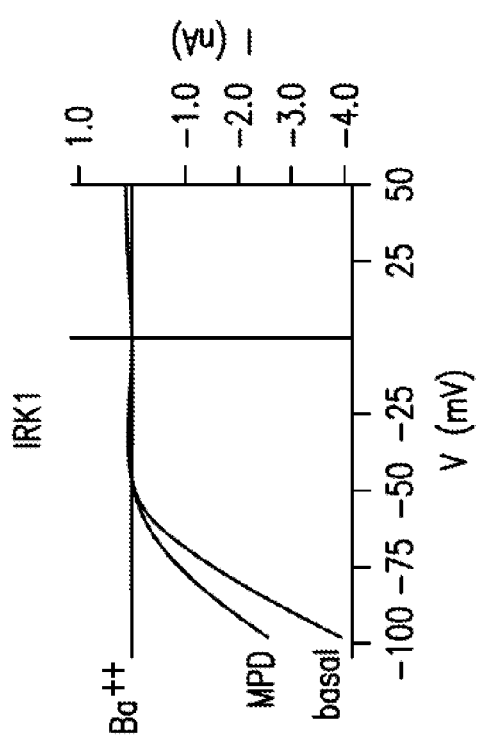
Figure 1H:
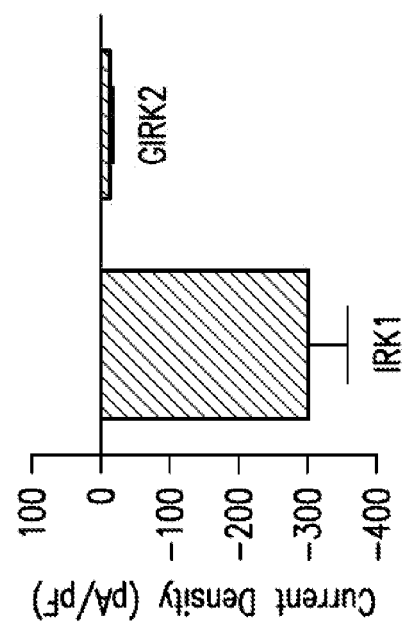

On the other hand, MPD enhances the inward currents of GIRK2, without changing the reversal potential or inward rectification (FIG. 1f). The $Ba^{++}$ subtracted basal current density at −100 mV is large for IRK1 (−299.5±59 pA/pF; n=5) whereas GIRK2 basal current density is significantly smaller (−12.8±3 pA/pF; n=5) (FIG. 1e). These current recordings are stereotypic for IRK channels, which are constitutively open, and thus have large basal currents, and GIRK2 channels, which have small basal currents, are induced by agonists such as alcohols and Gβγ. MPD modulation was determined as a percent change of basal current for IRK (−32.46±3.9%; n=5) and GIRK2 (246±26.7% n=5), where negative values represent inhibition, and positive values represent activation (FIGS. 1g,h). Here it was shown that MPD, which was bound to distinct sites in the IRK1 crystal structure, modulates both IRK1 and GIRK2 channels.

MPD activates GIRK2 channels with similar characteristic as ethanol and 1-propanol. Alcohols, such as ethanol, slightly inhibit IRK, but activate GIRK2 channels (Kobayashi et al., 1999; Lewohl et al., 1999), and it was hypothesized that MPD modulates these channels in a similar manner. To address this hypothesis, there was a focus on MPD's activation of GIRK2. First a dose response assay was conducted for activation of GIRK2 by MPD (FIG. 2a). A concentration as low as 10 mM can induce a noticeable activation of GIRK currents, which increases in a dose dependent manner. Currents could be measured reliably for doses up to 300 mM, which was completely blocked by application of 1 mM $Ba^{++}$. To quantify this response profile, currents were measured at steady state for each dose, and divided it by $Ba^{++}$ blocked basal current. The results were plotted in the dose response curves (FIG. 2b). The dose response profile for ethanol, and 1-propanol also were compared as shown in FIG. 2b. The MPD activation curve fits between the activation curve of ethanol, and 1-propanol. The three alcohols tested also exhibited similar dose response patterns, which increases steeply after the 100 mM dose, and do not saturate at the highest dose tested. Therefore, it was concluded that MPD activates GIRK2 with similar, low (millimolar) affinity activation, as Ethanol and 1-Propanol.

Figure 2D:
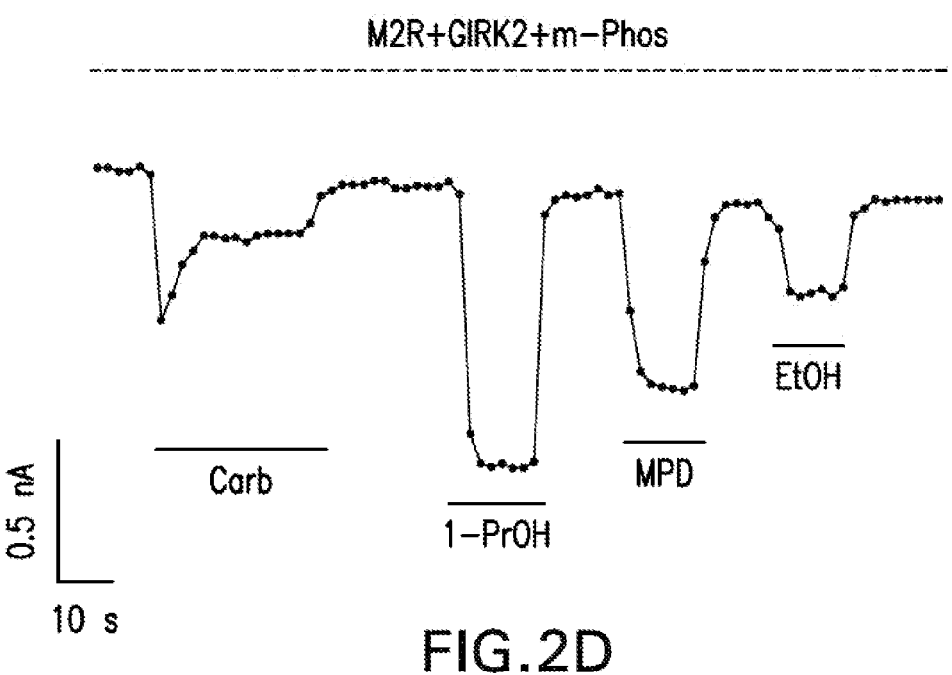
Figure 2E:
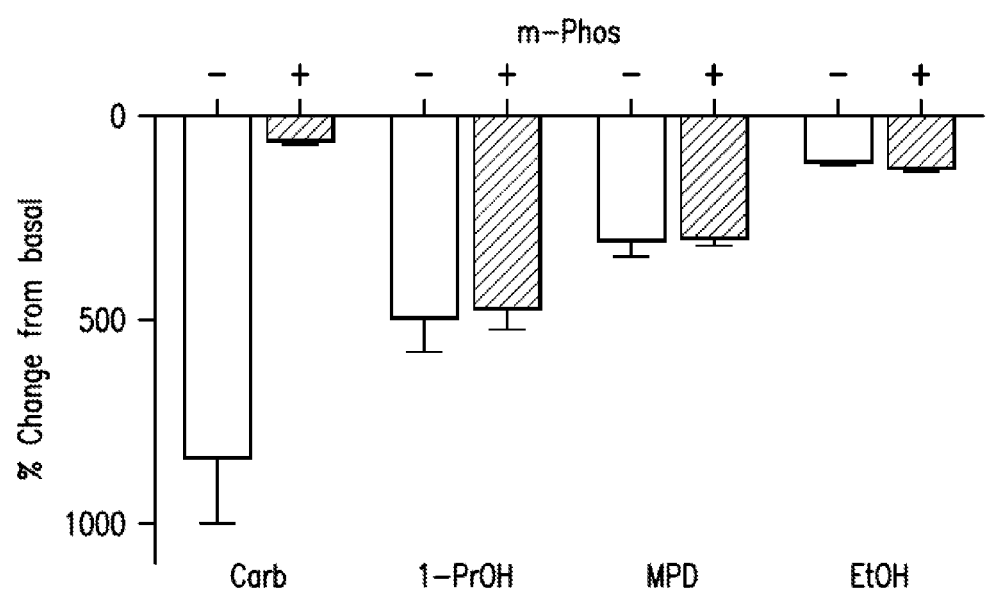

Activation of GIRK2 by ethanol does not require the G-protein coupled receptor, nor does it require Gβγ. Kobayashi et al. had shown that using anti-sense oligonucleotide in *Xenopus* oocytes injected with GIRK cRNA still elicit GIRK channel activation (Kobayashi et al., 1999). It was hypothesized that MPD dependent enhancement of GIRK2 currents does not require Gβγ activation. HEK293T cells were co-transfected with muscarinic receptor 2 M2R, a Gαi coupled receptor, with or without myristylated-phosducin (Rishal et al., 2005). This variant of phosducin has been shown to chelate Gβγ after dissociation of the G-protein trimer upon activation of the M2R. When M2R is activated by 5 uM Carbachol, there was a robust GIRK2 current that did not desensitize (FIG. 2c). However, when cells co-transfected with the myristylated-phosducin were examined, a rapid activation and desensitization of the Carbachol activated current was identified (FIG. 2d). On the other hand, in both conditions, there was no desensitization in the ethanol, MPD or 1-propanol induced currents. Additionally, the steady state current upon activation by alcohols did not differ in the cells with or without m-phosducin, whereas there was a drastic difference in the Carbachol-activated current in the two groups (FIG. 2e). These data demonstrate that MPD and other alcohols activate GIRK2 channels with a mechanism that does not require Gβγ activation, and thus is expected to interact via a direct interaction with the channel.

Alanine and Tryptophan Scan Mutagenesis of the MPD Pocket in GIRK2

It was determined that MPD activates GIRK2 channels with similar characteristics as other alcohols. The investigation of MPD was initiated from crystal structure data of MPD bound to the cytoplasmic domain an inwardly rectifying channel. Thus studies were undertaken to determine whether this MPD bound pocket is the site of activation for GIRK2 channels. Therefore, an Alanine/Tryptophan mutagenesis scan of the amino-acids that line this hydrophobic pocket in GIRK2 was conducted. There was a focus on Tyr58 from the N-terminus domain, Ile244, and Leu257 from the βDβE domain, and Leu342 and Tyr349 from the βL-βM domain. Single mutants of GIRK2 channels were generated at these positions, and it was determined whether there were alterations in GIRK2 channel activation. Mutant channels were expressed in HEK293T cells, and the presence of a basal inward current that could be blocked by $Ba^{++}$ was assessed. Six out of the 10 mutants tested lacked $Ba^{++}$ blocked basal current (<1 pA/pF, n≧7) (FIG. 3a).

This lack of current could be due to either a lack of proper assembly and trafficking to the plasma membrane, or due to defect of function once at the surface. Therefore, it was determined whether these mutant channels trafficked to the surface using an extracellular HA-tagged version of the mutant channels. For example, when the Y58W mutant channel was expressed, surface labeling of the HA tag could be seen at the plasma membrane, whereas total GIRK2 was seen both intracellularly and at the plasma membrane (FIG. 3A). Thus Y58W, and Y58A (not shown) mutant channels lack basal currents, although they are present at plasma membrane. This is contrasted with I244W mutant channel (FIG. 3A), surface expression of the HA tag was absent, but, GIRK2 channels proteins were expressed inside the cell. Thus the I244W, and I244A (not shown) mutants lack basal currents because they do not traffic to the plasma membrane. Y349W mutant channels, which has a basal current similar to wild type was used as a positive control. From these experiments it was concluded that the Ala or Trp substitution at Ile244 leads to defect in assembly, and/or trafficking to the membrane, whereas Y58A, Y58W, L342W, and Y349A mutant channels make it to the surface, but fail to conduct currents (FIG. 3a). Thus amino-acids that contribute to this hydrophobic pocket are important for GIRK channel function.

Mutation at Leu257 Shows Alteration in Alcohol Modulation of GIRK2

Figure 4F:
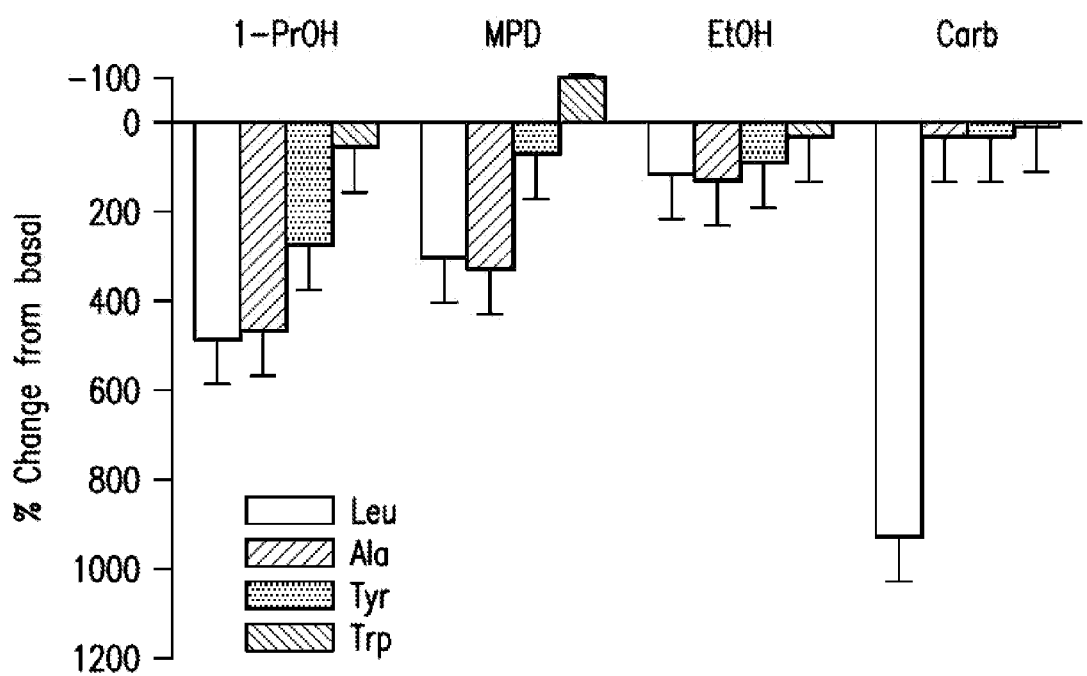

To determine whether there is alteration of alcohol modulation for mutations at this hydrophobic pocket, mutant channels that express basal currents were studied. Both the Ala and Trp substitutions at Leu257 leads to functional channels (FIG. 3a). Furthermore, when crystal structures of IRK1 with, and without MPD, were aligned, the greatest RMS deviation (3.1A) in the MPD pocket was at this corresponding Leucine residue. Additional substitutions were generated at the Leu257 position, namely, Asn, Ile, Phe, Tyr. Only the Ala, Tyr and Trp mutations, however, led to substantial basal currents (>1 pA/pF) (FIG. 4a). It was next determined whether there was altered alcohol and G-protein activation of these mutant channels compared to wild type channels. The rank order of activation for wildtype GIRK2 (n=32) for 100 mM alcohols was: 1-PrOH(486±34%)>MPD (305±19%)>EtOH (119±5%), whereas the G-protein activation by Carbachol was the largest in magnitude (928±141%) (FIG. 4f).

The L257A mutant channel (n=9) had a significantly smaller basal current density (2.0±0.27 pA/pF vs. 17.1±2.6 pA/pF for WT) (FIG. 4a). The rank order of activation for this mutant channel was: 1-PrOH(467±44%)>MPD(330±27)>EtOH(132±9%) and (36±6%) for Carbachol activated currents (FIGS. 4b,f). Therefore alcohol activation did not change for the L257A mutant channel, although G-protein dependent activation decreased significantly.

The L257Y mutant channel had normal basal current density (-17.0±4.8 pA/pF, n=9) but had significant reduction in 1-Prop, MPD, and Carbachol dependent activation. The rank order of activation for L257Y mutant channel was 1-PrOH (275±34%)>EtOH(92±10%)>MPD(73±10%) whereas Carbachol activation was (38±11%) (FIGS. 4c,f). Therefore, substitution of a large amino-acid Try at Leu257 led to loss in both alcohol and G-protein mediated activation.

The L257W mutant channel had normal basal current density (-10.4±3 pA/pF, n=9) but PrOH(57±6%)>EtOH (34±3%), and MPD actually inhibited the channel completely (-97±4%) (FIGS. 4d,f). Furthermore, as with the other mutations at Leu 257, L257W mutant channel also lost G-protein mediated activation (12±2%). Therefore mutating the Leu257 to the largest amino acids, Trp led to a remarkable loss of activation by alcohols and G-proteins, and introduced a switch in modulation, namely a complete inhibition of basal current by MPD.

Mutagenesis at the Tyr349, and Leu342 positions lead to Y349W, and L342A mutant channels that had basal current density of greater than 1 pA/pF. Out of these two mutant channel, the Y349W mutant channel (n=10) led to a significant loss of 1-PrOH (256±25%) and Carbachol (56±5) activated current. Tyr349 is in the βLβM domain, which has been shown previously to be important for Gβγ activation. Here it was shown that the βLβM domain is also involved in alcohol activation.

L245W Mutation of IRK1 does not Alter Inhibition by Alcohols

Figure 5D:
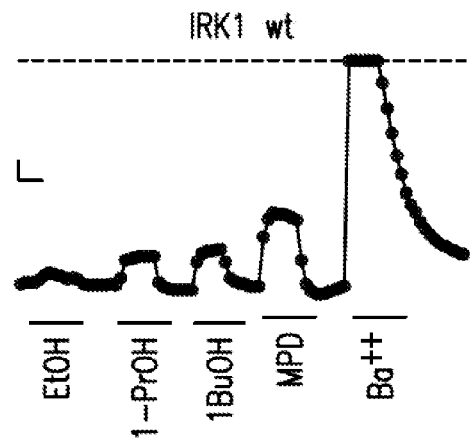
Figure 5E:
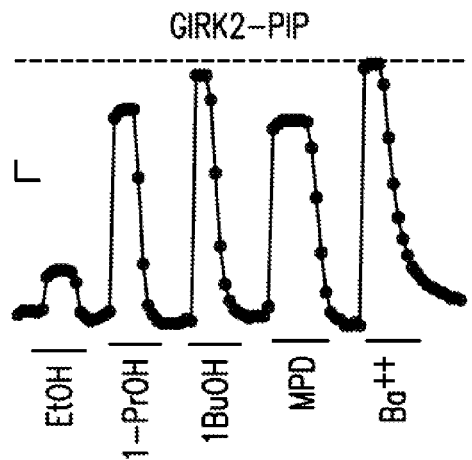
Figure 5F:
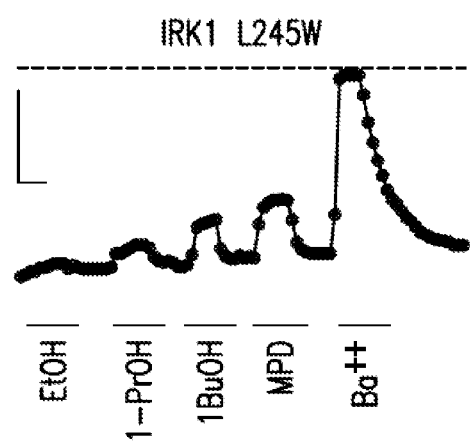

The GIRK2 L257W mutant channel was inhibited by MPD. MPD also inhibits IRK1 channel. The crystal structure is of MPD bound to cytoplasmic domain of IRK1 channel. Thus whether this hydrophobic pocket is the site of inhibition by MPD and other alcohols was assessed. An equimolar (n=5) (50 mM) alcohol series was conducted with EtOH, 1-PrOH, 1-BuOH, and MPD for inhibition of IRK1 channel. The rank order of inhibition increased by increased chain length, and was the following: EtOH(-5±1%)<1-PrOH(-12±2%)<1-BuOH(-20±3%)<MPD (-25±3%) (FIGS. 5d,h). When Leu245 was mutated to Trp and assessed the inhibition by these alcohols, no change in rank order of inhibition, or in the magnitude of inhibition, was observed. The rank order was: EtOH (-3±1%)<1-PrOH(-8±1%)<1-BuOH(-20±2%)<MPD(-27±2%), (FIGS. 5f,h). Therefore, the IRK1 L245W mutant channel does not have altered inhibition by alcohol.

What could be the reason IRK1 is inhibited by alcohols? The IRK1 channel has a high open probability, thus leading to large basal currents. One of the reasons for this large basal current is that IRK1 binds PIP2 with high affinity (Zhang et al., 1999). It was shown previously that ethanol can inhibit a chimeric channel in which the domain responsible for high affinity binding to PIP2 in IRK1 was swapped into the GIRK channel (Zhou et al., 2001). This chimera was reported by Zhang et al., who stated that swapping this high PIP2 affinity domain leads to constitutively open GIRK channel with large basal currents, which cannot be additionally potentiated by G-protein βγ (Zhang et al., 1999).

Figure 5G:
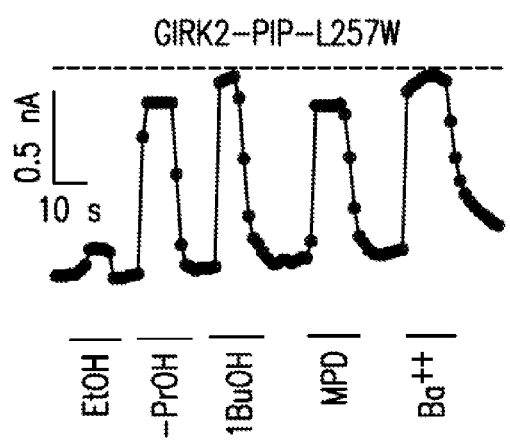
Figure 5H:
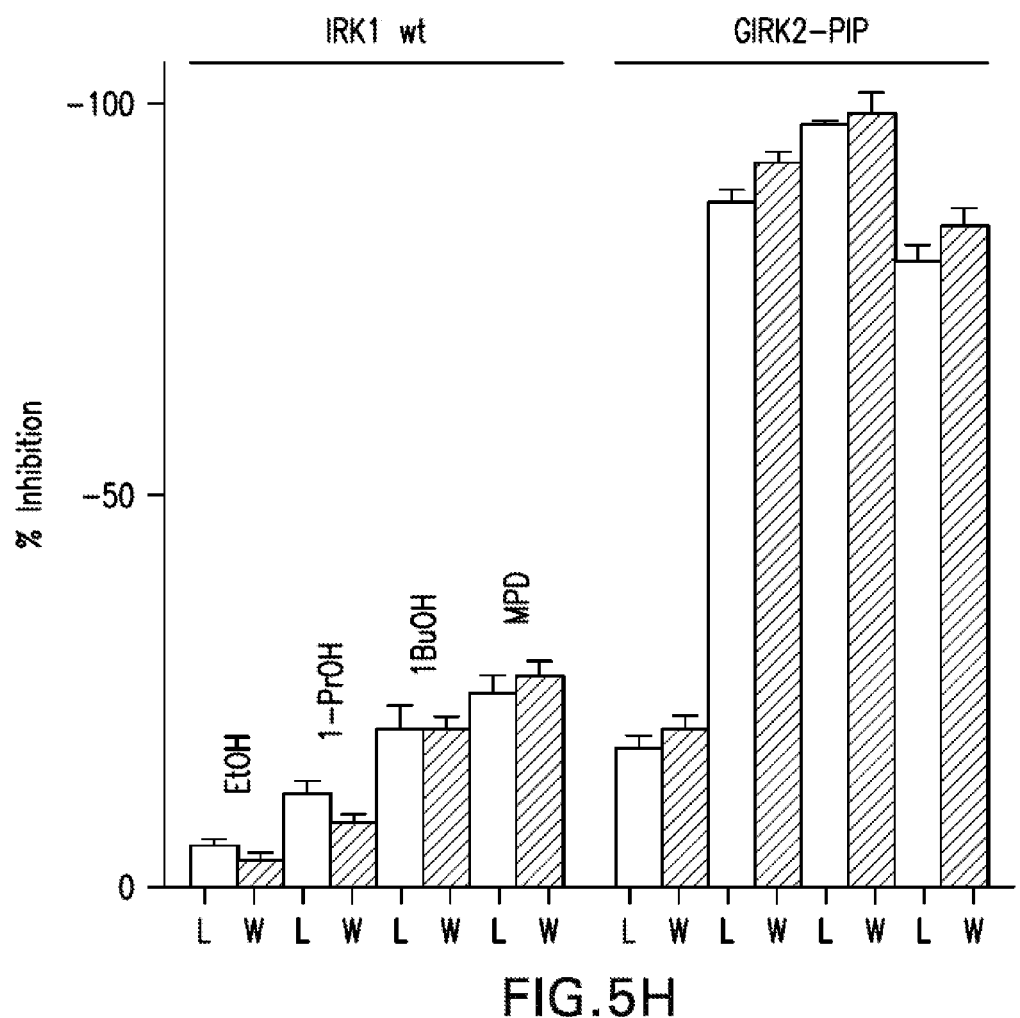

The GIRK2 PIP chimeric channel has large basal current, and has high sensitivity of inhibition by alcohols, which was not altered with the L257W mutation. A refined version of this chimera was generated by swapping 7 amino-acids at the βC-βD loop from those in IRK1 to those at corresponding positions in GIRK2. This mutant, named GIRK2 PIP, has large basal currents (-530±197 pA/pF, n=5), similar to a previously published version of this chimera. Equimolar alcohol series reveals that this channel has a high sensitivity to inhibition by longer chain (>2 carbon) alcohols. The rank order of inhibition for GIRK2 PIP channel was: EtOH(-18±2%)<1-Prop(-87±2%)<1-BuOH(-97±1%) and MPD(-80±2%) (5e,h). To test whether this sensitivity to inhibition would be altered by mutation at the MPD-bound hydrophobic pocket, Leu257 was mutated to Trp for this channel. Similarly to IRK1, there was no change in inhibition by the alcohols tested. The rank order of inhibition for this mutant channel, was: EtOH(-20±2%)<-Prop(-92±1%)<1-BuOH(-99±3%) and MPD(-84±3%) (FIGS. 5g,h) As seen in FIG. 5e, the sensitivity of inhibition by alcohol did not change for this mutant.

Here it was shown that the constitutively open IRK1 channel, and the constitutively open GIRK2 PIP channel are inhibited by alcohols, where longer chain alcohols have a greater impact. However, a prominent mutation at the MPD pocket, which attenuated activation of GIRK2 did not alter the sensitivity to inhibition by alcohols for both of these channels. These data led to the conclusion that there is a second site of action for inhibition by alcohols.

Figure 6C:
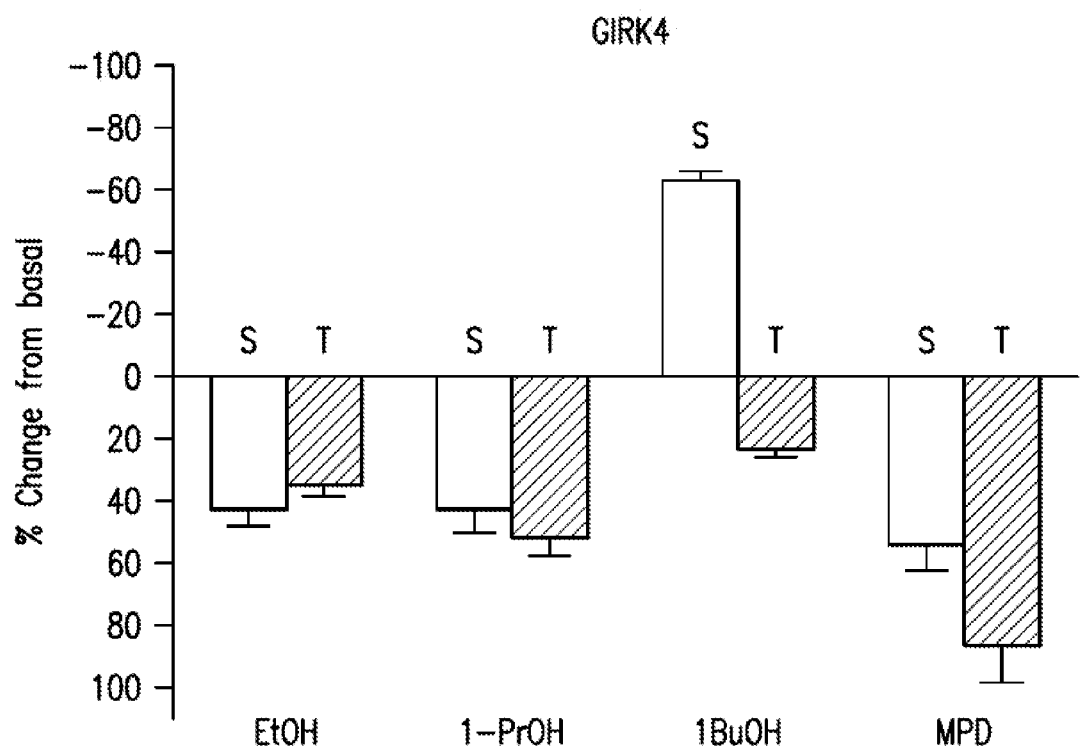

A mutation at the pore region of GIRK4 leads to loss of inhibition by 1-Butanol Insight into the second site emerged from experiments in the GIRK4 channel. It has been previously shown that GIRK1/4 tetramers are inhibited by 1-butanol, whereas GIRK1/2 channels are activated by 1-BuOH. It therefore was determined whether GIRK4 homo-tetramers are also inhibited by 1-Butanol. As seen in FIG. 6B, GIRK4 currents (n=7) are activated by EtOH (43±6%), 1-PrOH (43±7%), and MPD (55±8%) but inhibited by 1-BuOH (-70±3%) (FIG. 6C). A Ser to Thr mutation at amino-acid 143 (S143T, also known as GIRK4*) near the selectivity filter has been shown to have large currents, and large G-protein activated component, as compared to wild type GIRK4 (Vivaudou et al., 1997). Whether the modulation profile by alcohols changed for this mutant channel was assessed. The GIRK4 S143T mutant channel (n=7) was activated by EtOH (35±4), 1-PrOH (51±6), MPD (87±12), and 1-BuOH (23±3%) actually activated this channel (FIGS. 6A,C). This information argues that along with the enhanced functionality of the GIRK4* channel, this Ser to Thr mutation also switches the modulation of 1-BuOH from inhibition to activation.

Figure 6D:
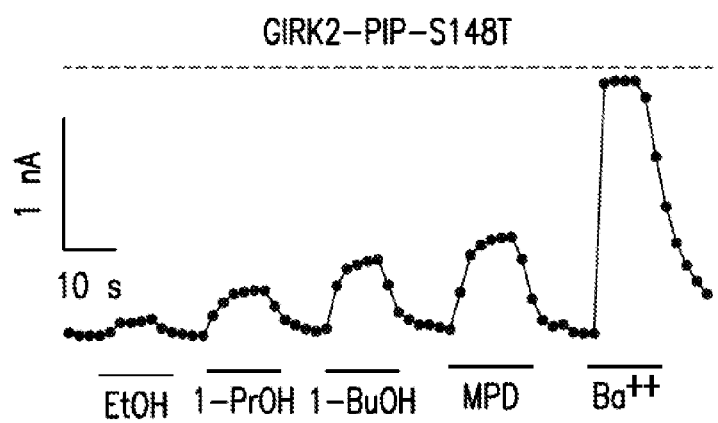
Figure 6E:
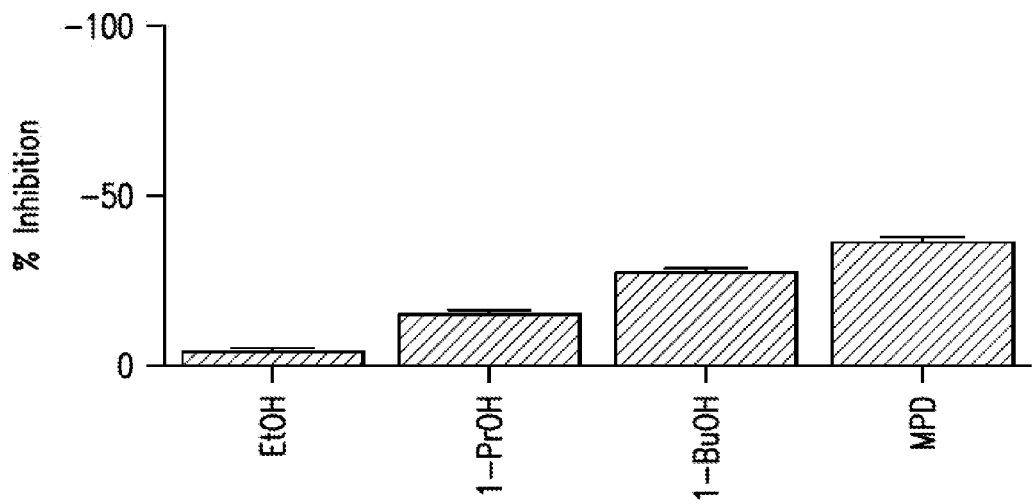
Figure 6F:
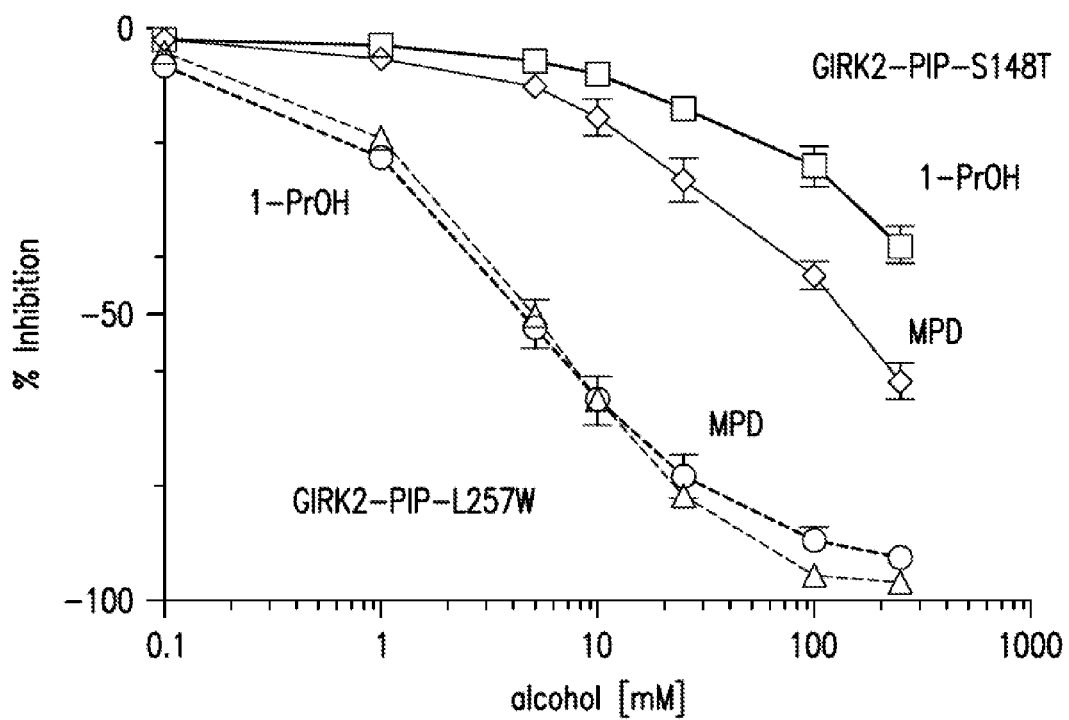

It was hypothesized that this Serine, positioned at the pore loop of the channel is important for sensitivity to inhibition by alcohol in inwardly rectifying channels. Therefore, the Ser to Thr mutation was tested in the context of the GIRK2 PIP chimeric channel. The GIRK2 PIP S148T mutation leads to dramatic loss of sensitivity for inhibition by alcohols. Briefly, the rank order of inhibition by 50 mM alcohols were: EtOH (−4±1%)<1-PrOH(−15±1)<1 BuOH(−28±1), and MPD (−36±1) (FIGS. 6D,E). Therefore a significant loss of sensitivity to inhibition occurs when Ser148 is mutated to a Thr. A dose response assay was conducted for inhibition using 1-Propanol and MPD for GIRK2 PIP mutants. The $IC_{50}$ for 1-PrOH was around 5.1±0.2 mM for GIRK2 PIP L257W mutant, whereas it was 687±236 for GIRK2 PIP S148T mutant channel (FIG. 6D). Similarly, the $IC_{50}$ for MPD was around 7.7±1.0 mM for MPD GIRK2 PIP L257W, whereas it was 147.0±31.4 mM MPD (FIG. 6F). Thus these alcohols inhibit GIRK2 PIP in a dose dependent manner, and the sensitivity to inhibition is altered by ~20 fold for MPD and ~100 fold for 1-PrOH when a Ser at the P-loop is mutated to a Thr.

These data led to the two-site model for modulation by alcohols for GIRK channels, where the MPD bound hydrophobic pocket significantly affects activation but not inhibition and the pore-loop significantly affects sensitivity to inhibition. The corresponding mutation S136T of IRK1 lead to mutants that had no functional current (n=5, data not shown), and therefore whether the sensitivity to inhibition could also be altered for IRK1 was not assessed. Nevertheless, the experiments with GIRK4, and with GIRK2 PIP, show that sensitivity to alcohol inhibition can be attenuated my mutating this Ser residue to a Thr at the pore region of two different GIRK channels.

Figure 7A:
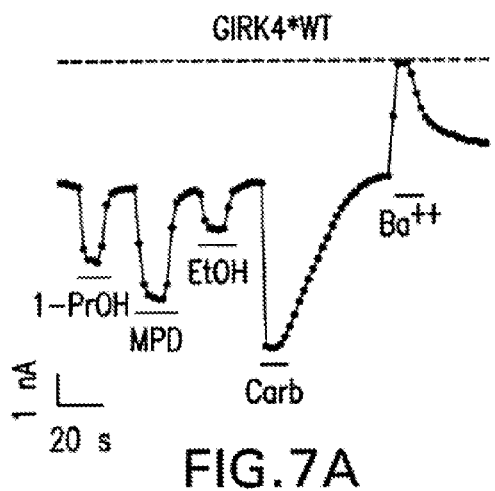
FIGS. 7A-7F show amino-acid substitution at GIRK4* Leu252 confirms alteration of alcohol Gβγ mediated currents occurs for another GIRK channel.
Figure 7B:
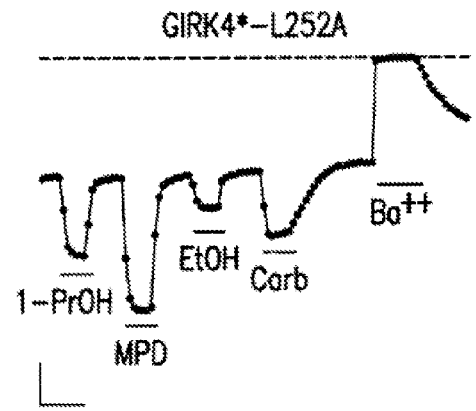
Figure 7C:
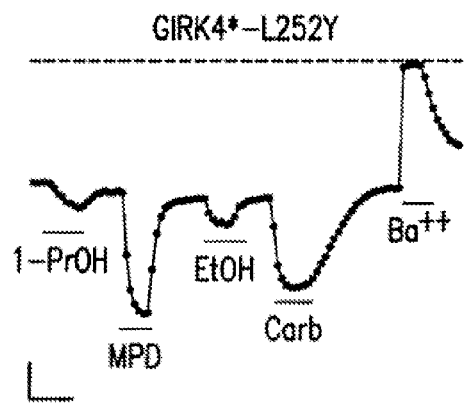
Figure 7D:
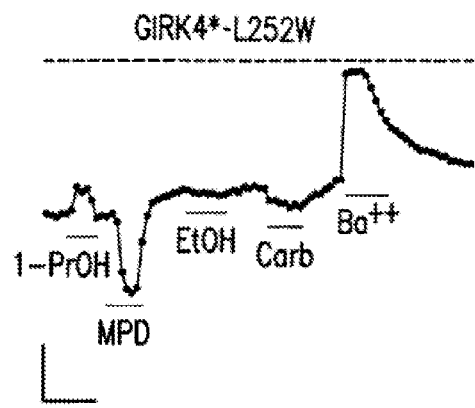
Figure 7E:
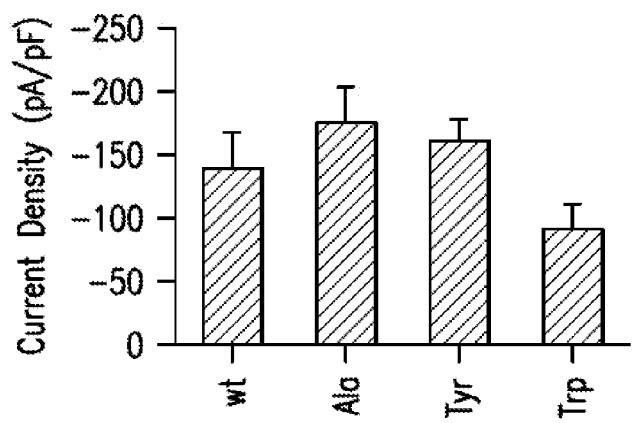
Figure 7F:
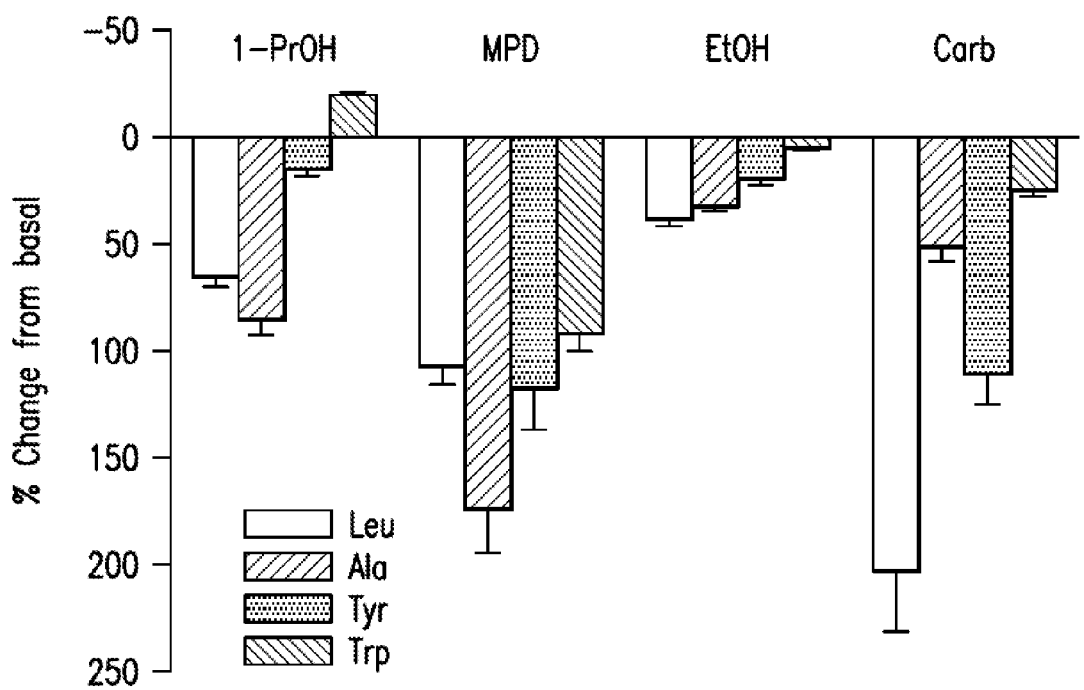
Figure 8:
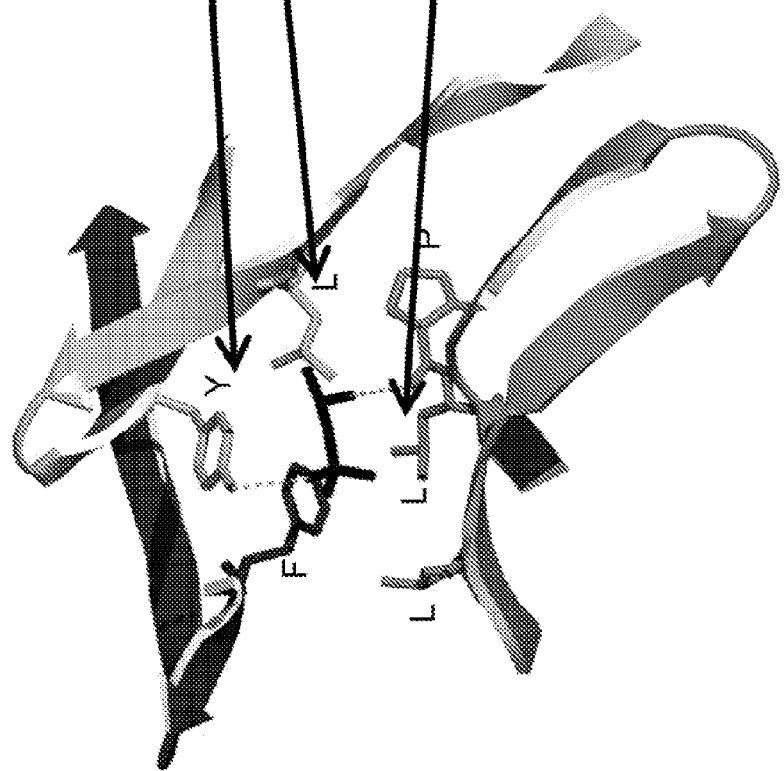
FIG. 8 summarizes data presented herein.

Mutation at Leu252 Shows a Loss of Activation by Alcohols for the GIRK4* Channel To confirm that the site of activation by alcohols is at the cytoplasmic hydrophobic pocket in GIRK4*, we mutated Leu252, which corresponds with Leu257 of GIRK2, to Ala, Tyr and Trp. Wild type GIRK4* basal currents are large, (−138±28.95 pA/pF) and the Ala, Tyr and Trp mutations at this position do not alter basal current (FIG. 7E). The rank profile for activation for GIRK4* was: MPD(113±14%)<1-PrOH(64±7%)<EtOH(36±3%). FIG. 7B shows that mutating Leu to Ala leads to a channel for which percent activation by MPD(179±22%), and 1-PrOH(86±8%) are significantly larger than for wild type (FIG. 7A). Substituting a Tyr at this position, showed a loss in activation by 1-PrOH(15±3%) and EtOH (20±3%) (FIG. 7C). Furthermore, substituting to the largest amino acid, Trp, the L252W mutant channel was now inhibited by 1-Propanol (−19±2%) and shows a loss of activation by EtOH(5±2%) (FIG. 7D). In addition, the Carb activation of GIRK4* Wild type, was 231±38% of basal current, however, all three substitutions, the Ala(51±8%), the Tyr (110±14%), and the Trp(23±3%) lead to significant loss of G-protein mediated activation (FIG. 7F).

These mutations show that this conserved Leu at the MPD hydrophobic pocket affects channel activation by alcohols and G-protein for both GIRK2 and GIRK4*. In the context of GIRK4* changing this amino-acid to the much smaller Ala lead to larger activation by possibly increasing the cavity of the hydrophobic pocket. When the bulkier Tyr, is substituted, it leads to decreased activation by 1-PrOH, and EtOH, whereas substitution to the largest amino-acid, Trp, leads to loss of activation by 1-PrOH, and thus is now inhibited by this alcohol, at the second site.

2. DISCUSSION

It was shown that MPD, which is an alcohol that was bound to distinct hydrophobic pockets in the crystal structure of the cytoplamic domain of IRK1 modulates IRK1 and GIRK2, activates a GIRK2 channel in a similar manner as other alcohols reported (low affinity, G-protein independent), whereas MPD slightly inhibits IRK1. Mutagenesis of GIRK2 at this hydrophobic pocket led to alteration in activation by alcohol. However, there was no change in the inhibition of IRK1 or a chimeric IRK1-like GIRK2 channel by mutation at this pocket. This led to the hypothesis that a second site could exist in these channels that is responsible for inhibition. It also was shown that mutation at the pore loop leads to loss of inhibition by 1-butanol for GIRK4, and the same mutation leads to loss of sensitivity to inhibition for the chimeric GIRK2 channel. A second GIRK channel, the GIRK4* channel, was studied to validate the initial finding that the site of activation by alcohol is at this MPD-bound hydrophobic pocket at the cytoplasmic domain of the GIRK channels.

Activation of GIRK at the MPD-Bound Hydrophobic Pocket

Mutagenesis data from both GIRK2 and GIRK4* receptors led to a conclusion that this cytoplasmic hydrophobic pocket is significant for activation. Increasing bulkyness at this pocket by introducing the Tyr lead to loss of activation by alcohols, whereas, introducing a Trp lead to significant loss of activation and introduced an inhibition component of modulation by alcohols. There was a difference between GIRK2 and GIRK4* in the rank of activation. GIRK2 displayed the rank 1-PrOH>MPD>EtOH, whereas GIRK4* displayed the rank MPD>1-PrOH>EtOH. When the Leu was mutated to Trp for the respective channel, EtOH activation was diminished for both channels, whereas, the second ranked activator now switched to being an inhibitor. The difference in rank order of wild type GIRK2 and GIRK4* could be a combination of sensitivity to activation and inhibition at the two different sites. Furthermore, in GIRK4*, effectively losing the bulkyness of the Leu sidechain by mutating to Ala led to increased activation by 1-PrOH, and MPD. Therefore, it is proposed that the increasing bulkyness at this position in the hydrophobic pocket leads to loss of alcohol activation. Furthermore, mutating this Leu in both GIRK2 and GIRK4* led to loss of Carbachol activation. Therefore, leucine is also significant for G-Protein mediated activation of GIRK channels.

This conserved Leu257 extends from the βDβE region. Another amino-acid from βDβE domain is Ile244, and when this Ile is mutated to Ala, and Trp, there is a loss of surface staining for the mutants. Therefore, this study highlights the importance of βDβE domain for both assembly/trafficking and activation by agonists. A recent study reported that a mutation in GIRK4 was isolated from human patient that had acute episode of atrial fibrillation (Calloe et al., Biochem Biophys Res Commun. 2007 Dec. 28; 364(4):889-95). This mutant, GIRK4 G247R, leads to a loss of basal, and G-protein activated currents. From sequence and structural alignments, Gly247 would be at the βDβE domain (Calloe et al. 2007) and thus this domain is significant for proper function of GIRK channels.

The Ala/Trp mutagenesis scan showed that mutations at the Y58 position, from the N-terminus domain, is significant for channel function. Substitution of this Tyr to Ala or Trp led to loss of cannel function, although the channels were at the plasma membrane. This Y58 has been shown to be significant in the interaction of the N-terminus to the C-terminus. In fact, this Y58 is thought to interact with the L342 from the βLβM loop, which is also a part of this hydrophobic pocket (Sarac et al., 2005). It is known that amino-acids from the βLβM loop are significant for GIRK channel activation. In GIRK2, Leu342 and Tyr349 are part of the MPD-bound hydrophobic pocket. The L342W mutant channel is non functional, while being at the plasma membrane, whereas Leu342A mutant channel leads to small basal current, and a loss of G-protein activation. The Y349W mutation leads to loss of 1-PrOH, and G-protein activated currents. GIRK channels have a conserved Leu at the position 344, which is a Glu in the G-protein insensitive channel IRK1 (Finley et al., 2004; He et al., 1999). The L344E mutant channel leads to a loss of G protein beta/gamma subunit activated current, while preserving EtOH currents (Finley et al., 2004). The proximity to this G-protein sensitive site, as well as the loss of G-protein activation for all of the mutations at the hydrophobic pocket, suggests that this hydrophobic pocket might be the sight of convergence of G-protein and alcohol mediated activation of GIRK channels.

Two crystal structure of GIRK1-Kirbac3 chimeric channel have been reported (Finley et al., 2004 J. Physiol. 2004 Mar. 16; 555(Pt 3):643-57). The two structures are of a putative open, and a putative closed channel, where the putative open channel has a open G-loop. The study also reported that there was a difference between the open and closed channel by the βLβM loop. Here, the IRK1-MPD bound channel was fitted to both of the structures, and it was determined that the IRK1+MPD fits best to the putative open channel. It is proposed that the IRK+MPD channel is an agonist bound, and activated form of a GIRK channel. The G-loop for the IRK+MPD is closed, and it was hypothesized that this is a closed channel. The chimeric channel, however, exhibits a transmembrane domain-G-loop interaction, and this interaction could lead to the G-loop being open. The G-loop could not be studied in the closed state for crystal structures obtained from cytoplasmic domain, because the interaction with the transmembrane domains is lacking. Nevertheless, based on fitting IRK-MDP crystal structure with the two structures of GIRK1-KIRBac1 chimeric channel, it is concluded that the hydrophobic pocket of MPD bound structure fits well with that of the putative open chimeric structure.

Inhibition at the Pore Domain

The equimolar alcohol series for inhibition of IRK1 currents showed that the longer chain alcohols have a stronger effect on inhibition. The GIRK2 PIP chimera had a relatively high sensitivity to inhibition by 1-PrOH and MPD. When the PIP GIRK2 S148T mutant channel was assessed, sensitivity to inhibition was greatly decreased. One possibility is that this Ser site is a binding site for alcohol, and mutating to Thr leads to loss of binding by the alcohol. A second possibility is that this as this Ser is close to the pore, a Ser at position 148 leads to high susceptibility to pore collapse. The alcohols could bind to a hydrophobic pocket in the vicinity, and promote the collapse. The Thr mutation then could lead to a channel that is not as susceptible to the collapse, and therefore the current is less sensitive to inhibition. The C-type inactivation in the KCSA channel has been associated with mutations of amino-acids in the same region as the S148 (Cordero-Morales J F et. al).

3. MATERIALS AND METHODS

Molecular Biology and Cell Culture:

GIRK2c, GIRK4, IRK1, M2R and m-Phosducin were subcloned into PCDNA3.1 vector (Invitrogen). Point mutations were introduced by Quickchange site directed mutagenesis kit (Stratagene). The GIRK2 PIP mutant was generated by overlap-PCR method. Briefly, amino acid 216-NLRKSHL-222 (SEQ ID NO: 25) of IRK1 was swapped into 228-DL-RNSHL-234 (SEQ ID NO: 26) of GIRK2, in the region designated βC-βD loop in the crystal structure. Mutations were confirmed by automated DNA sequencing methods.

HEK 293T cells were cultured in DMEM supplemented with 10% FBS, and 1× Glutamax (Invitrogen) in a humidified 37° incubator with 5% $CO_2$. Cells were plated in a 12 well dish, and were transiently transfected using Lipofectamine 2000 (Invitrogen). After 12-24 hrs, cells were re-plated to 12-mm glass coverslips coated with poly-D-Lysine (20 microgram/ml).

Surface Labeling:

HEK293T cells were transfected with 0.5 micrograms of wildtype or mutant GIRK2c channel containing an extracellular HA epitope inserted between Ile126 and Glu127 (Finley et al., 2004). Twenty-four to forty-eight hours after transfection, cells were removed from the incubator, and all subsequent steps were carried at 22-25 degrees C. The cells were washed with 1×DPBS (Invitrogen), then were fixed with 2% PFA in DPBS for 10 min, followed by rinsing with 1×DPBS. Cells were incubated with blocking buffer (3% BSA in 1×DPBS) for 1 hr then with a mouse antibody to HA (1:400 in blocking buffer. Covance) for 2 hrs at 22 degrees C. After rinsing with 1×DPBS, cells were then permeabilized with 0.25% TritonX-100 (sigma) in blocking buffer for 10 min at 22° C. Cells were incubated with blocking buffer for 1 hr then with a rabbit antibody to GIRK2 (1:200 in blocking buffer; Alomone) for 2 hrs. Cells were rinsed, and were then co-incubated with anti-mouse-Alexa-647 and anti-rabbit-Alexa-488 antibodies (1:300; Invitrogen) for 1 hr in the dark. Cells were then rinsed with 1×DPBS, and then mounted on microscope slides using Progold anti-fading reagent (Invitrogen). Images were collected using confocal fluorescence microscopy (Leica).

Electrophysiology:

HEK293 cells were transfected with 0.2 micrograms of channel cDNA. The cells were co-transfected with 0.04 micrograms of eYFP cDNA to identify transfected cells. 0.8 micrograms of Muscarinic Receptor 2 (M2R) was also co-transfected for experiments with Carbachol. For experiments with and without m-phosducin, 0.8 ug of m-phosducin cDNA was used versus a PCDNA3.1 vector control.

Whole-cell patch clamp recordings were performed 24-72 hrs after transfection. Borosilicate glass electrodes (Warner Instruments) of 5-7 milliohms filled with intracellular solution (130 mM KCl, 20 mM NaCl, 5 mM EGTA, 2.56 mM $K_2ATP$, 5.46 mM $MgCl_2$, 0.30 mM $Li_2GTP$, and 10 mM HEPES (pH 7.4)) was used. Membrane currents were recorded using Axopatch 200B (Axon Instruments) amplifier, adjusted electronically for cell capacitance and series resistance (80-100%), filtered at 1 kHz with an 8-pole Bessel filter and digitized at 5 kHz with a Digidata 1200 interface (Axon Instruments). The cells rapidly perfused with a 20 mM $K^+$ (20K) solution (20 mM KCl, 140 mM NaCl, 0.5 mM $CaCl_2$, 2 mM $MgCl_2$ and 10 mM HEPES (pH7.4)). Alcohols, 5 μM Carbachol, and 1 mM $BaCl_2$ (diluted in 20K solution) were applied from outside the cell with the rapid perfusion system (Warner Instruments). Whole-cell currents were measured using a ramp protocol that holds at −40 mV, steps to −100 mV then ramps to +50 mV and repeats every 2 seconds. Current-voltage relationships also were obtained from the ramp protocol. This protocol was used to measure the inwardly rectifying currents at −100 mV and to ensure stability of recording by monitoring a reversal potential and inward rectification. Current density was measured by dividing inward current at −100 mV by membrane capacitance that was compensated during the recording. Basal currents were measured as the $Ba^{++}$ blocked inward currents at −100 mV. Alcohol and Carbachol modulated currents were measured by averaging two consecutive current readings upon reaching steady state, and subtracting the averaged basal current before and after the application of modulator. Pooled data are presented as Mean±SEM and evaluated for statistical significance by a 1-way ANOVA, followed by Bonferroni's multiple comparison post-hoc test.

4. REFERENCES

Blednov, Y. A., Stoffel, M., Alva, H., and Harris, R. A. (2003). A pervasive mechanism for analgesia: activation of GIRK2 channels. Proc Natl Acad Sci USA 100, 277-282.

Blednov, Y. A., Stoffel, M., Chang, S. R., and Harris, R. A. (2001). Potassium channels as targets for ethanol: studies of G-protein-coupled inwardly rectifying potassium channel 2 (GIRK2) null mutant mice. J Pharmacol Exp Ther 298, 521-530.

Cardoso, R. A., Brozowski, S. J., Chavez-Noriega, L. E., Harpold, M., Valenzuela, C. F., and Harris, R. A. (1999). Effects of ethanol on recombinant human neuronal nicotinic acetylcholine receptors expressed in Xenopus oocytes. J Pharmacol Exp Ther 289, 774-780.

Deitrich, R. A., Dunwiddie, T. V., Harris, R. A., and Erwin, V. G. (1989). Mechanism of action of ethanol: initial central nervous system actions. Pharmacol Rev 41, 489-537.

Finley, M., Arrabit, C., Fowler, C., Suen, K. F., and Slesinger, P. A. (2004). betaL-betaM loop in the Cterminal domain of G protein-activated inwardly rectifying K(+) channels is important for G(betagamma) subunit activation. J Physiol 555, 643-657.

He, C., Zhang, H., Mirshahi, T., and Logothetis, D. E. (1999). Identification of a potassium channel site that interacts with G protein betagamma subunits to mediate agonist-induced signaling. J Biol Chem 274, 12517-12524.

Inanobe, A., Matsuura, T., Nakagawa, A., Kurachi, Y. (2007). Structural Diversity in the Cytoplasmic Region of G Protein-Gated Inward Rectifier $K^+$ Channels 1 39-45

Kobayashi, T., Ikeda, K., Kojima, H., Niki, H., Yano, R., Yoshioka, T., and Kumanishi, T. (1999). Ethanol opens G-protein-activated inwardly rectifying $K^+$ channels. Nat Neurosci 2, 1091-1097.

Kruse, S. W., Zhao, R., Smith, D. P., and Jones, D. N. (2003). Structure of a specific alcohol-binding site defined by the odorant binding protein LUSH from Drosophila melanogaster. Nat Struct Biol 10, 694-700.

Lewohl, J. M., Wilson, W. R., Mayfield, R. D., Brozowski, S. J., Morrisett, R. A., and Harris, R. A. (1999). G protein-coupled inwardly rectifying potassium channels are targets of alcohol action. Nat Neurosci 2, 1084-1090.

Lovinger, D. M., White, G., and Weight, F. F. (1989). Ethanol inhibits NMDA-activated ion current in hippocampal neurons. Science 243, 1721-1724.

Mihic, S. J., Ye, Q., Wick, M. J., Koltchine, V. V., Krasowski, M. D., Finn, S. E., Mascia, M. P., Valenzuela, C. F., Hanson, K. K., Greenblatt, E. P., et al. (1997). Sites of alcohol and volatile anaesthetic action on GABA(A) and glycine receptors. Nature 389, 385-389.

Pegan, S., Arrabit, C., Slesinger, P. A., and Choe, S. (2006). Andersen's syndrome mutation effects on the structure and assembly of the cytoplasmic domains of Kir2.1. Biochemistry 45, 8599-8606.

Pegan, S., Arrabit, C., Zhou, W., Kwiatkowski, W., Collins, A., Slesinger, P. A., and Choe, S. (2005). Cytoplasmic domain structures of Kir2.1 and Kir3.1 show sites for modulating gating and rectification. Nat Neurosci 8, 279-287.

Rishal, I., Porozov, Y., Yakubovich, D., Varon, D., and Dascal, N. (2005). Gbetagamma-dependent and Gbetagamma-independent basal activity of G protein-activated K+ channels. J Biol Chem 280, 16685-16694.

Sarac, R., Hou, P., Hurley, K. M., Hriciste, D., Cohen, N. A., and Nelson, D. J. (2005). Mutation of critical GIRK subunit residues disrupts N- and C-termini association and channel function. J Neurosci 25, 1836-1846.

Signorini, S., Liao, Y. J., Duncan, S. A., Jan, L. Y., and Stoffel, M. (1997). Normal cerebellar development but susceptibility to seizures in mice lacking G protein-coupled, inwardly rectifying K+ channel GIRK2. Proc Natl Acad Sci USA 94, 923-927.

Vivaudou, M., Chan, K. W., Sui, J. L., Jan, L. Y., Reuveny, E., and Logothetis, D. E. (1997). Probing the G protein regulation of GIRK1 and GIRK4, the two subunits of the KACh channel, using functional homomeric mutants. J Biol Chem 272, 31553-31560.

Wick, M. J., Mihic, S. J., Ueno, S., Mascia, M. P., Trudell, J. R., Brozowski, S. J., Ye, Q., Harrison, N. L., and Harris, R. A. (1998). Mutations of gamma-aminobutyric acid and glycine receptors change alcohol cutoff: evidence for an alcohol receptor? Proc Natl Acad Sci USA 95, 6504-6509.

Zhang, H., He, C., Yan, X., Mirshahi, T., and Logothetis, D. E. (1999). Activation of inwardly rectifying $K^+$ channels by distinct PtdIns(4,5)P2 interactions. Nat Cell Biol 1, 183-188.

Zhou, Q., and Lovinger, D. M. (1996). Pharmacologic characteristics of potentiation of 5-HT3 receptors by alcohols and diethyl ether in NCB-20 neuroblastoma cells. J Pharmacol Exp Ther 278, 732-740.

Zhou, W., Arrabit, C., Choe, S., and Slesinger, P. A. (2001). Mechanism underlying bupivacaine inhibition of G protein-gated inwardly rectifying K+ channels. Proc Natl Acad Sci USA 98, 6482-6487.

Example 5

Examples of Embodiments of the Invention

The following are certain non-limiting examples of embodiments of the invention.

A1. A method for identifying an agent that modulates an inwardly rectifying potassium (Kir) channel activity, which comprises:
(a) contacting a Kir channel protein or a modified Kir channel protein having an alcohol-binding site with (i) an agent and (ii) an alcohol, and
(b) detecting a Kir channel activity, whereby an agent that alters the activity relative to a control activity determined without the agent is identified as an agent that modulates the Kir channel activity.

B1. A method for identifying an agent that modulates an inwardly rectifying potassium (Kir) channel activity, which comprises:
(a) contacting a modified Kir channel protein having an alcohol-binding site with an agent, and
(b) detecting a Kir channel activity, whereby an agent that alters the activity relative to a control activity determined without the agent is identified as an agent that modulates the Kir channel activity.

B2. A method for identifying an agent that modulates an inwardly rectifying potassium (Kir) channel activity, which comprises:
(a) contacting a modified Kir channel protein having an alcohol-binding site with an agent that binds to the alcohol binding site, and (b) detecting a Kir channel activity, whereby an agent that alters the activity relative to a control activity determined without the agent is identified as an agent that modulates the Kir channel activity.

C1. A method for modulating an inwardly rectifying potassium (Kir) channel activity, which comprises contacting a Kir channel protein, or a modified Kir channel protein having an alcohol-binding site, with an alcohol under conditions in which the alcohol modulates the Kir channel activity, wherein:
the alcohol comprises four or more carbon atoms, and/or
the alcohol comprises two or more hydroxyl moieties.

C2. The method of claim B1, which further comprises contacting the Kir channel protein or the modified Kir channel protein with an agent and determining whether the agent alters the Kir channel activity relative to a control activity determined without the agent, whereby an agent that alters the activity relative to the control activity is identified as an agent that modulates the Kir channel activity.

D1. A method for identifying a candidate agent that binds to an inwardly rectifying potassium (Kir) channel protein, which comprises:
inserting in silico a structure of an agent into a three-dimensional structure of an alcohol-binding site of a Kir channel protein or a modified Kir channel protein; and
comparing the fit of the agent in the three-dimensional structure with the fit of an alcohol in the three-dimensional structure;
whereby an agent having a fit comparable to the fit of the alcohol is identified as a candidate agent that binds to a Kir channel protein.

E1. The method of any one of the preceding applicable embodiments, wherein the modified Kir channel protein comprises a DE loop region and a LM loop region.

E2. The method of any one of the preceding applicable embodiments, wherein the modified Kir channel protein lacks a transmembrane region.

E3. The method of any one of the preceding applicable embodiments, wherein the modified Kir channel protein comprises a DE loop region and a LM loop region and lacks a transmembrane region.

E4. The method of any one of the preceding applicable embodiments, wherein the modified Kir channel protein comprises all or a portion of the N-terminal amino acids before the transmembrane region from a native Kir channel protein sequence.

E5. The method of any one of the preceding applicable embodiments, wherein the Kir channel protein comprises a Kir 2 protein amino acid sequence.

E6. The method of any one of the preceding applicable embodiments, wherein the modified Kir channel protein comprises an amino acid sequence from a Kir 2 protein amino acid sequence.

E7. The method of embodiment E5 or E6, wherein the Kir 2 protein amino acid sequence comprises the sequence of SEQ ID NO: 4 or a substantially identical variant thereof.

E8. The method of any one of the preceding applicable embodiments, wherein the Kir channel protein comprises a Kir 3 protein amino acid sequence.

E9. The method of any one of the preceding applicable embodiments, wherein the modified Kir channel protein comprises an amino acid sequence from a Kir 3 protein amino acid sequence.

E10. The method of embodiment E8 or E9, wherein the Kir 3 protein amino acid sequence comprises the sequence of SEQ ID NO: 8 or SEQ ID NO: 10 or a substantially identical variant thereof.

E11. The method of any one of the preceding applicable embodiments, wherein the alcohol comprises two or more hydroxyl moieties.

E12. The method of embodiment E1, wherein the alcohol comprises two hydroxyl moieties.

E13. The method of embodiment E1, wherein the alcohol comprises three hydroxyl moieties.

E14. The method of any one of the preceding applicable embodiments, wherein the alcohol comprises four or more carbon atoms.

E15. The method of embodiment E14, wherein the alcohol comprises five or more carbon atoms.

E16. The method of embodiment E14, wherein the alcohol comprises about five to about ten carbon atoms.

E17. The method of embodiment E14, wherein the alcohol comprises five carbon atoms.

E18. The method of embodiment E14, wherein the alcohol comprises six carbon atoms.

E19. The method of any one of the preceding applicable embodiments, wherein the Kir channel protein or the modified Kir channel protein is in a cell.

E20. The method of any one of the preceding applicable embodiments, wherein the Kir channel protein or the modified Kir channel protein is in a cell-free system.

E21. The method of embodiment E20, wherein the Kir channel protein, the modified Kir channel protein, the alcohol or the agent is in association with a solid phase.

E22. The method of any one of the preceding applicable embodiments, wherein the Kir channel protein or the modified Kir channel protein comprises a detectable label.

E23. The method of any one of the preceding applicable embodiments, wherein the alcohol comprises a detectable label.

E24. The method of any one of the preceding applicable embodiments, wherein the Kir channel activity detected comprises binding of the Kir channel protein or the modified Kir channel protein to the alcohol.

E25. The method of any one of the preceding applicable embodiments, wherein the Kir channel activity detected comprises membrane conductance.

E26. The method of embodiment E25, which comprises monitoring electric current conducted by a membrane.

E27. The method of any one of the preceding applicable embodiments, wherein the modified Kir channel protein comprises a N-terminal domain region, a DE loop region and a LM loop region, and wherein each region is from the same or a different Kir subunit.

E28. The method of any one of the preceding applicable embodiments, wherein one or more amino acids in a modified Kir protein are substituted.

E29. The method of embodiment E28, wherein one or more amino acids located in beta strands D and E, and intervening sequences, are modified.

E30. The method of embodiment E28 or E29, wherein one or more amino acids in beta strands L and M, and intervening sequences, are modified.

E31. The method of any one of embodiments E28-E30, wherein one or more amino acids in beta strands C and D, and intervening sequences, are modified.

E32. The method of any one of embodiments E28-E31, wherein one or more amino acids between the transmembrane regions are modified.

E33. The method of any one of embodiments E28-E32, wherein one or more amino acids between amino acid position 110 and amino acid position 165 are modified.

E34. The method of any one of embodiments E28-E33, wherein one or more amino acids between amino acid position 1 to amino acid position 80 are modified.

E35. The method of embodiment E28, wherein the modified Kir protein is a modified Kir 3.2c protein and the one or more amino acids are selected from the group consisting of Y58, I244, L257, L342, L344 and Y349.

E36. The method of embodiment E28, wherein the modified Kir protein is a modified Kir 3.4 protein and the one or more amino acids are selected from the group consisting of S143 and L252.

E37. The method of embodiment E28, wherein the modified Kir protein is a modified Kir 2.1 protein and the one or more amino acids are selected from the group consisting of F47, L232, L245, L339, E332 and Y227.

E39. The method of embodiment E12, wherein the alcohol is 2-methylpentane-2,4-diol.

E40. The method of embodiment E12, wherein the alcohol is (S)-(+)-2-methylpentane-2,4-diol.

F1. A composition of matter comprising an inwardly rectifying potassium (Kir) channel protein, or a modified Kir channel protein having an alcohol-binding site, and an alcohol, wherein:
the alcohol comprises four or more carbon atoms, and/or
the alcohol comprises two or more hydroxyl moieties.

G1. A composition of matter comprising a modified inwardly rectifying potassium (Kir) channel protein having an alcohol-binding site and an alcohol.

G2. A composition of matter comprising a modified inwardly rectifying potassium (Kir) channel, wherein:
the unmodified counterpart is activated by an alcohol; and
the modification decreases activation by the alcohol.

G3. The composition of matter of embodiment G2, wherein the modification results in the channel being inhibited by an alcohol.

G4. The composition of matter of embodiment G3, wherein the alcohol is MPD or 1-propanol.

G5. The composition of matter of any one of embodiments G2-G4, wherein the modified channel is a modified Kir3 channel.

G6. A composition of matter comprising a modified inwardly rectifying potassium (Kir) channel, wherein:
the unmodified counterpart is inhibited by an alcohol; and
the modification decreases inhibition by the alcohol.

G7. The composition of matter of embodiment G6, wherein the modification results in the channel being activated by an alcohol.

G8. The composition of matter of embodiment G7, wherein the alcohol is 1-butanol.

G9. The composition of matter of any one of embodiments G6-G8, wherein the modified channel is a modified Kir3 channel.

H1. A composition of matter comprising a crystal that includes an inwardly rectifying potassium (Kir) channel protein or a modified Kir channel protein having an alcohol-binding site, and an alcohol.

I1. The composition of any one of the preceding applicable embodiments, wherein the modified Kir channel protein comprises a DL loop region and a LM loop region.

I2. The composition of any one of the preceding applicable embodiments, wherein the modified Kir channel protein lacks a transmembrane region.

I3. The composition of any one of the preceding applicable embodiments, wherein the modified Kir channel protein comprises a DL loop region and a LM loop region and lacks a transmembrane region.

I4. The composition of any one of the preceding applicable embodiments, wherein the modified Kir channel protein comprises all or a portion of the N-terminal amino acids before the transmembrane region from a native Kir channel protein sequence.

I5. The composition of any one of the preceding applicable embodiments, wherein the Kir channel protein comprises a Kir 2 protein amino acid sequence.

I6. The composition of any one of the preceding applicable embodiments, wherein the modified Kir channel protein comprises an amino acid sequence from a Kir 2 protein amino acid sequence.

I7. The composition of embodiment I5 or I6, wherein the Kir 2 protein amino acid sequence comprises the sequence of SEQ ID NO: 4 or a substantially identical variant thereof.

I8. The composition of any one of the preceding applicable embodiments, wherein the Kir channel protein comprises a Kir 3 protein amino acid sequence.

I9. The composition of any one of the preceding applicable embodiments, wherein the modified Kir channel protein comprises an amino acid sequence from a Kir 3 protein amino acid sequence.

I10. The composition of embodiment I8 or I9, wherein the Kir 3 protein amino acid sequence comprises the sequence of SEQ ID NO: 8 or SEQ ID NO: 10 or a substantially identical variant thereof.

I11. The composition of any one of the preceding applicable embodiments, wherein the alcohol comprises two or more hydroxyl moieties.

I12. The composition of embodiment I11, wherein the alcohol comprises two hydroxyl moieties.

I13. The composition of embodiment I1, wherein the alcohol comprises three hydroxyl moieties.

I14. The composition of any one of the preceding applicable embodiments, wherein the alcohol comprises four or more carbon atoms.

I15. The composition of embodiment I14, wherein the alcohol comprises five or more carbon atoms.

I16. The composition of embodiment I14, wherein the alcohol comprises about five to about ten carbon atoms.

I17. The composition of embodiment I14, wherein the alcohol comprises five carbon atoms.

I18. The composition of embodiment I14, wherein the alcohol comprises six carbon atoms.

I19. The composition of any one of the preceding applicable embodiments, wherein the Kir channel protein or the modified Kir channel protein is in a cell.

I20. The composition of any one of the preceding applicable embodiments, wherein the Kir channel protein or the modified Kir channel protein is in a cell-free system.

I21. The composition of embodiment I20, wherein the Kir channel protein, the modified Kir channel protein, the alcohol or the agent is in association with a solid phase.

I22. The composition of any one of the preceding applicable embodiments, wherein the Kir channel protein or the modified Kir channel protein comprises a detectable label.

I23. The composition of any one of the preceding applicable embodiments, wherein the alcohol comprises a detectable label.

I24. The composition of any one of the preceding applicable embodiments, wherein the modified Kir channel protein comprises a N-terminal domain region, a DE loop region and a LM loop region, and wherein each region is from the same or a different Kir subunit.

I25. The composition of any one of the preceding applicable embodiments, wherein one or more amino acids in a modified Kir protein are substituted.

I26. The composition of embodiment I25, wherein one or more amino acids located in beta strands D and E, and intervening sequences, are modified.

I27. The composition of embodiment I25 or I26, wherein one or more amino acids in beta strands L and M, and intervening sequences, are modified.

I28. The composition of any one of embodiments I25-I27, wherein one or more amino acids in beta strands C and D, and intervening sequences, are modified.

I29. The composition of any one of embodiments I25-I28, wherein one or more amino acids between the transmembrane regions are modified.

I30. The composition of any one of embodiments I25-I29, wherein one or more amino acids between amino acid position 110 and amino acid position 165 are modified.

I31. The composition of any one of embodiments I25-I28, wherein one or more amino acids between amino acid position 1 to amino acid position 80 are modified.

I32. The composition of embodiment I25, wherein the modified Kir protein is a modified Kir 3.2c protein and the one or more amino acids are selected from the group consisting of Y58, I244, L257, L342, L344 and Y349.

I33. The composition of embodiment I25, wherein the modified Kir protein is a modified Kir 3.4 protein and the one or more amino acids are selected from the group consisting of S143 and L252.

I34. The composition of embodiment I25, wherein the modified Kir protein is a modified Kir 2.1 protein and the one or more amino acids are selected from the group consisting of F47, L232, L245, L339, E332 and Y227.

I35. The composition of embodiment I12, wherein the alcohol is 2-methylpentane-2,4-diol.

I36. The composition of embodiment I12, wherein the alcohol is (S)-(+)-2-methylpentane-2,4-diol.

Example 6

Examples of Nucleic Acid and Amino Acid Sequences

Provided hereafter are representative sequences of Kir channels. A coding nucleic acid sequence of a Kir2.1 channel is provided below (NCBI accession no. NM_000891.2; SEQ ID NO: 1).

```
   1 gcgcactgga gacctggaca gcgcgcagcc ttcccggcgc cggcgggctg ggtcttggga
  61 attctggttt gctttggctc actcgctttt tacaaaccac tggatcttac atgcctctgt
 121 accccccact tccactccat gtccacatga tcctgagaca gcaacaggac atgttctctg
 181 gatgtcagct gagtcattaa agtaactctg catgtcagta gacagacctt ggtagaacca
 241 caaggctccc agagacaccc atctctcctc atttttttgg tgtgtgtgtc ttcaccgaac
 301 attcaaaact gtttctccaa agcgttttgc aaaaactcag actgttttcc aaagcagaag
 361 cactggagtc cccagcagaa gcgatgggca gtgtgcgaac caaccgctac agcatcgtct
 421 cttcagaaga agacggtatg aagttggcca ccatggcagt tgcaaatggc tttgggaacg
 481 ggaagagtaa agtccacacc cgacaacagt gcaggagccg ctttgtgaag aaagatggcc
 541 actgtaatgt tcagttcatc aatgtgggtg agaaggggca acggtacctc gcagacatct
 601 tcaccacgtg tgtggacatt cgctggcggt ggatgctggt tatcttctgc ctggctttcg
 661 tcctgtcatg gctgtttttt ggctgtgtgt tttggttgat agctctgctc catggggacc
 721 tggatgcatc caaagagggc aaagcttgtg tgtccgaggt caacagcttc acggctgcct
 781 tcctcttctc cattgagacc cagacaacca taggctatgg tttcagatgt gtcacggatg
 841 aatgcccaat tgctgttttc atggtggtgt tccagtcaat cgtgggctgc atcatcgatg
 901 ctttcatcat tggcgcagtc atggccaaga tggcaaagcc aaagaagaga aacgagactc
 961 ttgtcttcag tcacaatgcc gtgattgcca tgagagacgg caagctgtgt ttgatgtggc
1021 gagtgggcaa tcttcggaaa agccacttgg tggaagctca tgttcgagca cagctcctca
1081 aatccagaat tacttctgaa ggggagtata tccctctgga tcaaatagac atcaatgttg
1141 ggtttgacag tggaatcgat cgtatatttc tggtgtcccc aatcactata gtccatgaaa
1201 tagatgaaga cagtccttta tatgatttga gtaaacagga cattgacaac gcagactttg
1261 aaatcgtggt catactggaa ggcatggtgg aagccactgc catgacgaca cagtgccgta
1321 gctcttatct agcaaatgaa atcctgtggg gccaccgcta tgagcctgtg ctctttgaag
1381 agaagcacta ctacaaagtg gactattcca ggttccacaa aacttacgaa gtccccaaca
1441 ctccccttg tagtgccaga gacttagcag aaaagaaata tatcctctca aatgcaaatt
1501 cattttgcta tgaaaatgaa gttgccctca agcaaaga ggaagacgac agtgaaaatg
1561 gagttccaga aagcactagt acggacacgc cccctgacat agaccttcac aaccaggcaa
```

-continued

```
1621  gtgtacctct agagcccagg cccttacggc gagagtcgga gatatgactg actgattcct
1681  tctctggaat agttacttta caacacggtc tgttggtcag aggcccaaaa cagttataca
1741  gatgacggta ctggtcaaga tgggtcaagc aagcggccac aagggactga ggcaagcaca
1801  atggtttcaa agaaagactg taagctccat gattagcata aagcactaac catgtctcca
1861  tgtgacccga tggcacatag atgttgtaga ataagttatg gttttttatg ttttgttttg
1921  tgtttttcca aaacttgaac ttgcaggcaa gccttggttg ggtatttgat ttatccagaa
1981  tgcttctctt tagggaacaa ggatgttttt aatggcataa caaaggcaag actctgcctt
2041  aattttgaa aagctgctaa ctacatgaac acaaatgtgt attttgttg cagtgtagtt
2101  ttccttttgt gtaattttaa agtcagtgtt gaatttatt gaaagctcat gatgcgcttc
2161  aaagtggcaa gtatttggct attaactgcc aaaacaagag cctgattttt tgaggccagt
2221  aattcgtttg ctagaattga tttttttct ctctctcttt gttacataag ggcattatgt
2281  aacactagcc gaatggtagc ctctgggttg ttgttttttt cttttcctcc atgatgttaa
2341  tgggttatct caaattttaa gttaaactac ctaaaataaa taccaaagat aatgcatatt
2401  tttgcacagt ggagcttaca cttaaaagaa acaaagccc catgggctgc cttgaaatca
2461  agagacaata actttgaacc tcagcaagac cttgaaccgc cggttcattt tgcaccttat
2521  tcagaaaata gagcatcata ctcaccgagt ctagtcagtg tagtgctttt aaaaattttg
2581  tcctttcatg taacttttt attttaagag gaagaagaag aaagggcac acacacacaa
2641  taccgacgtc tatccttcc tgctaggcag tgctggccag gctcatgtgt agtgtgcgag
2701  atggtgatgt actcttatat ttttctgggc ttttccttt gcacattcca aaattcattt
2761  cataagacaa gatcttcata ggacctcctt ggcatcctgg cattctcaaa actgagccat
2821  ccagcatgaa agataaatgg gttaaaccc ttgctgctga atttattgcc tggactgtca
2881  ggacatcacc agcccacctt caccttaggg aagatgccac acctggcctc cacacttgct
2941  cttctgatca gtctgtctgg attgagtcct acagtgtcag atagggcggc aaatgccaaa
3001  gcagggaaac agggaggtgt ggacaagcca gtttgatgca gcacttcaga tcaagtgctt
3061  aggaaggaga ggaaacttgc ctttttatg gcagaggata gtaatgaaaa tgtctcagta
3121  ttttagggtc aatgagagcc ataaaaatat aacataatca caagtaaagg agataatggt
3181  ctaaaacagc tatttcccctt ttctgtgtgc atacttatga ctgaatgtga gctaagcatt
3241  ttctcctgtg gagccctaga gcaggttact aaggaaggac acattgtttt ccagaagcct
3301  cccctgcctg gctgactgcc ttgctagaaa cataattttt ttttctcac tgaagctcaa
3361  taatggaact ctttttttt tttttttaa tttaaagttc cctatttgtg aattctggga
3421  ttactgactt ttctttttaa ttggagtctc aaaatcaact ctcttatggt attatatctc
3481  tgtatgccat taaaaaacag cttgttctag aatcatgtat tttgtaaact gatgtttgtg
3541  atggtctctg gttcttgaac agccatatct gaatgccgtg cctgcaaaac tatgacaatt
3601  tttgctgttt tcagccttca gatttgatgg cttgggaaac tgaggtgtta ttttcaatga
3661  aacaaagaaa gagatgttaa gcaagtggtt gttttagatc caaatgtaaa ggcaggtttg
3721  ggaaggtgtt taaagagttg gaggaattgg ggattgagtt gtaaagaaaa cttacagaag
3781  aggcaacaat ttggttcttg acagtgagag gatattgagg gcttcagctg ctgctattat
3841  gatgtttgc aaaggaaaat aatcaaacca aagagtattc agtgatatgt aaattaaatg
3901  aagatacagt ggagaatggg ggtgaccaca aaagaggctc ccctaaaca cacagtgctg
3961  ccacttaaaa agacttgaga aatttgaaag ggggtgggta tgggggggc aagaaagagg
4021  gagggaaatc tttcaactta tttctgaaaa agagaaaaaa atataaaatt tctggtgcac
```

-continued

```
4081 aggtttgttt tttcaagaaa attttgcaga agctatgttt ttaaagtgta catttttataa 4141 agtttatcag atattttcat atttaaagcc aaatgtaaat agaggtctgt aaagaaaaat 4201 aattgccata gaaagtataa tttcagtgca gtaatttctg agagctagta cctatatgct 4261 accggttagc atggttttag caaatatata ccagccttat aaggttcgta ttgctatgtt 4321 cttctgttat ttatttcagc atggactgtt catttgaaac ctttttctag ttattagcgt 4381 tttaacagtt acaagcttta aatggcaatt tttttttttt tttttttttt tttttttttt 4441 ttgtcaagag ccaagacaca ggtaatgcac gacattgatt gctgcatttt accttcaaaa 4501 tatttgtcct tattgactgg gtctccttaa ttaatgtaca catgtcatta gaatgcagac 4561 ggagggact caccatgaat atctggggtt gattcccaga tgtgtgttgc ttctctattg 4621 caagcagatt ccctgttgga tttacttcgg atttattccc ttttaaagaa tttttgccca 4681 tatctggaag ggcactatat ttttgggagg agccatagat tcctggttat cctattttta 4741 aacaaaatgt agacaaagtg aactctattt tgattattga gaaggagta gttttctatc 4801 cctctaagag tatacttgaa tcagacattt taaggatgtc actatggcac tgttgtcatt 4861 tccaaattcc tagaaaagtt tgttttactt tgttttatt ctgttaatgc attctttctt 4921 ctctttactt cctttcttac cagtacactc ctatctcaac tctgtttatt tgatgagttc 4981 tgtcccgtaa atcatatttc ccttacaatt aataaatgtc acttcatatt ttataataaa 5041 ccactcagta aaagcaaaag cttgtcctga gaagtagagt gagttctttt tcactctgtg 5101 tctaataatg ttaaggtggg aaaaaaaaaa gtgtggcata gctacctgcc catccccaac 5161 cctcagcaaa gtagaatctc ttttctggta attttgggtt tccgctctgg gctctggcaa 5221 gttgaacaat cctagccatt gacaatcgtg atagttatta ttttcccatt tgctgtcttt 5281 ttgtatctaa agtcttccta ttgtactgca caaaccatgg attgtacata ttttttatata 5341 ttatgtctta ttttattatt tctaaataaa aaaattaaaa attgaaaaaa aaaaaaa
```

An amino acid sequence of a Kir2.1 channel is provided below (NCBI accession no. NP_000882.1; SEQ ID NO: 2).

```
  1 mgsvrtnrys ivsseedgmk latmavangf gngkskvhtr qqcrsrfvkk dghcnvqfin 61 vgekgqryla difttcvdir wrwmlvifcl afvlswlffg cvfwliallh gdldaskegk 121 acvsevnsft aaflfsietq ttigygfrcv tdecpiavfm vvfqsivgci idafiigavm 181 akmakpkkrn etlvfshnav iamrdgklcl mwrvgnlrks hlveahvraq llksritseg 241 eyipldqidi nvgfdsgidr iflvspitiv heidedsply dlskqdidna dfeivvileg 301 mveatamttq crssylanei lwghryepvl feekhyykvd ysrfhktyev pntplcsard 361 laekkyilsn ansfcyenev altskeedds engvpestst dtppdidlhn qasvpleprp 421 lrresei
```

A nucleic acid sequence of a Kir2.1 channel is provided below (NCBI accession no. NM_008425.3; SEQ ID NO: 3).

```
  1 agagcgcact ggagccctgg ccagcgcgca gccttcccag caccggcaag cagggtcttg 61 ggaattctca cttgcttcgg ctcattctct ttcacaaaaa ccactggatc ttacatgctt 121 ctgtaatccc cacttccact ccatgtcccc atgatcctgt accagcaaca ggacaagttc 181 tctggatgtc agctgagtta ctaaggtaac tttgctggtc aaaagaaccc caaggttctc 241 ggaagcatcc atctctcctc attaataaat atatatatta attatatata tatataattt
```

-continued

```
 301 tttttggtgt gtcttcaccg aacattcaaa actgtttctt ctaagggttt tgcaaaaact
 361 cagactgttt tctaaagcag aaacactggc gtccccagcg aagcaatgg gcagtgtgag
 421 aaccaaccgc tacagcatcg tctcttcgga ggaagatggc atgaagctgg ccactatggc
 481 agttgccaat ggctttggga atggcaagag taaagtccat acccgacaac agtgcaggag
 541 ccgctttgtg aagaaagatg gtcattgcaa tgttcagttt atcaacgtgg gtgagaaggg
 601 acagaggtac ctggcagaca tctttactac ctgtgtcgac atccgctgga ggtggatgct
 661 ggttatcttc tgtcttgcct tcgtgctctc ctggctgttc tttggctgtg tgttttggtt
 721 gatagccctg ctccatgggg atctagatac ttctaaagtg agcaaagcat gcgtgtcaga
 781 ggtcaacagc ttcacggctg ccttcctctt ctccatcgag acccagacaa ccattggcta
 841 tggtttcagg tgtgtgacag acgagtgccc aattgctgtc ttcatggtgg tattccagtc
 901 aatcgtaggc tgcatcattg acgccttcat cattggtgca gtcatggcga agatggcaaa
 961 gccaaagaag agaaatgaga ctcttgtctt cagtcacaat gctgtgattg ccatgaggga
1021 tggcaaactc tgcttgatgt ggagagtggg taaccttcga aagagccacc ttgtggaagc
1081 tcatgtccgg gcacagcttc tcaaatctag gatcacttca gaggggagt atatcccttt
1141 ggaccagata gacatcaatg ttggttttga tagtggaatt gaccgcatat ttctagtgtc
1201 ccccatcact atcgttcacg aaatagatga agacagccct ttatatgact gagtaagca
1261 ggacattgac aatgcagact ttgaaattgt tgtcatactg gaaggcatgg tggaggcgac
1321 tgccatgaca actcaatgcc ggagttcgta tctggccaat gaaattctct ggggtcaccg
1381 ctatgagcaa gtgctctttg aagagaaaca ctactataaa gtagactatt caagattcca
1441 taagacttat gaagtaccta acaccccct ttgtagtgcc agagacttag cagagaagaa
1501 atacatcctt tcaaatgcaa attcattttg ctatgaaaat gaagttgccc taacaagcaa
1561 agaggaagag gaggatagtg agaacggagt cccagagagc acaagcacag actcacctcc
1621 tggcatagat ctccacaacc aggcaagcgt acctctagag cccaggccct taaggcgaga
1681 atcggagata tgactggctg attccgtctt tggaataact actttgctac acagcctgac
1741 gttggtcaga ggtccgagac agttatacag accatggtac tggtcgagag gtgggtgaaa
1801 gcaagcagcc acaagagact aaggctagca caaaggtttc aaggaaagac taagctggat
1861 gactgatgta aagtgctttg caggcctcca agagacatga tggcacatat ctgttgtagt
1921 ataagttatg gggttttaa tgtattgttt tgtgtttta caaaacttga atatgcaggc
1981 aagcctcagt ttgggtacat gacttacctg gaatgtttct ctttagggga acaagagtga
2041 ttttaatggc ataacacagg caagactctg ccttaatttt tgaaaagct gctaactaca
2101 tgaacacgaa ctgtattttt gttgcagtgt agtttatctt ttacataacg ttaagacgtc
2161 agtgttgagc attgttgaaa gcgcacagtg tgctttaaag catcaagtat ttggctatta
2221 actgccaaaa atgaaagcct gattttctga ggccagtaat ttgtttgcta aaaattgatc
2281 tctctgtcta cctgtcagtc tctgtctctg tctctctctc gttatctctc tctctctctc
2341 tctctctctc tctctcatta cataatagca ttatataaca ctagccaaat ggtagcctct
2401 gggttttata ctttctttt ccacaatgct aataggttat ctcaaactt cagttagacg
2461 accttaaatg aataccaaag ataatgcaca ttgttttgtt tttgttttg tttttttctt
2521 tttctttttt tttctttcct ttttttttct tttttgcac atggaggtta tattttta
2581 aaagaaaca aaggctcctg cacagattgt cttggaaatc cagagacacc atctttgaac
2641 ttcagcaggg tgtgaagcag tccgttcatt tttgcactat agtctgaaaa gaacaccaaa
2701 gtctgatcaa tgtagtgtgt tttcgagtct gttcttttgt gcttctttct tatttggagg
```

```
-continued
2761 ggaggaggga agcataggtc acagttacat atgcactata atcaatattt ttttctttcc
2821 cttttctga gcttttctct cttagcacat tccaaagttg gttccataag atcagatctt
2881 ggttgaactt tgttggtaac ctggcaccctt ccaaactgtc acccagcagg gaagatgaac
2941 agatttcaaa ttttgcagct gactcatagc cttgactgcc agggcatttc tagctcagtg
3001 tcacattaag aaagatgtct ggcctctagt cttgtccttc taaggtctct gcagagatag
3061 agagagagag agagagagag agagagagag agagagagag agagagagac tttcaatgca
3121 gcaatccact ttacaggtga gagggaagtt tccttttca tgacagaggg taagagggac
3181 tgtttcagta ttttaggtct tagtgagcca tataaacaca acataattac aagctaagga
3241 gttaagagtc taaagggtta tttctctctc tgtaaacatt catgattaat gccagtgggt
3301 cattgtctct tggaaagtct cagagcacgt tgccaaggac tcattatttt ctagaagcct
3361 cttttaccta ttcaccttcc tttataaaaa cctccctccc tttcccaaac actagctcaa
3421 tcattcaatt ctccctccct tgtttctct tggttttaat gttctctact tgtaaaccct
3481 ggggctgctg agttccttt tagttggcgt ctcaaaatca agcctctaat ggtattacac
3541 cctaatatgc cattaaaaat cagcttgttc tagaaccatg tattttattt aggttgatgt
3601 ttgtgccggt ctgtggcttg tgagcctctg tatctggata cagtgcctgt aagaaacgtt
3661 gacaatttct gctgttttca actttctaag tcaatggatt tgaaaactgt tggtgttatg
3721 gaaatcaaga gagaagcgtc gagaaagtgt acatctgggt tttaaggcag ggttgcaagt
3781 tgcttaaaga gtttgctggg ttggggacag ggagaagtca caggagagaa cacagactgg
3841 cttctgacag tgtgaggcta tggaaggctt cagatgctgc tattaaggtg atttgcaaag
3901 taaagtaatc aaaccaaaga gtattcagtg aatgtcaat caaatgaaga tgcagtaaag
3961 agtgggggtg acaacatgga ctgaccccaa acacaaaaag acttgagtta tttgaaaaga
4021 gggaggggt gggtacagag acaagaaaag tgggagggga aatctttcaa tttttttat
4081 ctttatttgc ttaaaaagaa gaaaccatct aaaatttctg gtgcatagat ttgttttcg
4141 tttgtttgtt tgttcgtttt ttttcttttt gttttcaag gaaaattttg cagaagcgac
4201 atttttaaag tgtacatttt ataaagttta tcagatattt tcatatttaa agccaaatgt
4261 aaatagaaat ctg
```

An amino acid sequence of a Kir2.1 channel is provided below (NCBI accession no. NP_032451.1; SEQ ID NO: 4).

```
  1 mgsvrtnrys ivsseedgmk latmavangf gngkskvhtr qqcrsrfvkk dghcnvqfin 61 vgekgqryla difttcvdir wrwmlvifcl afvlswlffg cvfwliallh gdldtskvsk 121 acvsevnsft aaflfsietq ttigygfrcv tdecpiavfm vvfqsivgci idafiigavm 181 akmakpkkrn etlvfshnav iamrdgklcl mwrvgnlrks hlveahvraq llksritseg 241 eyipldqidi nvgfdsgidr iflvspitiv heidedsply dlskqdidna dfeivvileg 301 mveatamttq crssylanei lwghryepvl feekhyykvd ysrfhktyev pntplcsard 361 laekkyilsn ansfcyenev altskeeeed sengvpests tdsppgidlh nqasvplepr 421 plrrsei
```

A nucleic acid sequence of a Kir3.1 channel is provided below (NCBI accession no. NM_002239.2; SEQ ID NO: 5).

```
   1 ctccgtccca ggggagaagg agaggcgtct gcaggggggca gagaccgcag ctacctgccg
  61 ggtgcgcccc ccacccagga gcgctcgctt cgccccctttt cctcccccgc ccccacctcc
 121 ttattggtgc tagtttgcag cgcccagctc ctgcgccttc gcttcgcgtt tgaatctggc
 181 tcgccccttc gtattatgtc tgcactccga aggaaatttg gggacgatta tcaggtagtg
 241 accacatcgt ccagcggctc gggcttgcag ccccagggggc caggccagga ccctcagcag
 301 cagcttgtgc ccaagaagaa gcggcagcgg ttcgtggaca agaacggccg gtgcaatgta
 361 cagcacggca acctgggcag cgagacaagc cgctacctct cggacctctt caccacgctg
 421 gtggacctca gtggcgctg gaacctcttc atcttcattc tcacctacac cgtggcctgg
 481 cttttcatgg cgtccatgtg gtgggtgatc gcctacactc ggggcgacct gaacaaagcc
 541 cacgtcggta actacacgcc ttgcgtggcc aatgtctata acttcccttc tgccttcctc
 601 ttcttcatcg agacggaggc caccatcggc tatggctacc gatacatcac agacaagtgc
 661 cccgagggca tcatcctctt cctcttccag tccatcctgg gctccatcgt ggacgccttc
 721 ctcatcggct gcatgttcat caagatgtcc cagcccaaga gcgcgccga ccctcatg
 781 ttcagcgagc acgcggtgat ctccatgagg gacggaaaac tcacgcttat gttccgggtg
 841 ggcaacctgc gcaacagcca catggtctcc gcgcagattg ctgcaagct gctcaaatct
 901 cggcagacac ctgagggtga gttccttccc cttgaccaac ttgaactgga tgtaggtttt
 961 agtacagggg cagatcaact ttttcttgtg tccccccctca caatttgcca cgtgatcgat
1021 gccaaaagcc ccttttatga cctatcccag cgaagcatgc aaactgaaca gttcgagatt
1081 gtcgtcatcc tagaaggcat tgtggaaaca actgggatga cttgtcaagc tcgaacatca
1141 tatactgaag atgaagttct ttggggtcat cgttttttc ctgtaatttc cttagaagag
1201 ggattctttta aagttgatta ctcccagttc catgcaacat ttgaagtccc caccccacct
1261 tacagtgtga agagcagga ggaaatgctt ctcatgtcgt ccccttaat agcaccagcc
1321 ataactaaca gcaaagaaag acataattct gtggaatgct tagatggact agatgatatt
1381 actacaaaac taccatctaa gctgcagaaa attactgaa gagaagactt tcccaaaaaa
1441 ctcttgagga tgagttctac aacttcagaa aaagcctaca gcttgggaga cttgcccatg
1501 aaacttcaac gaataagttc agttccggc aactcagaag aaaaactggt atctaaaacc
1561 accaagatgt tatctgatcc catgagccag tctgtggctg atttgccacc aaagcttcaa
1621 aagatggctg gaggagcagc taggatggaa gggaaccttc agccaaatt aagaaaaatg
1681 aactctgatc gcttcacata acaaagcact cccttaggca ttatttaatg tttgatttag
1741 taatagtcca atatttggcg atgaggtaat tctccctaag gaatctgaaa gtatattttc
1801 ctcccagttc tacaagcata tttgagaacc cttcctttcc caagtattgc gaatgtgcag
1861 aaagcaacag ttacggaggg aggacatcat aaggaagtta ttaacgggca tgtattatca
1921 catcaagcat gcaataatgt gcaaattttg catttagttt tatggcatga tttatatatg
1981 gcatatttat attgtatatt ctggaaaaaa aatatatata tatatttaaa ggggagatac
2041 tctccctgac atttctaaca tatgtattaa gccaaacatg agtgaatagc tttcagggcg
2101 ataaaactaa atatatgtct gtgtgtgtgt gtgtatgtat acacacatat acatatatat
2161 atacacatac atacacatac atacatacat acatatatat ctgataaaat tgtgatgttt
2221 tgttcaaagt tgtagttctt gtgcatgttt acttattag agtaggaagg ctactggcat
2281 taattattaa taccaaatat tttagcctta aatttttgtc attttaaaat ctgatttaat
```

-continued

```
2341 gttttctgct gtttaaggtc ttgggaggct ttcaattgta ttttatatga gagaatcaca 2401 caagtttgtg ctatctatgg ccctgcaaaa atataaccat tacatgttta aattgtaaat 2461 tttagagcat accagtactc agtatagcat tgaacatttc ttatgatttt taaaagttgc 2521 tagtactggg gagaaataat tgttgattaa tttgagaatt attcctttcc tagactaatt 2581 aaaatctgga aatctgtttt gtatatgatc taatacaaag atgagctctg aacaaacact 2641 gaatcatgtt aatagacagt agccaagtta tattgaatat atcagaatct gtgtgaagtt 2701 acacaattaa ttgtccctgt ttcaaactga gtaaattgga aacattttct ttctttttct 2761 ggaaattttg tccattttaa aaaccaatca ttttaagaag acatgacaat gcaatgaaac 2821 agatgataaa tatttatgct taaaatatgt atgtctaatt gagtctcttt tttattctgt 2881 tttcttgttt
```

An amino acid sequence of a Kir3.1 channel is provided below (NCBI accession no. NP_002230.1; SEQ ID NO: 6).

```
  1 msalrrkfgd dyqvvttsss gsglqpqgpg qdpqqqlvpk kkrqrfvdkn grcnvqhgnl 61 gsetsrylsd lfttlvdlkw rwnlfifilt ytvawlfmas mwwviaytrg dlnkahvgny 121 tpcvarvynf psaflffiet eatigygyry itdkcpegii lflfqsilgs ivdafligcm 181 fikmsqpkkr aetlmfseha vismrdgklt lmfrvgnlrn shmvsaqirc kllksrqtpe 241 geflpldqle ldvgfstgad qlflvsplti chvidakspf ydlsqrsmqt eqfeivvile 301 givettgmtc qartsytede vlwghrffpv isleegffkv dysqfhatfe vptppysvke 361 qeemllmssp liapaitnsk erhnsvecld gldditttklp sklqkitgre dfpkkllrms 421 sttsekaysl gdlpmklqri ssvpgnseek lvsktttkmls dpmsqsvadl ppklqkmagg 481 aarmegnlpa klrkmnsdrf t
```

A coding nucleotide sequence of a Kir3.2 channel is provided below (NCBI accession no. NM_002240.2; SEQ ID NO: 7).

```
  1 tgagtagcat tcattgaatc tgcggatttc atgacgtctc tctgcgtggt ccaccacttt 61 tctcctaacc ggggatttt ttttttcttct gccactctta tctttcccca cttcattcca 121 cccagtctcc ctgccccgtc cctgcccaaa cgcgcgcccc tccgccccctc ccttggcccc 181 agcgcccagc cctgctctcc gcgctcggcc agagggagcc agtccggaga cggccgcacc 241 tggctggaga ggctgggcgg gcggagggct ggagacccgc ggacgccggg aagccggacc 301 tggagccgga gcagccgcga gcagaatgga gtctcctaac agcctctcgg tgctgatgtg 361 aaatttgacc atctgattcc agttttttc ttttcctttt cttttttgca tttccttccc 421 tcgccatccg tcgtgtagtg aattgttcag tcttgctccg tttcaagaga ggagatcatg 481 attgagtgaa gccaccccgt ccgcagccag aaaagcaca aagaagaaac tgcaacaatg 541 gccaagctga cagaatccat gactaacgtc ctggagggcg actccatgga tcaggacgtc 601 gaaagcccag tggccattca ccagccaaag ttgcctaagc aggccaggga tgacctgcca 661 agacacatca gccgagatcg gaccaaaagg aaaatccaga ggtacgtgag gaaagacgga 721 aagtgcaatg ttcatcacgg caacgtgagg gagacctatc gctacctgac cgatatcttc 781 accacattag tggacctgaa gtggagattc aacctattga ttttgtcat ggtttacaca 841 gtgacctggc tctttttttgg aatgatctgg tggttgatcg catacatacg gggagacatg
```

-continued

```
 901 gaccacatag aggacccctc ctggactcct tgtgttacca acctcaacgg gttcgtctct
 961 gcttttttat tctcaataga gacagaaacc accattggtt atggctaccg ggtcatcaca
1021 gataaatgcc cagagggaat tattcttctc ttaatccaat ctgtgttggg gtccattgtc
1081 aatgcattca tggtgggatg catgtttgta aaaatctctc aacccaagaa gagggcagag
1141 accctggtct tttccaccca tgcagtgatc tccatgcggg atgggaaact gtgcctgatg
1201 ttccgggtag ggaccttag gaattcccac attgtggagg cttccatcag agccaagttg
1261 atcaaatcca aacagaccct ggaggggag ttcatcccgt tgaaccagac ggatatcaac
1321 gtagggtatt acacggggga tgaccgtctg tttctggtgt caccgctgat cattagccat
1381 gaaattaacc aacagagtcc tttctgggag atctccaaag cccagctgcc caaagaggaa
1441 ctggaaattg tggtcatcct agaaggaatg gtggaagcca cagggatgac atgccaagct
1501 cgaagctcct acatcaccag tgagatcctg tggggttacc ggttcacacc tgtcctgacc
1561 ctggaggacg ggttctacga agttgactac aacagcttcc atgagaccta tgagaccagc
1621 accccatccc ttagtgccaa agagctggcc gagttagcca gcagggcaga gctgcccctg
1681 agttggtctg tatccagcaa actcaaccaa catgcagaac tggagactga agaggaagaa
1741 aagaacctcg aagagcaaac agaaagaaat ggtgatgtgg caaacctgga gaatgaatcc
1801 aaagtttagt gccctagctg ggcaaaccct tctcttctcc ccccaacaca atctttcctt
1861 gtctctcatt ctctttcttt ttctgtctct cttgctttgt tctttatttg tttatattta
1921 attttacat gaccagaaaa caaatcttca aggtgtaaaa tatctacctg ccctctctca
1981 gttattcaga ttgacaaggt agacatggat ttgatgaaag tgcaaagtgc cctcatttgt
2041 ggcccaagcc tggtctcctc ccaaaatact acacatccaa ctcctggaga tttcagttac
2101 ttacctgcat gtgttgtaca ataccagatc actcaaaaag gtgtgtcaaa gattttacct
2161 gggatatgac aagcaaggtt tctggtgcct atttattcat tcagtgagac acagagtgga
2221 gccctcagtt ttatggatcc caattcattt catctactac agggtgaggt gcttgccccc
2281 atgtgggtgt ggcagttaca gggcccaggt gagctgaaga caaaccactg tacatatata
2341 tgccttatgt aattattttc tttttgtaat tagtaataaa acccagcatg tacaaaagta
2401 ccatagaaca gaactgctaa atactgtaca tagatgtatc attaatgtag gtttagatat
2461 ataactttag aaataagaag caaaa
```

<45>

An amino acid sequence of a Kir3.2 channel is provided below (NCBI accession no. NP_002231.1; SEQ ID NO: 8).

```
  1 makltesmtn vlegdsmdqd vespvaihqp klpkqarddl prhisrdrtk rkiqryvrkd
 61 gkcnvhhgnv retyryltdi fttlvdlkwr fnllifvmvy tvtwlffgmi wwliayirgd
121 mdhiedpswt pcvtnlngfv saflfsiete ttigygyrvi tdkcpegiil lliqsvlgsi
181 vnafmvgcmf vkisqpkkra etlvfsthav ismrdgklcl mfrvgdlrns hiveasirak
241 likskqtseg efiplnqtdi nvgyytgddr lflvspliis heinqqspfw eiskaqlpke
301 eleivvileg mveatgmtcq arssyitsei lwgyrftpvl tiedgfyevd ynsfhetyet
361 stpsslsael aelasraelp lswsvsskln qhaeleteee eknleeqter ngdvanlene
421 skv
```

A coding nucleotide sequence of a Kir3.4 channel is provided below (NCBI accession no. NM_000890.3; SEQ ID NO: 9).

```
   1 acacacacac acacacacac acacagagag agagagagag agagagagag agagagagat
  61 tgttccagct gctctcgcta gagaaaggga gtgacccaag gggccgcgag tgaagggaca
 121 ggatggctta ggtacctctg cccacaggac cccacaacag ggagaggttc cagctacagc
 181 tcctccgtgg ggtcatggca ggggctgggg agtcccctca aaagccctga gcccccctgc
 241 accgccgcta agggacaccc cagaagttag catcagtggg actcggaagc tccgatctca
 301 acaacatccc agctatggct ggcgattcta ggaatgccat gaaccaggac atggagattg
 361 gagtcactcc ctgggacccc aagaagattc aaaacaggc ccgcgattat gtccccattg
 421 ccacagaccg tacgcgcctg ctggccgagg caagaagcc acgccagcgc tacatggaga
 481 agagtggcaa gtgcaacgtg caccacggca acgtccagga gacctaccgg tacctgagtg
 541 acctcttcac caccctggtg gacctcaagt ggcgcttcaa cttgctcgtc ttcaccatgg
 601 tttacactgt cacctggctg ttcttcggct tcatttggtg gctcattgct tatatccggg
 661 gtgacctgga ccatgttggc gaccaagagt ggattccttg tgttgaaaac ctcagtggct
 721 tcgtgtccgc tttcctgttc tccattgaga ccgaaacaac cattgggtat ggcttccgag
 781 tcatcacaga gaagtgtcca gagggatta tactcctctt ggtccaggcc atcctgggct
 841 ccatcgtcaa tgccttcatg gtggggtgca tgtttgtcaa gatcagccag cccaagaaga
 901 gagcggagac cctcatgttt tccaacaacg cagtcatctc catgcgggac gagaagctgt
 961 gcctcatgtt ccgggtgggc gacctccgca actcccacat cgtggaggcc tccatccggg
1021 ccaagctcat caagtcccgg cagaccaaag aggggagtt catcccctg aaccagacag
1081 acatcaacgt gggctttgac acgggcgacg accgcctctt ccttgtgtct cctctgatca
1141 tctcccatga gatcaaccag aagagccctt tctgggagat gtctcaggct cagctgcatc
1201 aggaagagtt tgaagttgtg gtcattctag aagggatggt ggaagccaca ggcatgacct
1261 gccaagcccg gagctcctac atggatacag aggtgctctg gggccaccga ttcacaccag
1321 tcctcacctt ggaaaagggc ttctatgagg tggactacaa caccttccat gatacctatg
1381 agaccaacac acccagctgc tgtgccaagg agctggcaga aatgaagagg gaaggccggc
1441 tcctccagta cctccccagc cccccactgc tggggggctg tgctgaggca gggctggatg
1501 cagaggctga gcagaatgaa gaagatgagc caagggggct gggtgggtcc agggaggcca
1561 ggggctcggt gtgagggggtg cagcctccct aagacctcct gtcactggct tcagtgaaca
1621 cagacactgc agagcctggg agcaggggag gggaatagtt gagtgtgctg tttgggggct
1681 caggagccat caaggctgtg gggaggaacc ataaacccag ccctcacagc tcccagcaca
1741 gggcctccct gagccagtgg catcctgcct gggcccccca tggcagtgct gcctcttgta
1801 ggtgctggct aagggccagg ccaggatgag tttccccatg gtgaatgtta ccggatggca
1861 tctgttctct ccatgccctg ggtcacttcc ttttttgggt ctcacagacc cctccagggg
1921 ctgacaccta gagagaacca tcaccttgtc cctcattcct tccaccctga ggcttgctgt
1981 ggactcagag aggagactta cctgatgaga gctcaaacct ctagtctggg atgagctcac
2041 agagccctca tgagttaaga tccatccata tcacataggc aattccttt aaatcagata
2101 ccaacgaccc attactgaga ggtacagagc gtacagccct tggtgttctc tgctgttatc
```

```
-continued
2161  tgccaaatgt gtgtgttttt cctctgctgt gttctgtgtg tccagtgtag cctattggag 2221  aatcggtctc attagagtga ctcttagaag gtggcctggg actagacagc ccctctgagc 2281  acatgcatag tggcatcagc agcttcctgg cctactccca atcacactgt gccctgcacc 2341  tcccaccaag ggggaacccc agcagctggg gcttttcgag tgcttttttgg cccaagaatc 2401  tcagagtgct tctaatcatc acagtagttt ttgtgttttg ttttgttttg ttttgttttg 2461  ttttgttttg ttttgttttt ttcacaatct cagccagcct gcggtgtgac ctggggagaa 2521  agttgagtgt caggggacat gatgagccag ttggccctga aacaggaatg gggcaaagag 2581  aaaggagagc caggagcatt taaaaatcag catctgggcc aggcaagatg gctcacgcct 2641  gtgatcccag cattttggga ggccgaggcg ggtggatcat gaggtcagga gatcgagacc 2701  atcctggcta acacggtgaa accccgtctc tactgaaaat acaaaaaatt agccaggcat 2761  ggtggcaggt gcctgtagtc ccagctactc gggaagctga ggcagaagaa tggcatgaac 2821  ctgggaggtg gaggttgcag tgagccaaga tcatgccact gcactccagc ctgggcgaca 2881  gagcgagact ccatctcaaa aaaaaaaaaa ac
```

An amino acid sequence of a Kir3.4 channel is provided below (NCBI accession no. NP_000881.3; SEQ ID NO: 10).

```
  1  magdsrnamn qdmeigvtpw dpkkipkqar dyvpiatdrt rllaegkkpr qrymeksgkc 61  nvhhgnvqet yrylsdlftt lvdlkwrfnl lvftmvytvt wlffgfiwwl iayirgdldh 121  vgdqewipcv enlsgfvsaf lfsietetti gygfrvitek cpegiilllv qailgsivna 181  fmvgcmfvki sqpkkraetl mfsnnavism rdeklclmfr vgdlrnshiv easiraklik 241  srqtkegefi plnqtdinvg fdtgddrlfl vspliishei nqkspfwems qaqlhqeefe 301  vvvilegmve atgmtcqars symdtevlwg hrftpvltle kgfyevdynt fhdtyetntp 361  sccakelaem kregrllqyl psppllggca eagldaeaeq needepkglg gsreargsv
```

The entirety of each patent, patent application, publication and document referenced herein hereby is incorporated by reference. In particular, content of Pegan et al., *Biochemistry* 45: 8599-8606 (2006), including color content of the drawings, is incorporated herein by reference in its entirety. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a device" can mean one or more devices) unless it is contextually clear either one of the elements or more than one of the elements is described. The term "about" as used herein refers to a value sometimes within 10% of the underlying parameter (i.e., plus or minus 10%), a value sometimes within 5% of the underlying parameter (i.e., plus or minus 5%), a value sometimes within 2.5% of the underlying parameter (i.e., plus or minus 2.5%), or a value sometimes within 1% of the underlying parameter (i.e., plus or minus 1%), and sometimes refers to the parameter with no variation. For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claim(s) that follow(s).

What is claimed is:

1. A method for identifying an agent that modulates an inwardly rectifying potassium channel activity, which comprises:
   (a) inserting in silico a structure of an agent into a three-dimensional structure of an alcohol binding site of a Kir 2 or Kir 3 channel protein;
   (b) comparing the fit of the agent in the three-dimensional structure with the fit of an alcohol in the three-dimensional structure, whereby an agent having a fit comparable to the fit of the alcohol is identified as a candidate agent that binds to a Kir 2 or Kir 3 channel protein;
   (c) contacting a Kir 2 or Kir 3 channel protein with a candidate agent identified according to step (b); and
   (d) detecting a Kir 2 or Kir 3 channel activity,
   whereby an agent that alters the activity relative to a control activity determined without the agent is identified as an agent that modulates the inwardly rectifying potassium channel activity.

2. The method of claim 1, wherein the Kir 2 or Kir 3 channel protein of step (a) lacks a transmembrane region.

3. The method of claim 1, wherein the Kir 2 protein amino acid sequence of step (a) comprises the sequence of SEQ ID NO: 4.

4. The method of claim 1, wherein the Kir channel protein of step (a) has a 90% or more identical amino acid sequence to SEQ ID NO: 4.

5. The method of claim 4, wherein the Kir channel protein of step (a) lacks a transmembrane region.

6. The method of claim 1, wherein the Kir channel protein of step (a) has a 90% or more identical amino acid sequence to SEQ ID NO: 8 or SEQ ID NO: 10.

7. The method of claim 6, wherein the Kir channel protein of step (c) lacks a transmembrane region.

8. The method of claim 1, wherein the Kir channel protein of step (c) comprises a Kir 3 protein amino acid sequence.

9. The method of claim 8, wherein the Kir 3 protein amino acid sequence of step (c) comprises the sequence of SEQ ID NO: 8 or SEQ ID NO: 10.

10. The method of claim 1, wherein the Kir 2 or Kir 3 channel protein of step (c) has one or more amino acids that are modified compared to the corresponding Kir 2 or Kir 3 channel protein of SEQ ID NO: 4, SEQ ID NO: 8, or SEQ ID NO: 10.

11. The method of claim 10, wherein the Kir 2 or Kir 3 channel protein of step (c) lacks a transmembrane region.

12. The method of claim 10, wherein one or more amino acids between amino acid position 1 to amino acid position 80 are modified.

13. The method of claim 10, wherein one or more amino acids corresponding to Y58, I244, L257, L342, L344 and Y349 of Kir3.2 are modified.

14. The method of claim 10, wherein one or more amino acids corresponding to F47, L232, L245, L339, E332, and Y227 of Kir 2.1 are modified.

15. The method of claim 14, further comprising contacting the Kir 2 or Kir 3 channel protein with an alcohol.

16. The method of claim 15, wherein the Kir 2 protein amino acid sequence contacted with the alcohol comprises the sequence of SEQ ID NO: 4.

17. The method of claim 15, wherein the Kir 2 or Kir 3 channel protein contacted with the alcohol lacks a transmembrane region.

18. The method of claim 15, wherein the Kir channel protein contacted with the alcohol has a 90% or more identical amino acid sequence to SEQ ID NO: 4.

19. The method of claim 18, wherein the Kir channel protein contacted with the alcohol lacks a transmembrane region.

20. The method of claim 1, wherein the Kir channel protein is in a cell.

21. The method of claim 1, wherein the Kir channel protein is in a cell-free system.

22. The method of claim 1, wherein the Kir channel protein, or the agent is in association with a solid phase.

23. The method of claim 1, wherein the Kir channel protein comprises a detectable label.

24. The method of claim 1, wherein the alcohol comprises a detectable label.

25. The method of claim 1, wherein the Kir channel activity detected comprises binding of the Kir channel protein to the alcohol.

26. The method of claim 1, wherein the Kir channel activity detected comprises membrane conductance.

* * * * *